United States Patent
Arai et al.

(10) Patent No.: US 6,689,130 B2
(45) Date of Patent: Feb. 10, 2004

(54) TREATMENT APPARATUS FOR ENDOSCOPE

(75) Inventors: Keiichi Arai, Hachioji (JP); Hiroyoshi Watanabe, Kunitachi (JP); Keita Suzuki, Hachioji (JP); Yoshihiko Sugi, Hachioji (JP); Koichi Kawashima, Hachioji (JP); Masahiro Ishikawa, Hino (JP)

(73) Assignee: Olympus Corporation, Tokyo (JP)

( * ) Notice: Subject to any disclaimer, the term of this patent is extended or adjusted under 35 U.S.C. 154(b) by 79 days.

(21) Appl. No.: 10/160,946

(22) Filed: Jun. 3, 2002

(65) Prior Publication Data

US 2003/0009085 A1 Jan. 9, 2003

(30) Foreign Application Priority Data

Jun. 4, 2001 (JP) .................................. 2001-168775
Aug. 31, 2001 (JP) .................................. 2001-264327

(51) Int. Cl.$^7$ .............................................. A61B 18/18
(52) U.S. Cl. ............................ 606/46; 606/47; 600/104
(58) Field of Search ........................... 606/41, 42, 46, 606/47, 48; 600/101, 104, 153

(56) References Cited

U.S. PATENT DOCUMENTS

| | | | | |
|---|---|---|---|---|
| 3,835,842 A | * | 9/1974 | Iglesias | 600/105 |
| 3,939,839 A | * | 2/1976 | Curtiss | 606/46 |
| 4,116,198 A | * | 9/1978 | Roos | 606/46 |
| 4,362,160 A | * | 12/1982 | Hiltebrandt | 606/46 |
| 4,998,527 A | * | 3/1991 | Meyer | 600/104 |

FOREIGN PATENT DOCUMENTS

| | | |
|---|---|---|
| JP | 6-75402 | 10/1994 |
| JP | 9-66019 | 3/1997 |
| JP | 9-187415 | 7/1997 |
| JP | 2000-254146 | 9/2000 |

* cited by examiner

*Primary Examiner*—Roy D. Gibson
(74) *Attorney, Agent, or Firm*—Scully, Scott, Murphy & Presser

(57) ABSTRACT

A treatment apparatus to treat a tissue in a body cavity is disclosed. The apparatus comprises a base disposed in the vicinity of a tip-end portion of an endoscope, and an in-tissue inserting portion including a base end supported by the base and a tip end insertable in the tissue in the body cavity in a direction substantially parallel to the surface of the tissue, and extending to the tip end from the base end in a tapered shape. The in-tissue inserting portion has an inner side disposed in the vicinity of the surface of the tissue when inserted into the tissue. The apparatus further comprises a high-frequency electrode, for treating the tissue, supported by the base and disposed in the vicinity of the inner side of the in-tissue inserting portion, and a cable which supplies power to the high-frequency electrode from a high-frequency power source outside the body.

19 Claims, 45 Drawing Sheets

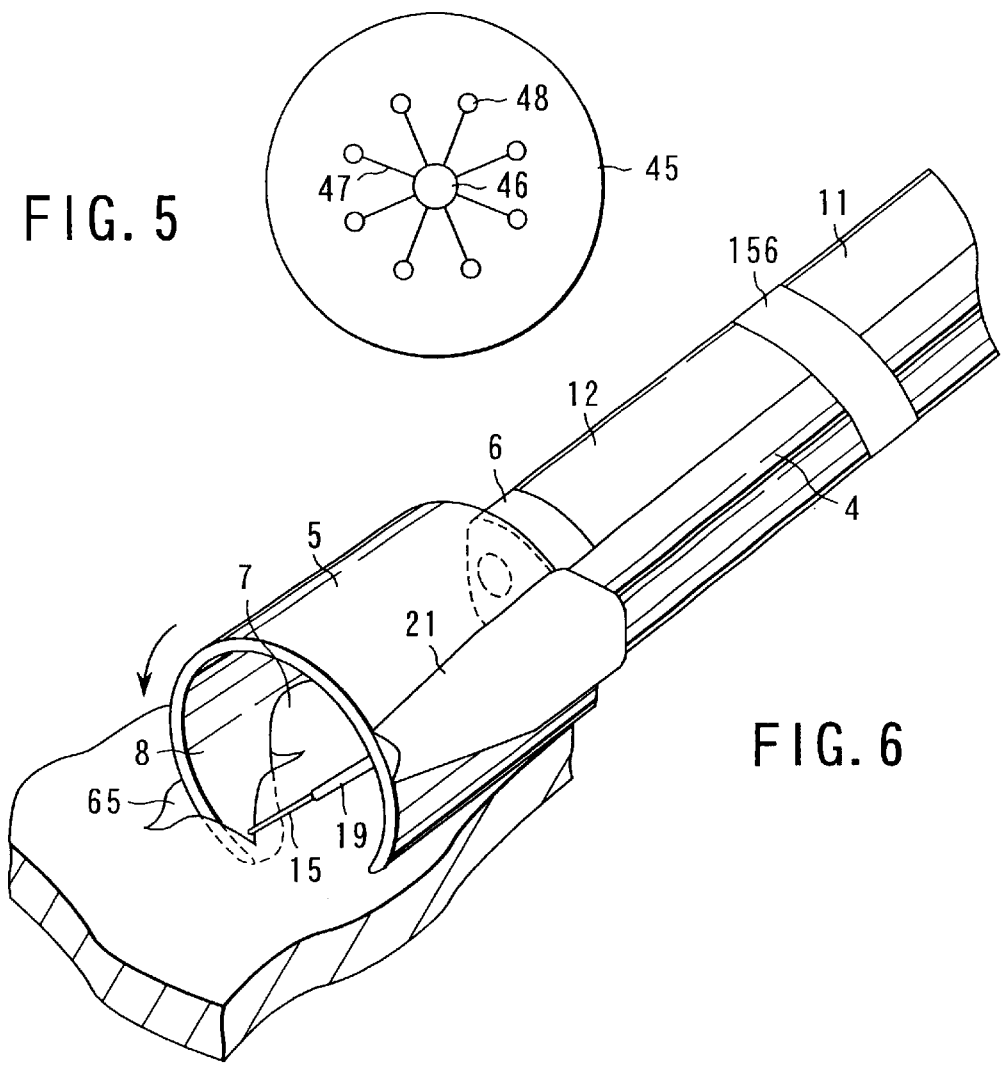
FIG. 5
FIG. 6
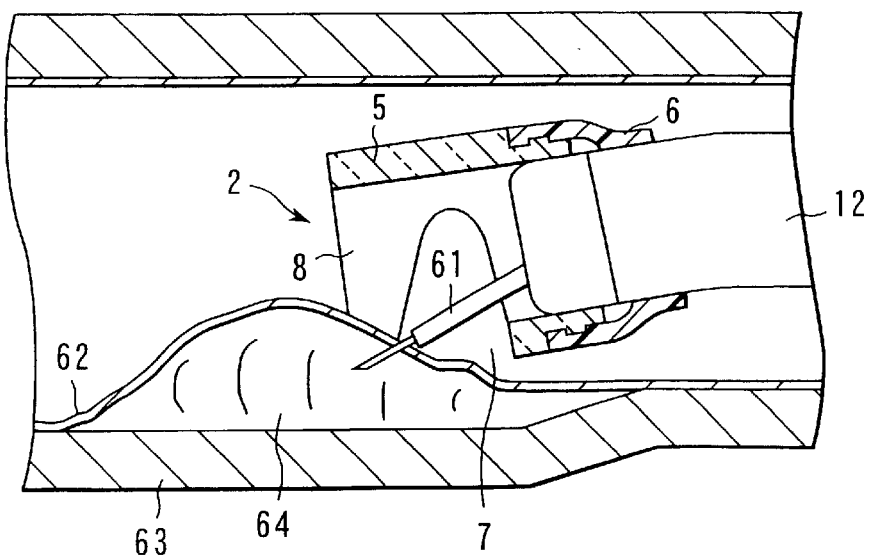
FIG. 7

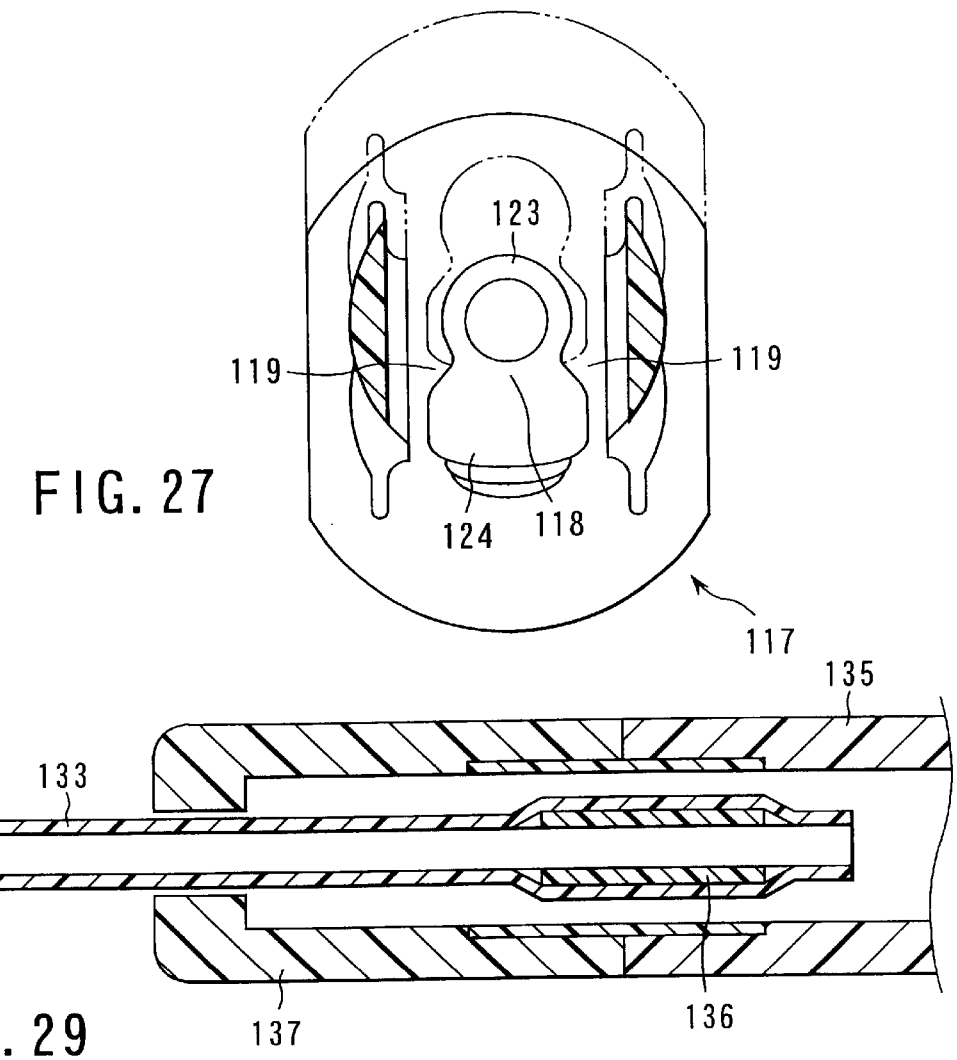
FIG. 27
FIG. 29
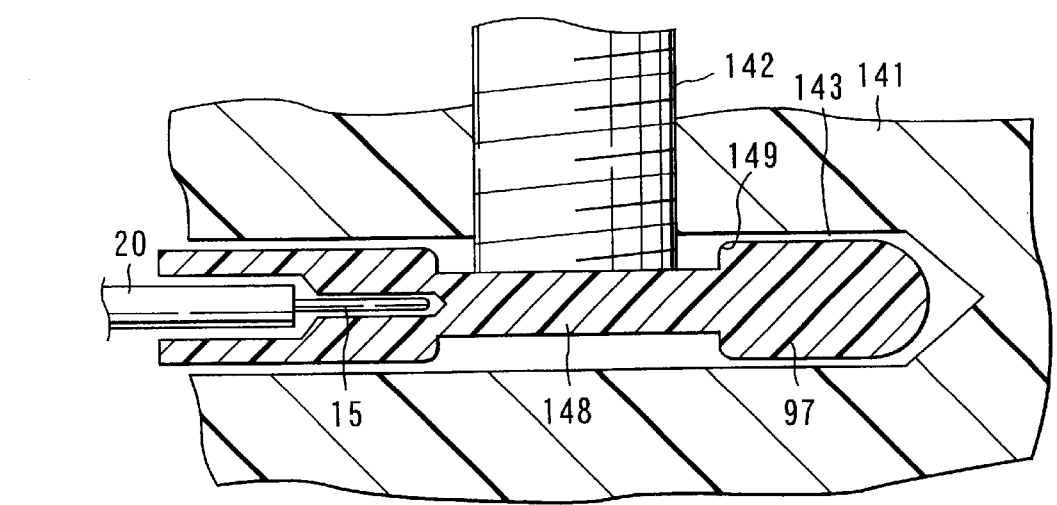
FIG. 30

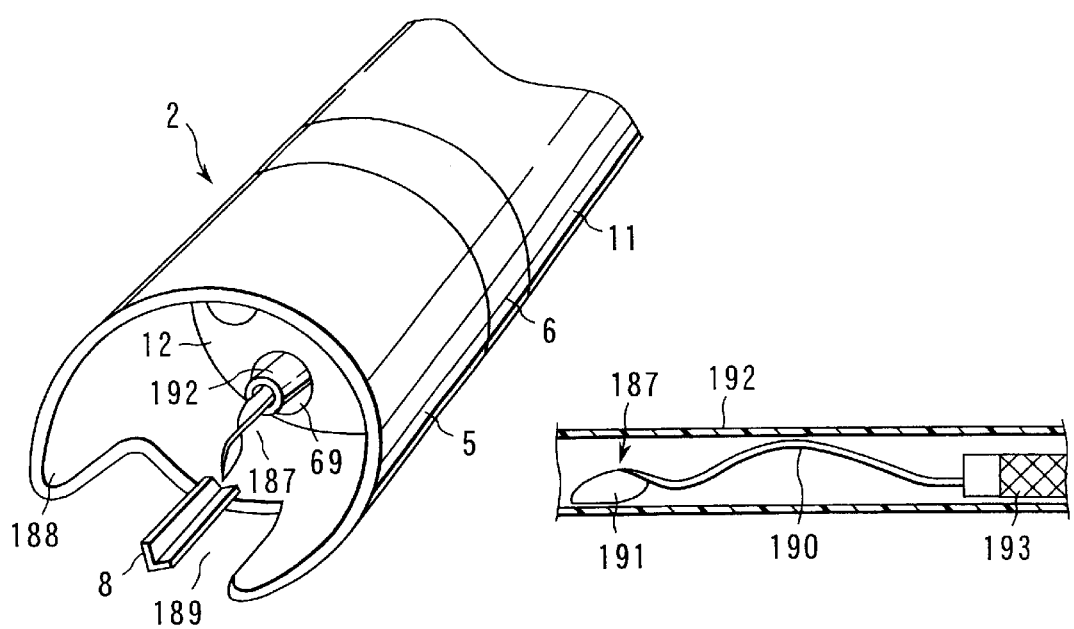
FIG. 38
FIG. 39
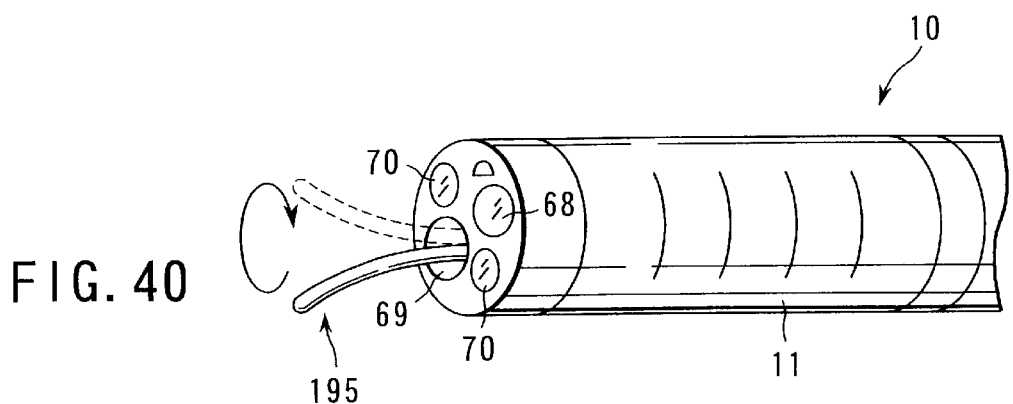
FIG. 40
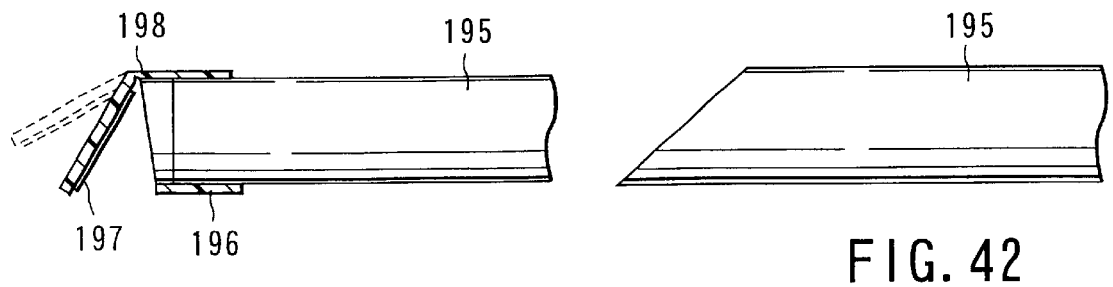
FIG. 41
FIG. 42

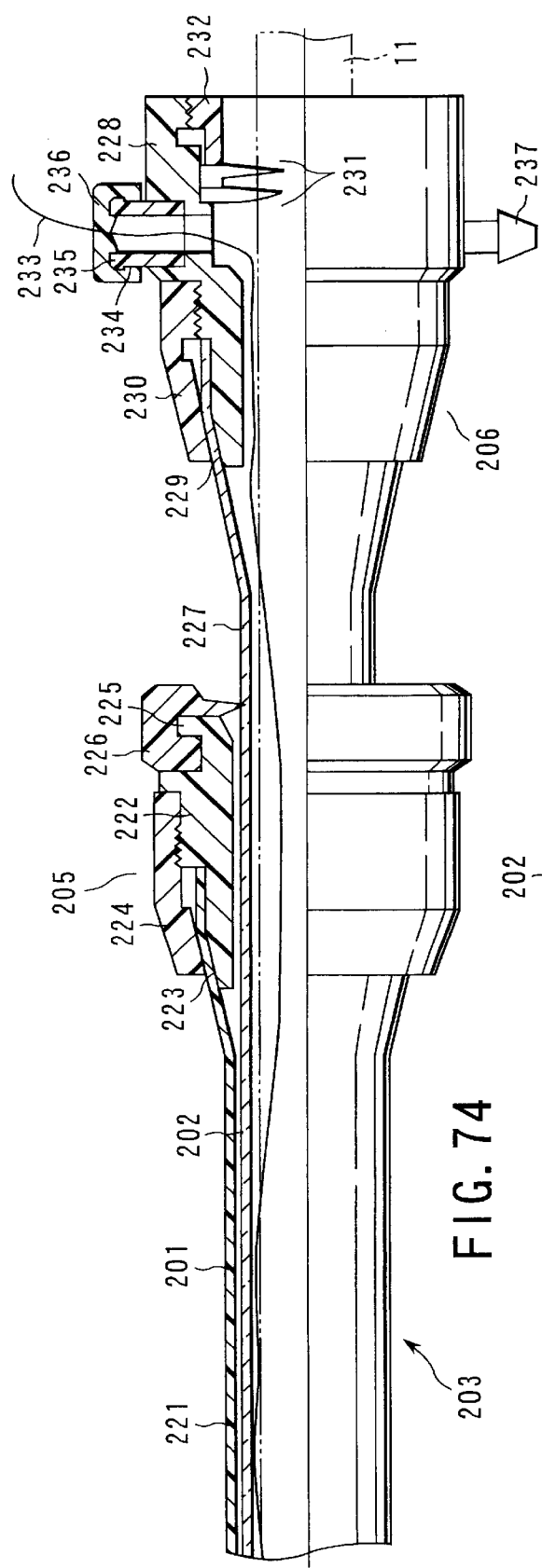
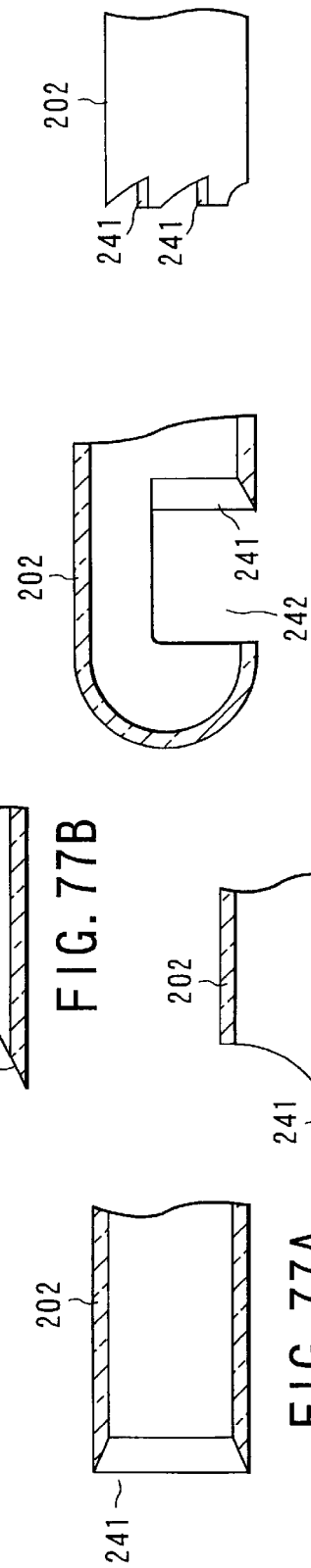
FIG. 74
FIG. 77A
FIG. 77B
FIG. 77C
FIG. 77D
FIG. 77E

TREATMENT APPARATUS FOR ENDOSCOPE

CROSS-REFERENCE TO RELATED APPLICATIONS

This application is based upon and claims the benefit of priority from the prior Japanese Patent Applications No. 2001-168775, filed Jun. 4, 2001; and No. 2001-264327, filed Aug. 31, 2001, the entire contents of both of which are incorporated herein by reference.

BACKGROUND OF THE INVENTION

1. Field of the Invention

The present invention relates to a treatment apparatus for an endoscope, which is used in combination with the endoscope, and which is used in treatments such as resecting of a mucosa.

2. Description of the Related Art

There has heretofore been a strip biopsy using a grip forceps and a snare as a method of resecting an affected area in a mucosa in an endoscopic manner. One example of a method by the strip biopsy comprises: incising a part swollen in a bump shape; picking up or turning over the incised mucosa with the grip forceps introduced through a treatment instrument insertion passage (channel) of the endoscope so that a boundary tissue can be observed with the endoscope; and bringing a high-frequency or a high-energy incising instrument such as a laser scalpel introduced through the treatment instrument insertion passage of the endoscope onto the tissue and incising the tissue.

In this method, the range from which the mucosa is stripped with one stroke of the scalpel is limited to a part onto which the incising instrument abuts. The incision therefore has to be repeated many times in order to resect the mucosa in a broad range, and this is troublesome. Moreover, since smoke or steam is generated during the incising of the tissue of a mucosa lower layer, it is difficult to observe the part to be incised because of the smoke or steam. Additionally, to secure a field of view every incision, the smoke or steam has to be removed by an air supply and sucking operation of the endoscope, and the treatment time lengthens. Furthermore, to cut only the tissue of the mucosa lower layer in a narrow range of a boundary between a muscle layer and mucosa, it is necessary to carefully position/operate the tip end of the incising instrument under observation by the endoscope. For this, complicated operations such as coupled operations for bending the endoscope, elevating the forceps, and moving the incising instrument forwards and backwards have to be carried out, these operations are laborious and require cautiousness, and the operator has to sustain concentration for a long time. Moreover, since the mucosa is turned over, it is difficult to see the range of the mucosa lower layer to be cut. Therefore, it is necessary to return the mucosa to its original position and to confirm the affected area, and this is laborious and troublesome. To solve this, there is a method of incising the mucosa around the affected area. However, an operation for incising only the mucosa with the incising instruments with whose tip ends the mucosa can be incised, such as a needle-shaped high-frequency scalpel and laser scalpel, requires sophisticated skills and is as exhausting as the aforementioned incising of the boundary part.

Furthermore, known examples of the method of resecting the affected area in the mucosa in the endoscopic manner include a method comprising: injecting physiological saline into the mucosa lower layer of the affected area; expanding the mucosa in the bump shape and separating the mucosa from the muscle layer; sucking the mucosa via the tip end of a hood attached to the tip end of an endoscope inserting portion or the tip end of an over tube with which the inserting portion of the endoscope is covered; and squeezing the high-frequency snare attached beforehand to the tip end of the instrument to resect the mucosa (an endoscopic mucosal resection cap (EMRC) method or an endoscopic mucosal resection tube (EMRT) method).

In any of these methods, the resection range is limited, and a broad range of the affected area cannot be resected at once. Therefore, to resect a broad range of affected area, a partial resection needs to be repeated many times, and this requires a considerably long time and much labor and increases the burden or the patient and operator. Moreover, the range resected with the high-frequency snare has a substantially circular shape. Therefore, since the resection is carried out a plurality of times, a redundantly resected part is sometimes generated. When the region parts resected in this manner overlap, the operation is carried out so as to prevent the parts from being resected deeper than necessary. As a result, the resecting operation has been very difficult. Moreover, the resection range of the mucosa changes by the sucked amount of the mucosa in the EMRC or EMRT method, and it is difficult to keep the sucked amount constant. Therefore, an operation of continuously and evenly resecting the parts adjacent to each other has been difficult.

In Jpn. Pat. Appln. No. 11-64774 filed by the assignee of the present invention (Jpn. Pat. Appln. KOKAI Publication No. 2000-254146 (published as of Sep. 19, 2000)), to avoid the various problems, an endoscope treatment apparatus in which a high-frequency incising instrument is attached to the tip end of the hood, and a high-frequency treatment instrument of the apparatus are disclosed. In the apparatus described in Jpn. Pat. Appln. No. 11-64774, only a length corresponding to the diameter of the hood can be incised. Therefore, to incise a long part, partial incision needs to be carefully overlapped and repeated. Additionally, to incise only the mucosa, the sucking operation of the endoscope is finely adjusted, it is necessary to correctly and carefully control the height by which the mucosa is sucked up in the hood, and the operation is not easy.

Moreover, as shown in FIGS. 85 and 86, there have been proposed the endoscope treatment apparatus and high-frequency treatment instrument in which the high-frequency incising instrument is attached to a side aperture 67 disposed in a hood 2 or an over tube 41. In the apparatus shown in FIGS. 85 and 86, to incise only the mucosa, there has been required a laborious operation comprising: finely adjusting the sucking operation of an endoscope 10; accurately and carefully controlling the height by which the mucosa is sucked up into the hood 2; and operating the endoscope so as to prevent the mucosa from being resected more deeply than necessary by excessive suction.

BRIEF SUMMARY OF THE INVENTION

The present invention has been developed noting the above-described circumstances, and objects thereof are as follows.

A first object is to provide a treatment apparatus for an endoscope in which a broad range of an affected area in a mucosa can be securely treated without leaving the affected area.

Another object is to provide a treatment apparatus for an endoscope in which only the mucosa can the securely treated without treating a part deeper than a mucosa lower layer.

A further object is to provide a treatment apparatus for an endoscope in which the broad range of the affected area in the mucosa can easily be treated in a short time.

To achieve the above-described objects, according to the present invention, there is provided a treatment apparatus for an endoscope, which is inserted into a body cavity together with a tip-end portion of the endoscope, and which treats a tissue in the body cavity. The treatment apparatus comprises: a base disposed in the vicinity of the tip-end portion of the endoscope; and an in-tissue inserting portion including a base end supported by the base, and a tip end which can be inserted into the tissue in the body cavity in a direction substantially parallel to the surface of the tissue, and extending to the tip end from the base end in a tapered shape. The in-tissue inserting portion has an inner side disposed in the vicinity of the surface of the tissue when inserted into the tissue. Furthermore, the treatment apparatus comprises: a high-frequency electrode for treating the tissue, which is supported by the base and disposed in the vicinity of the inner side of the in-tissue inserting portion; and a cable which supplies a high-frequency current to the high-frequency electrode from a high-frequency power supply apparatus disposed outside the body.

According to the treatment apparatus for the endoscope, for example, physiological saline is injected, a mucosa is separated from a muscle layer, and the in-tissue inserting portion is inserted under the mucosa via a small incised part incised using a high-frequency scalpel beforehand. When the high-frequency current is supplied to the high-frequency electrode for treating the tissue disposed in the vicinity of the inner side of the in-tissue inserting portion from the outside, only the necessary mucosa is incised. In this case, the in-tissue inserting portion protects parts other than the part to be incised from the influence of heat.

Moreover, according to the present invention, there is provided a treatment apparatus for an endoscope, comprising: a tubular member which is disposed in the vicinity of a tip-end portion of the endoscope, and includes a substantially cylindrical side wall; an aperture formed in the side wall; and an in-tissue inserting portion which is supported by the side wall of the tubular member and has a tip end projecting into the aperture and a tapered shape. The in-tissue inserting portion has an inner surface disposed in the vicinity of a surface side of a tissue when inserted into the tissue. The treatment apparatus further comprises: a high-frequency electrode for treating the tissue, which is disposed on an inner surface side of the in-tissue inserting portion; and a cable which supplies power to the high-frequency electrode from a high-frequency power supply apparatus disposed outside the body.

According to the treatment apparatus for the endoscope, a broad range of the affected area in the mucosa can be securely resected without leaving the affected area. Moreover, only the mucosa can securely be treated without treating a part deeper than the mucosa lower layer. Furthermore, the broad range of the affected area in the mucosa can easily be treated in a short time.

Furthermore, according to the present invention, there is provided a treatment apparatus for an endoscope, comprising: a tubular member which is disposed in the vicinity of a tip-end portion of the endoscope, and formed of an electrical insulator transparent and superior in heat resistance; and an in-tissue inserting portion which projects from the tubular member, and is formed of a material superior in heat resistance and electrical insulation. The in-tissue inserting portion has an inner surface disposed in the vicinity of a surface side of a tissue when inserted into the tissue. The treatment apparatus for the endoscope further comprises: a high-frequency incising instrument having an incising portion disposed at a predetermined distance from an inner surface of the in-tissue inserting portion; and a cable which supplies power to the incising portion of the high-frequency incising instrument from a high-frequency power supply apparatus disposed outside the body.

For the treatment apparatus for the endoscope, when the high-frequency incising instrument is disposed in a circumferential form, the mucosa of a lumen organ can be incised in a circular arc shape or an annular shape. When the instrument is disposed in an axial direction, not only the lumen organ but also the part of a forward/backward direction of the endoscope can be incised. Moreover, as the tubular member of the treatment apparatus, the hood whose tip end is obliquely cut to form an acute-angled edge can be used. In this case, the periphery of the affected area is incised beforehand using the high-frequency incising instrument, the edge of the instrument is inserted into the boundary between the mucosa and muscle layer, and the endoscope is moved forwards, so that the mucosa can be stripped. In this case, when the acute-angled edge is manufactured of a flexible material, only the relatively soft tissue of the boundary, having absorbed the physiological saline and become jellied, can be incised. Moreover, since the acute-angled edge is introduced into the body cavity through a guide tube, the mucosa is not damaged by the acute-angled edge during the inserting.

Therefore, according to the treatment apparatus for the endoscope, the periphery of the affected area of the mucosa can easily be incised in a short time. Moreover, the mucosa including the affected area can also easily be stripped in the short time. The time for performing the careful operation is short, the operator can therefore perform the treatment in a short time using less concentration than before, and both the operator and the patient have little fatigue. Moreover, since the method does not require skills as before, training does not require much time, and an apparatus and method usable by many operators can be obtained. Furthermore, for the incising before the stripping of the mucosa, after the positional relation between the incising instrument and mucosa is firmly grasped, the part of the mucosa to be incised can directly be observed with the endoscope while being incised, and the operator can incise the part with ease. During the mucosa stripping, the mucosa is physically stripped. This does not use high energy, and is therefore inexpensive as compared with an operation of incising and stripping the boundary with the high-frequency scalpel or a laser beam. Moreover, different from the high frequency or the laser, smoke or steam is not generated, the stripping can be continued without being interrupted, and the operator does not have to be irritated.

Furthermore, according to the present invention, there is provided a treatment apparatus for an endoscope, comprising: a tubular member which is disposed in the vicinity of a tip-end portion of the endoscope, and includes a substantially cylindrical side wall including an aperture; an in-tissue inserting portion having a tapered shape which projects toward the aperture; a deformable high-frequency electrode for treating a tissue, which is disposed at a predetermined distance from the in-tissue inserting portion inside the tubular member, and can abut the in-tissue inserting portion by an operation outside the body; and a cable which supplies a high-frequency current to the high-frequency electrode from a high-frequency power supply apparatus.

Additionally, according to the present invention, there is provided a treatment apparatus for an endoscope, comprising: a tubular member which is disposed in the vicinity of a tip-end portion of the endoscope, and includes a substantially cylindrical side wall; first and second apertures disposed in the side wall of the tubular member; first and second in-tissue inserting portions which are disposed in the tubular member, and have tapered shapes projecting toward the respective apertures; a first high-frequency electrode for treating a tissue, which is disposed on an inner surface side of the first in-tissue inserting portion, and extends in a plane substantially vertical to an axial direction of the tubular member; a second high-frequency electrode for treating the tissue, which is disposed on the inner surface side of the second in-tissue inserting portion, and extends substantially in the axial direction of the tubular member; and a cable which supplies the high-frequency current to the respective high-frequency electrodes.

Moreover, according to the present invention, there is provided a treatment apparatus for an endoscope, comprising: a base disposed in the vicinity of a tip-end portion of the endoscope; a first high-frequency electrode for treating a tissue, which is supported by the base, and extends in a first direction; a second high-frequency electrode for treating the tissue, which is supported by the base, and extends in a second direction different from the first direction; a high-frequency power supply apparatus disposed outside the body; first and second cables which are connected to the first and second high-frequency electrodes, and supply high-frequency currents to the first and second high-frequency electrodes from the high-frequency power supply apparatus; a switch apparatus which is disposed between the high-frequency power supply apparatus and the first and second cables, and selectively and electrically connects the high-frequency power supply apparatus to the first and second cables.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a front view of a valve, disposed in the over tube of the treatment apparatus of FIG. 1A, for preventing air leakage;

FIG. 6 is a perspective view showing the use state of the treatment apparatus of FIG. 1A;

FIG. 7 is an explanatory view showing the use state of the treatment apparatus of FIG. 1A;

FIG. 27 is a sectional view along line B—B in FIG. 26;

FIG. 29 is an enlarged longitudinal sectional view showing a portion C in FIG. 28;

FIG. 30 is an enlarged longitudinal sectional view of a portion D in FIG. 28;

FIG. 38 is a perspective view showing the hood portion of the treatment apparatus for the endoscope according to the eleventh embodiment of the present invention;

FIG. 39 is a longitudinal sectional view of a high-frequency knife for use in the treatment apparatus of FIG. 38;

FIG. 40 is a perspective view showing the use state of a laser probe;

FIG. 41 is a side view of another laser probe;

FIG. 42 is a side view of still another laser probe;

FIG. 74 is a longitudinal sectional view of the vicinity of hands operating the treatment apparatus shown in FIG. 73;

FIGS. 77A to 77E are explanatory views showing different examples of a shape of a sharp edge formed on an inner cylinder of a guide tube;

DETAILED DESCRIPTION OF THE INVENTION

Figure 1A:
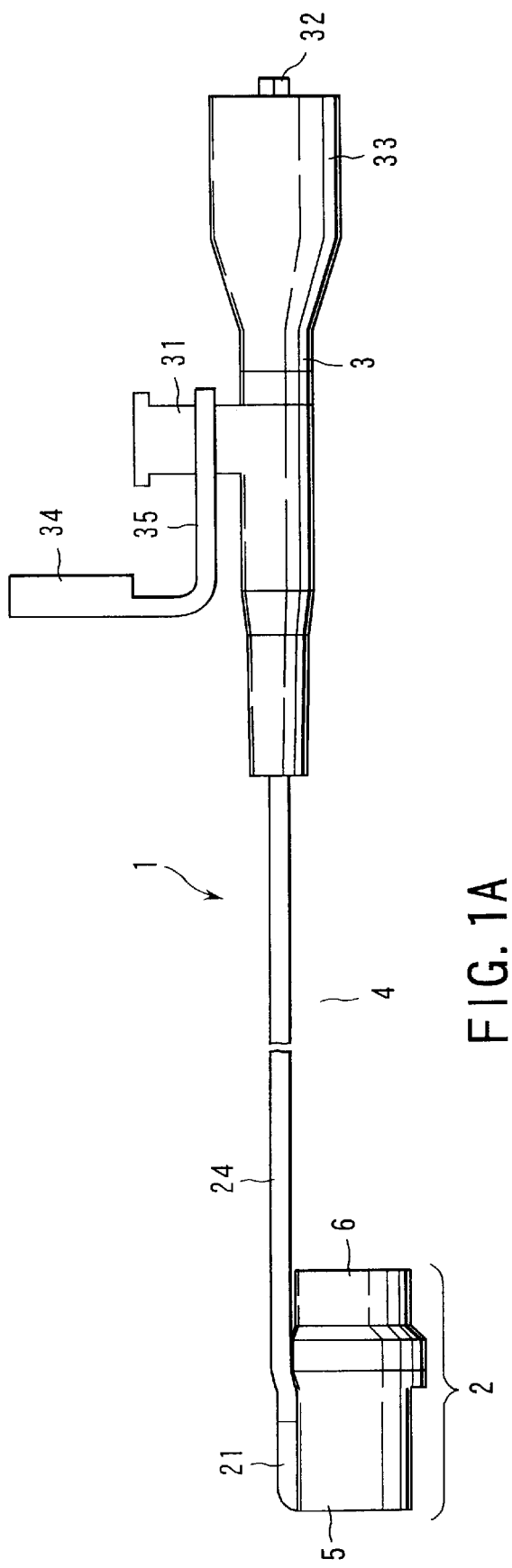
FIG. 1A is a whole side view of a treatment apparatus for an endoscope according to a first embodiment of the present invention.

Embodiments of the present invention will be described hereinafter with reference to the drawings. Additionally, in the respective embodiments described hereinafter, similar components are denoted with the same reference numerals.

(First Embodiment)

Figure 1B:
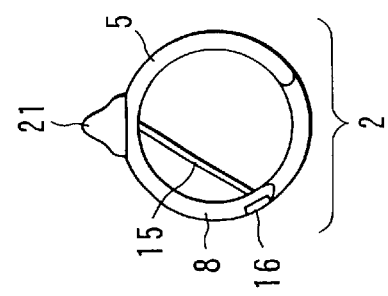
FIG. 1B is a front view of a tip-end portion of the treatment apparatus of FIG. 1A.

FIGS. 1 to 10 show a high-frequency incising apparatus 1 as a treatment apparatus for an endoscope according to a first embodiment. As shown in FIG. 1, the high-frequency incising apparatus 1 is constituted of a hood 2 inserted in a body, connector 3, and cable 4 for connecting the hood 2 to the connector 3.

Moreover, the hood 2 is constituted of a cylindrical main body portion 5 and attaching portion 6. The cylindrical main body portion 5 as a tubular member has a side wall formed in a substantially cylindrical shape of materials superior in electrical insulation, such as appropriate materials selected from a group including polycarbonate, polyamide, cycloolefin-based resin, polyether ketone, fluorine resin and norbornene resin. Additionally, as the material of the cylindrical main body portion 5, particularly a resin superior in transparency and high-frequency resistance such as the norbornene resin is more preferable. The cylindrical main body portion 5 preferably has an outer diameter of 8 mm to 18 mm, and inner diameter of 6 mm to 16 mm.

Furthermore, the attaching portion 6 of the hood 2 is formed by a soft cylindrical member, and examples of a soft material of the portion include rubber materials such as silicone rubber, polyvinyl chloride (PVC), and thermoplastic elastomer. The attaching portion 6 has an inner diameter such that the portion can detachably be attached to a tip-end portion 12 in an inserting portion 11 of an endoscope 10 described later.

Figure 2:
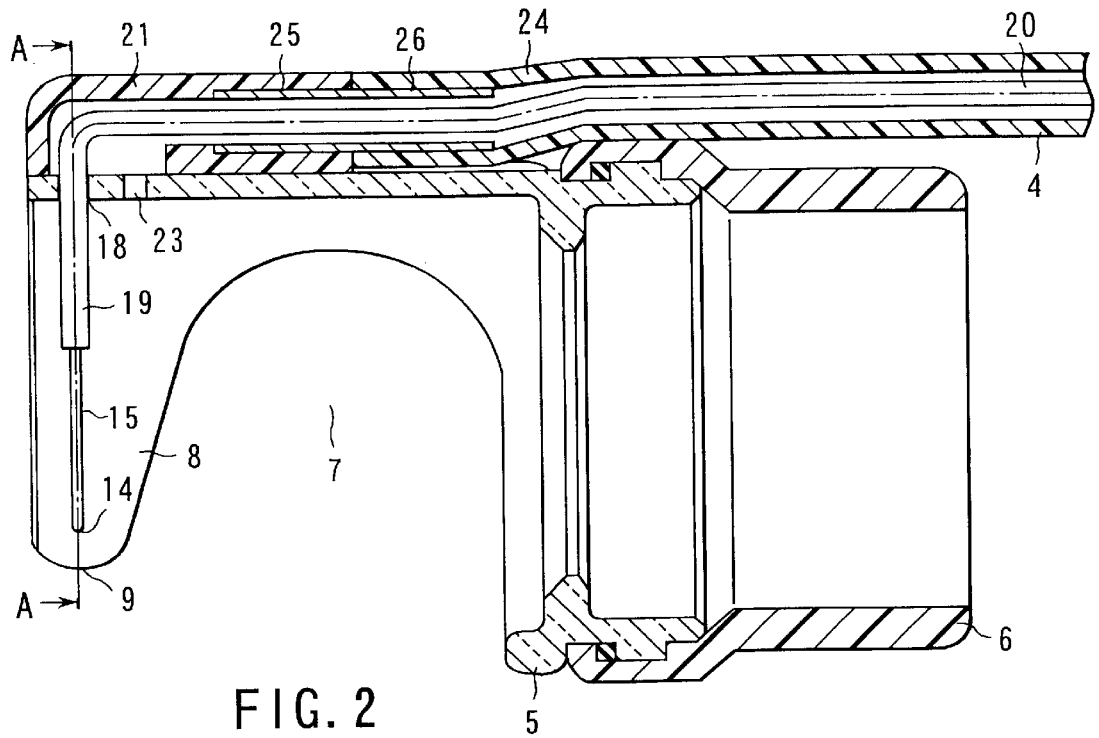
FIG. 2 is a longitudinal sectional view of the vicinity of a hood of the treatment apparatus for the endoscope shown in FIG. 1A.

As shown in FIG. 2, the cylindrical main body portion 5 of the hood 2 includes a cutout portion 7 as an aperture opened sideways, and an in-tissue inserting portion 8 disposed in a tip-end side portion. The cylindrical main body portion 5 acts as a base for supporting the in-tissue inserting portion. For the cutout portion 7, as a remaining aperture size excluding the in-tissue inserting portion 8, a width is preferably in the range of 4 mm to 20 mm, and a length is in the range of 4 mm to 20 mm.

Moreover, the in-tissue inserting portion 8 is formed to be elongate, and has a tapered shape pointed toward a tip end, and a tip end 9 is formed to be round. As described later, the in-tissue inserting portion 8 is inserted, for example, under a mucosa of a lumen organ, and substantially parallel to the surface of the mucosa, that is, a surface exposed to an inner space of the lumen organ. The portion has an inner side disposed in the vicinity of the surface of the mucosa, and an outer side disposed in the vicinity of a muscle layer. The in-tissue inserting portion 8 preferably has a thickness in the range of 0.5 mm to 2 mm in a base end supported by the cylindrical main body portion 5, that is, a root portion, and in the range of 0.1 mm to 0.5 mm in the tip-end portion. The in-tissue inserting portion 8 preferably has a width in the range of 2 mm to 10 mm in the root portion, and in a range of 1 mm to 4 mm in the tip-end portion.

Additionally, the in-tissue inserting portion 8 may have a shape, for example, of a flat nail or a spatula as long as the portion projects in an elongated shape, or may have an elliptical, quadrangular, triangular or any shape. Moreover, the in-tissue inserting portion 8 does not have to be integral with the cylindrical main body portion 5, and may separately be formed and bonded or attached to the cylindrical main body portion 5. In this case, the in-tissue inserting portion 8 may be formed of a material other than that of the cylindrical main body portion 5. Furthermore, the shape of the in-tissue inserting portion 8 is not limited to the flat spatula form, and a thin rod shape may be used. Additionally, the radius of curvature the in-tissue inserting portion 8 does not have to be the same as that of the cylindrical main body portion 5, and may be larger or smaller than that of the cylindrical main body portion 5.

Figure 3:
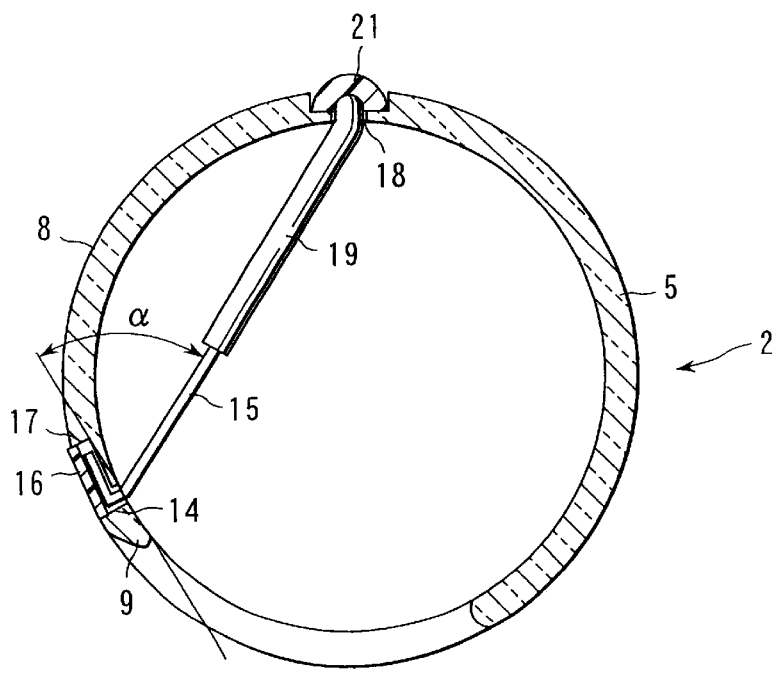
FIG. 3 is a sectional view along line A—A in FIG. 2.

A small hole 14 is made in the vicinity of the tip end of the in-tissue inserting portion 8. One end of an incision line 15 formed of a metal wire superior in conductivity, such as stainless steel and gold is inserted into the hole 14 from the inside, and the tip end of the incision line 15 is bent as shown in FIG. 3. The bent tip-end portion of the incision line 15 is covered with a wire cover portion 16 attached to the hole 14 from the outside, and the tip-end portion is bonded to the in-tissue inserting portion 8 via an adhesive 17. That is, one end of the incision line 15 is fixed to the vicinity of the tip end of the in-tissue inserting portion 8. Moreover, the incision line 15 is extended to an optional point of the inner surface of the cylindrical main body portion 5 as the tubular member from the inner surface of the in-tissue inserting portion 8 in a chord form, and constitutes a high-frequency electrode for treating the tissue. The hole 14 is positioned in a place of 0.5 mm to 3 mm from the tip end of the in-tissue inserting portion 8. An outer diameter of the incision line 15 is in the range of 0.05 mm to 3 mm, preferably 0.15 mm to 0.3 mm.

The wire cover portion 16 may be connected to the in-tissue inserting portion 8 not by adhesion but by other bonding methods such as thermal welding. The wire cover portion 16 is formed by the material superior in high-frequency resistance and electrical insulation similarly as the cylindrical main body portion 5.

As shown in FIG. 3 (A—A section of FIG. 2), one end of the incision line 15 is fixed to the tip end of the in-tissue inserting portion 8, and the other-end portion thereof is passed through a side hole 18 formed in the cylindrical main body portion 5. Therefore, as shown in FIG. 3, the incision line 15 is extended in a bow string form in the cylindrical main body portion 5, when the hood 2 is seen in the axial direction. Moreover, an angle α of the incision line 15 extended in the string form with respect to an inscribed line is in the range of 0° to 90°.

Moreover, in the cylindrical main body portion 5, an electrical insulation coat 19 is peeled from the incision line 15 in a region of a certain predetermined distance from a contact position with the in-tissue inserting portion 8, and the line is exposed to the outside. A length of the exposed portion of the incision line 15 is in the range of 1 mm to 10 mm. The surface of the exposed portion of the incision line 15 is coated/treated, for example, with a thin fluoride coat in order to prevent burn. Additionally, for the electrical insulation coat 19, for example, a non-contractible tube of a fluorine resin may be coated. Moreover, the thickness of the electrical insulation coat 19 is preferably of the order of 0.05 mm to 1 mm.

The portion of the incision line 15 coated with the electrical insulation coat 19 is formed as a coated line 20. The coated line 20 is passed through the side hole 18 of the cylindrical main body portion 5, bent, guided to a hand side through the cable 4, and connected to a high-frequency power supply (not shown).

Moreover, the coated line 20 is covered from the outside with a separate wire presser 21 superior in electrical insulation outside the cylindrical main body portion 5. The wire presser 21 may not be separate from the cylindrical main body portion 5 and may be integral therewith. Furthermore, a small hole 23 is formed in the portion of the cylindrical main body portion 5 covered with the wire presser 21. The small hole 23 is connected into the cable 4 as described later.

As shown in FIG. 2, the cable 4 has a tube sheath 24, and the tube sheath 24 is formed of the material superior in electrical insulation such as the fluorine resin. The tube sheath 24 has an inner diameter and thickness which are sufficient for passing and protecting the coated line 20. For a size, the inner diameter is preferably in the range of 0.5 mm to 2 mm, and the thickness is of the order of 0.1 mm to 1 mm.

The tube sheath 24 is connected to a cable insertion port 25 formed in the end of the wire presser 21 on the hand side. As shown in FIG. 2, a stainless steel pipe 26 is fit in the cable insertion port 25 to connect the wire presser 21 to the tube sheath 24. The pipe 26 has an inner diameter sufficient for passing the coated line 20. The material of the pipe 26 is not limited to stainless steel as long as it has a pipe shape functioning as the connection.

The tube sheath 24 extending from the connected portion with the wire presser 21 extends to the connector 3, and is connected to the connector 3. Moreover, the coated line 20 is passed through the pipe 26 and tube sheath 24 via the cable insertion port 25 of the wire presser 21, and is connected to the connector 3. Therefore, a current flowing through the coated line 20 does not leak into the body from an unnecessary portion.

As shown in FIG. 1, the connector 3 of the high-frequency incising apparatus 1 includes a water supply cock 31, connection terminal 32 and terminal cover portion 33. A cap 34 is detachably attached to the water supply cock 31. The cap 34 has a support piece 35, and the support piece 35 is wound around and attached to the water supply cock 31. Therefore, even when the cap 34 is detached from the port of the water supply cock 31, the cap 34 does not drop from the connector 3.

Moreover, water injected via the port of the water supply cock 31 flows inside the cable 4, and is discharged into the hood 2 via the small hole 23 formed in the cylindrical main body portion 5. The inside of the cable 4 can be cleaned with the supplied water.

The connection terminal 32 is electrically connected to the coated line 20. Moreover, a portion of the connection terminal 32 is covered with the terminal cover portion 33, and an operator who touches the connection terminal 32 is prevented from getting an electric shock during power supply.

An over tube 41 for guiding the inserting portion 11 of the endoscope 10 with the high-frequency incising apparatus for the endoscope 1 attached thereto into the body will next be described with reference to FIGS. 4 and 5.

The over tube 41 is constituted of a tube main body 43, and an endoscope insertion port member 44 connected to the base end of the tube main body 43. The tube main body 43 is formed of a material selected from polyurethane, vinyl chloride, and preferable resins including the fluorine resin. The main body is more preferably formed of a material superior in slip properties, such as the fluorine resin for ease of insertion into the body and ease of rotation of the endoscope 10. Moreover, the outer diameter of the over tube 41 is in the range of 12 mm to 20 mm, particularly preferably 15 mm to 18 mm. The inner diameter of the over tube 41 is not limited as long as the inserting portion 11 of the endoscope 10 can be inserted through the tube.

A valve 45 for preventing air leakage is fitted in the endoscope insertion port member 44 of the over tube 41 as shown in FIG. 5. A hole 46 for passing the inserting portion 11 of the endoscope 10 is made in the middle of the valve 45, and a plurality of cuts 47 are made around the hole 46 to facilitate the inserting of the inserting portion 11 of the endoscope 10. The cuts 47 are radially arranged while one end of each cut is connected to the hole 46. The number of cuts 47 is not limited to the number of cuts shown in FIG. 5.

Moreover, a circular small hole 48 is disposed on an outer end of each cut 47 in a radial direction. When the small holes 48 are disposed in the radial outer ends of the cuts 47, the valve 45 can be prevented from being torn from the portions of the cuts 47 during the inserting of the inserting portion 11 of the endoscope 10 into the middle hole 46. Additionally, as long as the function of preventing the valve 45 from being torn can be obtained, the shape of the small hole 48 is not limited to the circular shape, and a triangular, quadrangular, or any other shape may be used.

Figure 8:
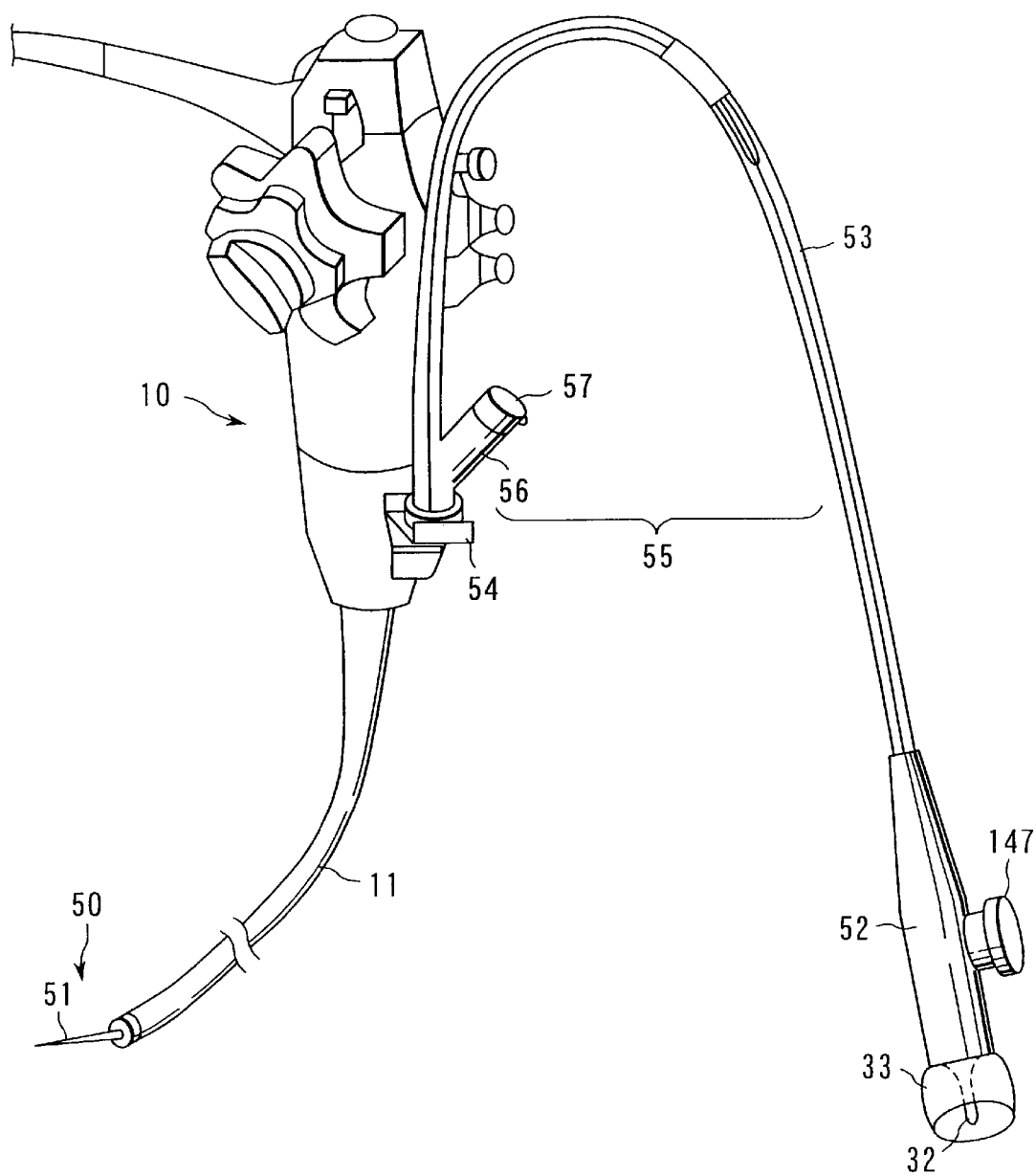
FIG. 8 is a perspective view of the use state in which a needle-shaped high-frequency treatment apparatus for use in forming a small incision in a mucosa is inserted in the endoscope.

A constitution of a needle-shaped high-frequency incising apparatus (high-frequency incising instrument) 50 for use in forming the small incision beforehand during the inserting of the in-tissue inserting portion 8 of the high-frequency incising apparatus for the endoscope 1 under the mucosa will next be described with reference to FIG. 8.

The high-frequency incising apparatus 50 is constituted of: an incising portion 51 on a tip-end side; a connector 52 on a hand side; a coated line 53 for electrically connecting the incising portion 51 to the connector 52; and a protective sheath 55 with which the coated line 53 is covered between a treatment instrument insertion port 54 of the endoscope 10 and the connector 52.

After the coated line 53 connected to the incising portion 51 is inserted through the protective sheath 55, the line is inserted into the endoscope 10 via the treatment instrument insertion port 54 of the endoscope 10. After the line is inserted into the endoscope 10, the protective sheath 55 is fixed to the treatment instrument insertion port 54 and connector 52, and protects the coated line 53. A branched portion 56 is disposed on the tip end of the protective sheath 55, and another treatment apparatus for the endoscope can simultaneously be inserted into the endoscope 10 via an aperture 57 of the branched portion 56 together with the coated line 53 via the treatment instrument insertion port 54. The connector 52 of the high-frequency incising apparatus 50 can be connected to the high-frequency power supply (not shown).

An action of the high-frequency incising apparatus 1 of the above-described embodiment will next be described. First, as shown in FIG. 6, the hood 2 is attached to the tip-end portion 12 in the inserting portion 11 of the endoscope 10.

Thereafter, medical tapes 156 are used in several positions of the inserting portion 11 of the endoscope 10 to fix the cable 4.

Figure 4:
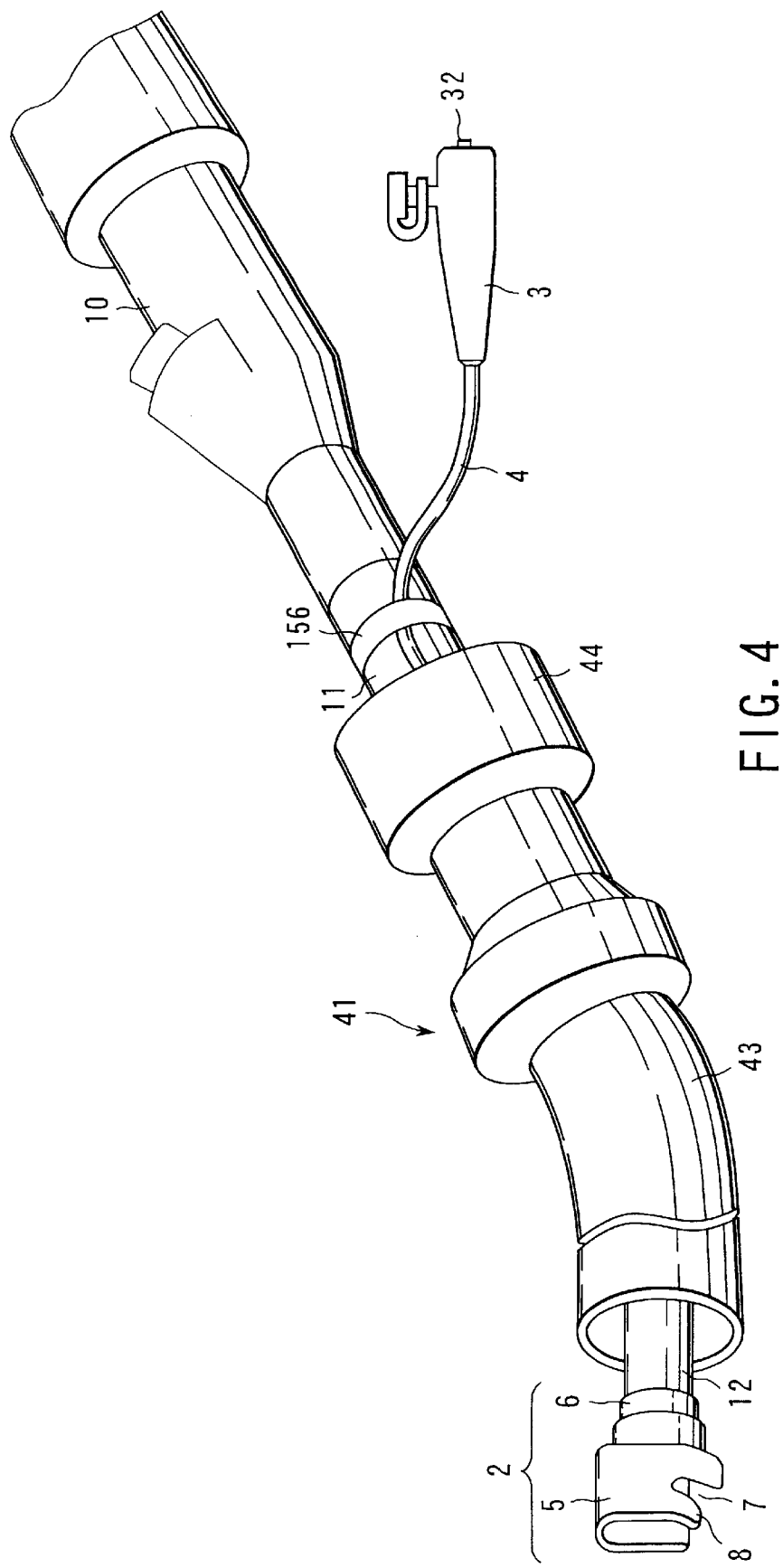
FIG. 4 is a perspective view of a use state of an inserting portion of the endoscope with the treatment apparatus of FIG. 1A attached thereto and an over tube for guiding the inserting portion of the endoscope into a body.

Thereafter, as shown in FIG. 4, the inserting portion 11 of the endoscope 10 is inserted through the over tube 41. Moreover, the connection terminal 32 of the connector 3 is connected to the high-frequency power supply (not shown) via a power cord (not shown).

Subsequently, after the inserting portion 11 of the endoscope 10 and the over tube 41 are inserted through the body cavity, only the inserting portion 11 of the endoscope 10 is moved to a target portion of the lumen organ such as esophagus, duodenum, small intestine, and large intestine.

Next, as shown in FIG. 7, a needle for syringe 61 is used to inject physiological saline under the mucosa of the lumen organ, a connective tissue 64 is allowed to absorb the physiological saline between a mucosa 62 and muscle layer 63, and the connective tissue 64 is swollen or expanded. Then, the mucosa 62 is detached from the muscle layer 63, expanded in a bump shape, stretched, and easily cut.

Subsequently, the high-frequency incising apparatus 50 is inserted into a lumen through the endoscope 10, and the high-frequency incising apparatus 50 forms a small incision 65 in the mucosa 62. In this case, since the physiological saline is injected and the mucosa 62 is expanded in the bump shape, and even when the needle-shaped high-frequency incising apparatus 50 is used to form the small incision 65 in the mucosa 62, the muscle layer 63 is not damaged.

Figure 9:
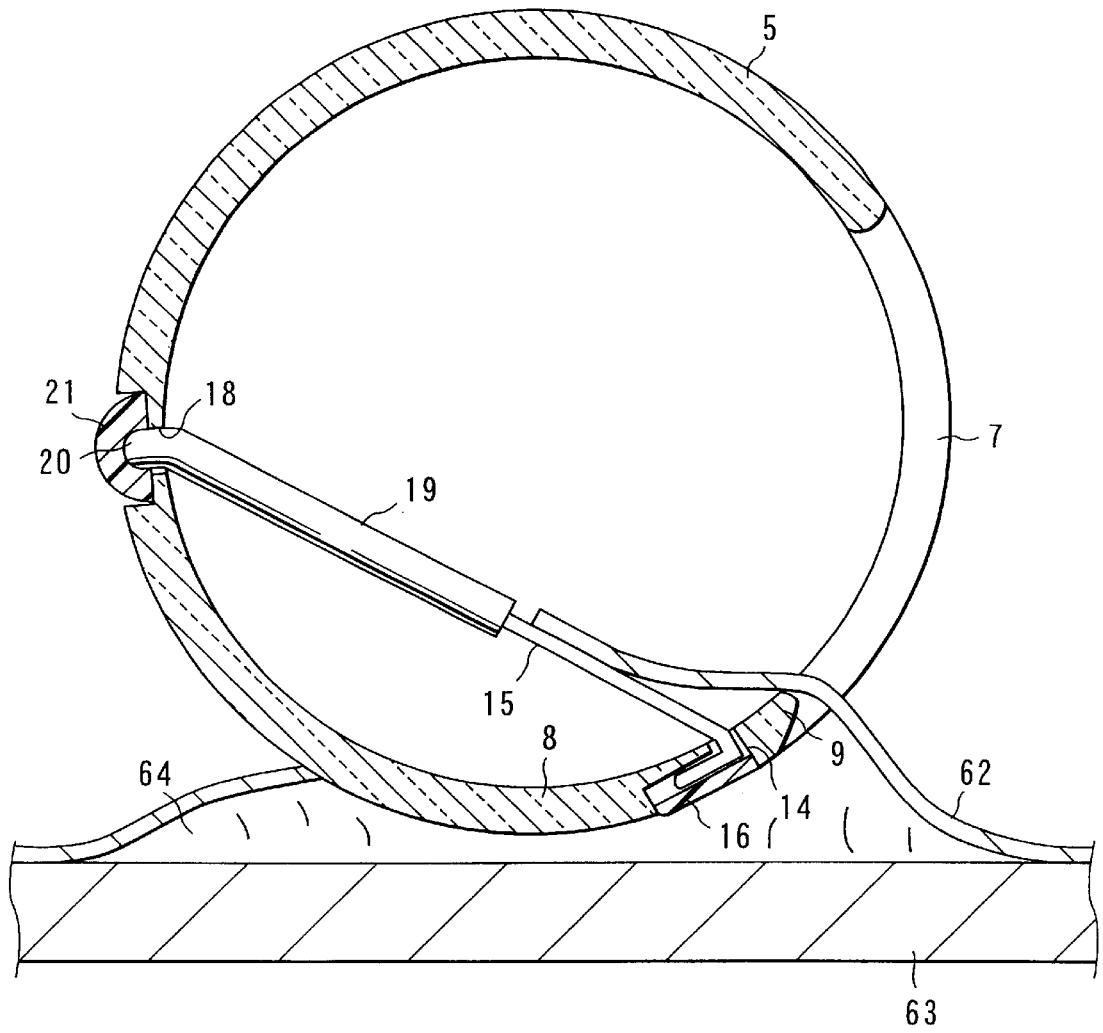
FIG. 9 is an explanatory view showing the use state of the treatment apparatus.

Subsequently, the in-tissue inserting portion 8 of the hood 2 is positioned above the small incision 65 by an operation of moving the endoscope 10 forwards/backwards or an angle operation of the endoscope 10, and the inserting portion 11 of the endoscope 10 is rotated. Then, as shown in FIG. 9, the in-tissue inserting portion 8 is slipped into the small incision 65 formed by the high-frequency incising apparatus 50 via the tip end 9.

In this case, a sucking operation of the endoscope 10 is performed while an operating portion of the endoscope 10 is rotated. Then, the inserting portion 11 of the endoscope 10 also rotates, and the in-tissue inserting portion 8 easily goes under the mucosa 62. If it is still difficult to insert the portion, the operation may comprise: picking up the mucosa 62 with other forceps; and bringing up the mucosa 62 while inserting the tip end 9 of the in-tissue inserting portion 8 under the mucosa 62.

Here, since the tip end 9 of the in-tissue inserting portion 8 is formed to be round, the backside of the mucosa 62 or the muscle layer 63 is not damaged. Additionally, the portion is not passed through the muscle layer 63. Moreover, since the width and thickness of the in-tissue inserting portion 8 decrease toward the tip end thereof, and the installation angle α of the incision line 15 is in the range of 0° to 90°, the portion is easily inserted into the lower layer of the mucosa 62.

Subsequently, after the in-tissue inserting portion 8 slips into the small incision 65, the incision line 15 is brought into close contact with the mucosa 62. Thereafter, when power is supplied to the incision line 15, as shown in FIGS. 6 and 9, the part of the mucosa 62 closely adhering to the incision line 15 is linearly cut. Additionally, even when the mucosa 62 contacts the portion coated with the electrical insulation coat 19, the mucosa 62 cannot be cut by the portion.

Figure 10:
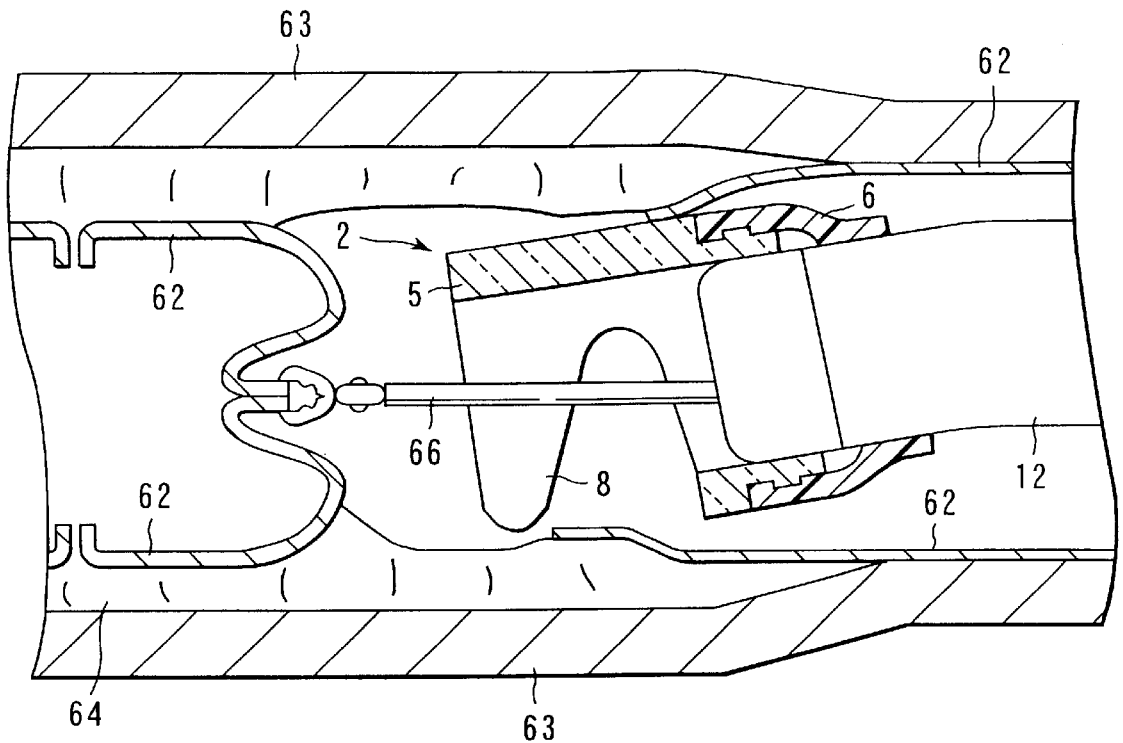
FIG. 10 is an explanatory view of a state in which the mucosa is grasped.

When the above-described operation is repeated, the whole circumference of the inner wall of the lumen organ is incised at two places on a rear side and alley side of the affected area. Thereafter, as shown in FIG. 10, the physiological saline is injected between two incised parts, and the mucosa 62 of the affected area is completely separated from the muscle layer 63. Furthermore, subsequently, the mucosa 62 of the affected area is grasped with grip forceps 66 while the mucosa 62 of the affected area is stripped/collected.

As described above, according to the high-frequency incising apparatus 1 of the present embodiment, as shown in FIG. 9, the incision line 15 closely adheres to the backside of the mucosa 62, and the mucosa is incised toward the surface from the backside. Additionally, since the in-tissue inserting portion 8 is positioned between the incision line 15 and muscle layer 63, the muscle layer 63 is not damaged by the incision line 15. The in-tissue inserting portion 8 not only supports and guides the incision line 15 but also functions as a shield for preventing an unintended part from being influenced.

Moreover, since the in-tissue inserting portion 8 slips into the mucosa 62, the whole portion of the exposed incision line 15 easily and closely adheres to the mucosa 62, and it is possible to incise a long distance at one time. As a result, the mucosa 62 of the affected area can securely and easily be removed.

Furthermore, since the high-frequency incising apparatus 50 is used, the part of the mucosa 62 in a broad range can be removed at one time without being left.

Moreover, both the part of the mucosa 62 to be incised and the incision line 15 are shown in an endoscope image while the incising operation is carried out. Therefore, a quick method can be executed.

(Second Embodiment)

Figure 11:
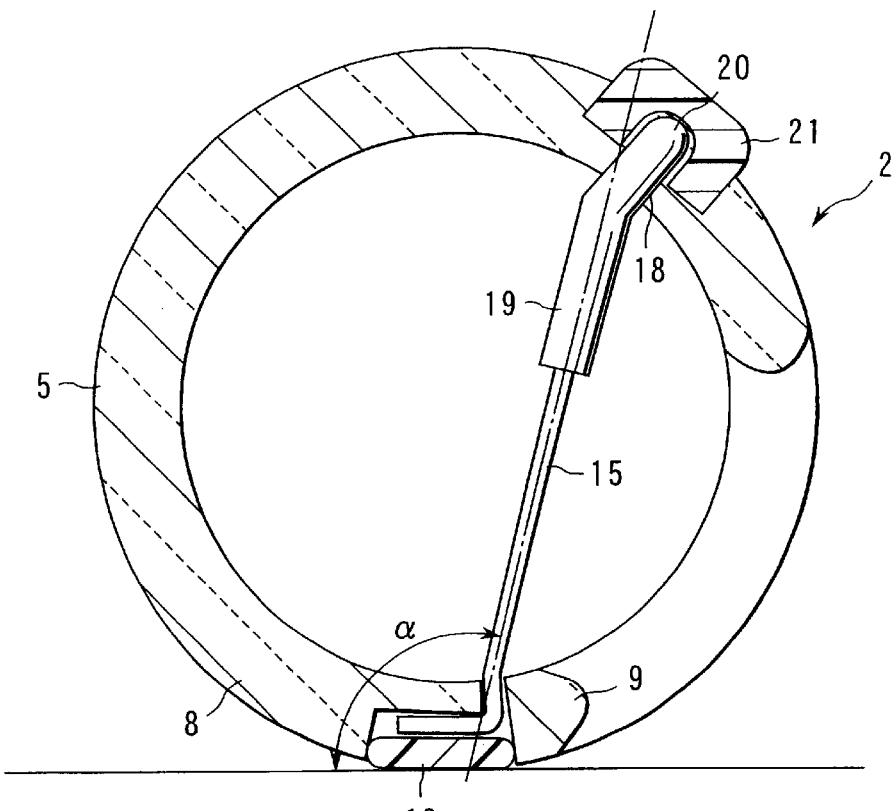
FIG. 11 is a transverse sectional view of a hood portion of the high-frequency treatment apparatus for the endoscope according to a second embodiment of the present invention.
Figure 12:
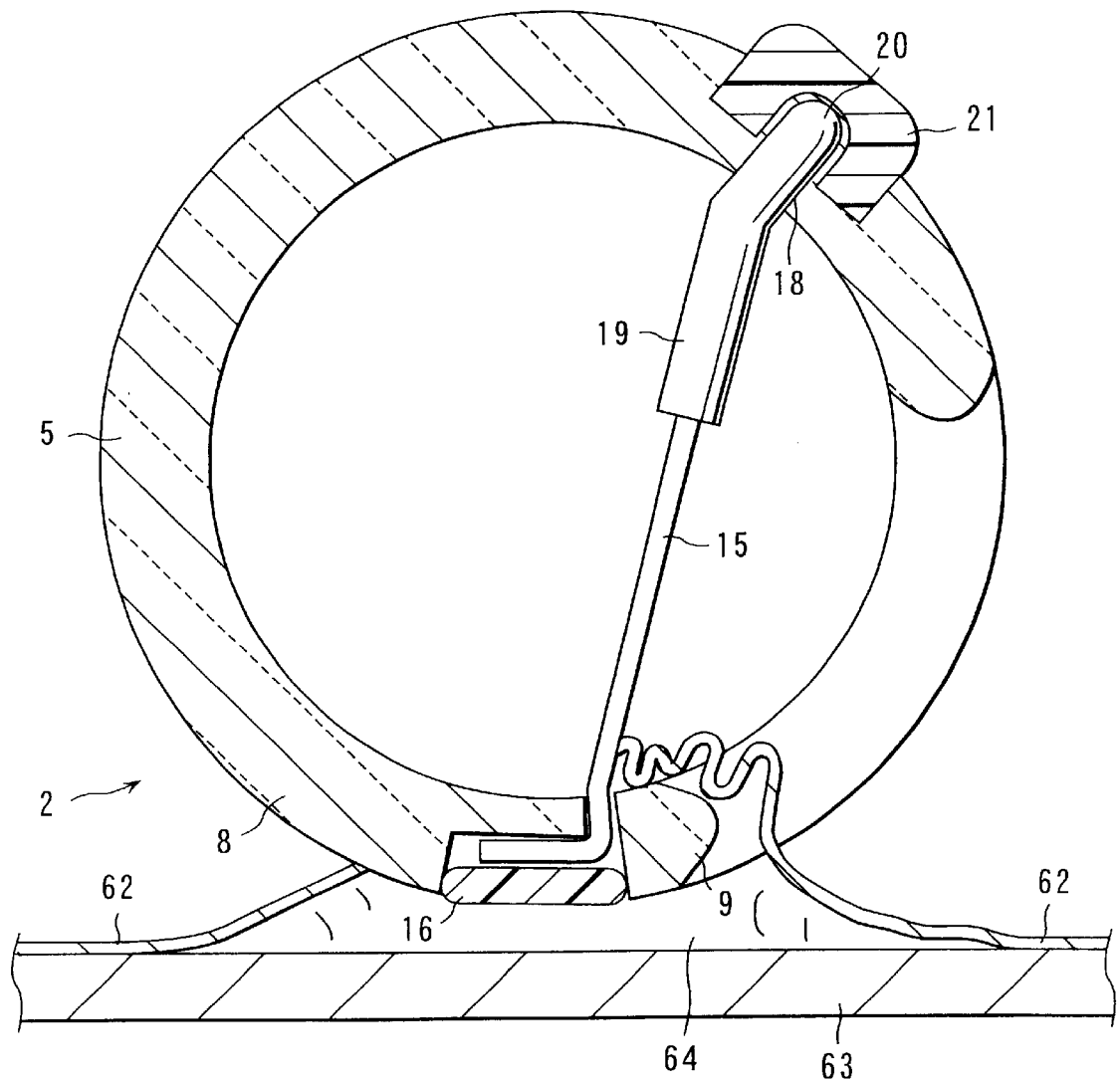
FIG. 12 is a transverse sectional view of the hood portion showing the use state of the treatment apparatus shown in FIG. 11.

FIGS. 11 and 12 show the treatment apparatus for the endoscope according to a second embodiment. In the second embodiment, as shown in FIG. 11, a wire angle α is in the range of 90° to 180°. The other portions are the same as those of the first embodiment.

In the first embodiment, the incision line 15 is slipped under the mucosa, and mucosa is resected from the backside. In the second embodiment, as shown in FIG. 12, the in-tissue inserting portion 8 is slipped under the mucosa 62, the incision line 15 is closely attached to the mucosa 62 from the side surface of the mucosa or from above, and the mucosa is resected. That is, since the wire angle α is in the range of 90° to 180°, and when the in-tissue inserting portion 8 is inserted under the mucosa 62, and the endoscope 10 is rotated around the axis, the incision line 15 can strongly and closely adheres to the mucosa 62, and the incising is facilitated. Additionally, since a contact area of the mucosa 62 and incision line 15 is reduced, power is easily concentrated, and the incising is facilitated. Furthermore, the part to be cut is checked while the part can be incised. Therefore, the method can be securely carried out.

(Third Embodiment)

FIGS. 13 to 16 show the treatment apparatus for the endoscope according to a third embodiment. The basic constitution of the high-frequency incising apparatus for the endoscope of the third embodiment is the same as that of the above-described first embodiment.

Figure 13:
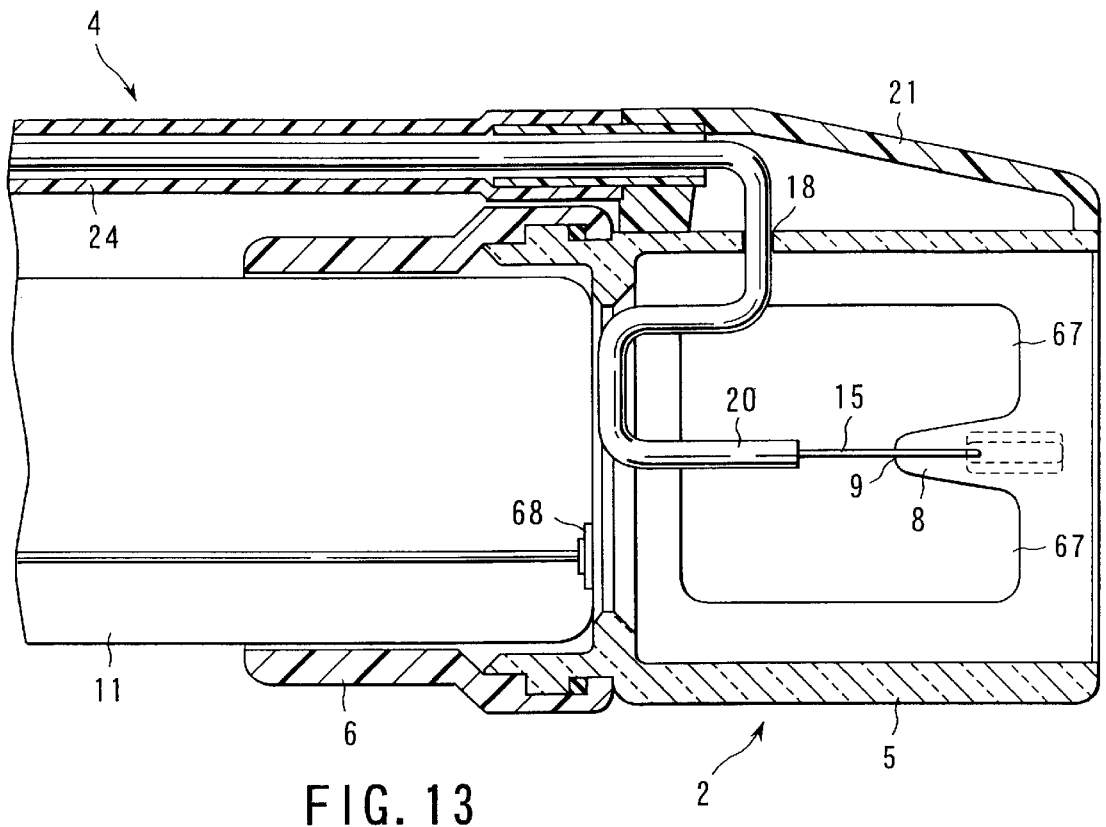
FIG. 13 is a longitudinal sectional view of the hood portion of the high-frequency treatment apparatus for the endoscope according to a third embodiment of the present invention.
Figure 14:
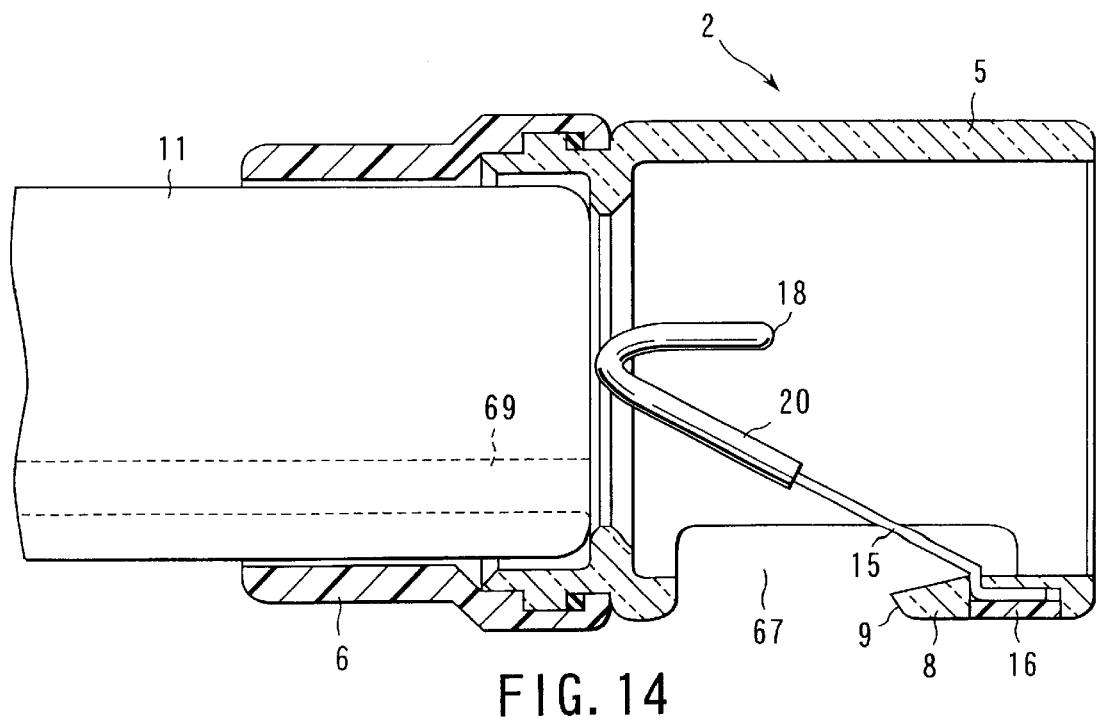
FIG. 14 is a transverse sectional view of the hood portion of the treatment apparatus shown in FIG. 13.

In the third embodiment, as shown in FIG. 13, a side aperture 67 is opened in the side wall of the hood 2, and the incision line 15 and in-tissue inserting portion 8 are disposed in the axial direction in the side aperture 67. Both the incision line 15 and the in-tissue inserting portion 8 extend and project to the base end from the tip end of the side aperture 67.

Moreover, the side aperture 67 has a substantially U-shaped aperture. However, the opening of the side aperture 67 may have an elliptical, circular, or triangular shape as long as the in-tissue inserting portion 8 projects in the middle. Moreover, the size of the aperture shape of the side aperture 67 has a width of 4 mm to 20 mm, and a length of 4 mm to 20 mm.

Furthermore, to further facilitate the inserting of the in-tissue inserting portion 8 under the mucosa in the third embodiment, the tip end of the portion is sharpened so as to reduce the width and thickness as compared with the above-described first and second embodiments.

Moreover, the thickness of the in-tissue inserting portion 8 is in the range of 0.5 mm to 2 mm in the base-end portion, and 0.05 mm to 0.5 mm on the tip-end side. Furthermore, the width of the in-tissue inserting portion 8 is in the range of 1 mm to 5 mm in the base-end portion, and 0.5 mm to 3 mm on the tip-end side.

The coated line 20 extends in the axial direction from the contact position of the incision line 15 and in-tissue inserting portion 8, and is then bent in the vicinity of the tip-end portion 12 of the endoscope 10 in a direction in which the port of the observation window (objective lens) 68 and treatment instrument inserting passage 69 of the endoscope 10 is not obstructed. Moreover, the coated line is disposed to obstruct the front portion of a lighting winding 70 as little as possible. This bending way and arrangement are not limited to FIGS. 13 and 14.

The action of the high-frequency incising apparatus for the endoscope of the third embodiment will next be described. The treatment before forming the small incision 65 is the same as that of the above-described first embodiment.

Figure 15:
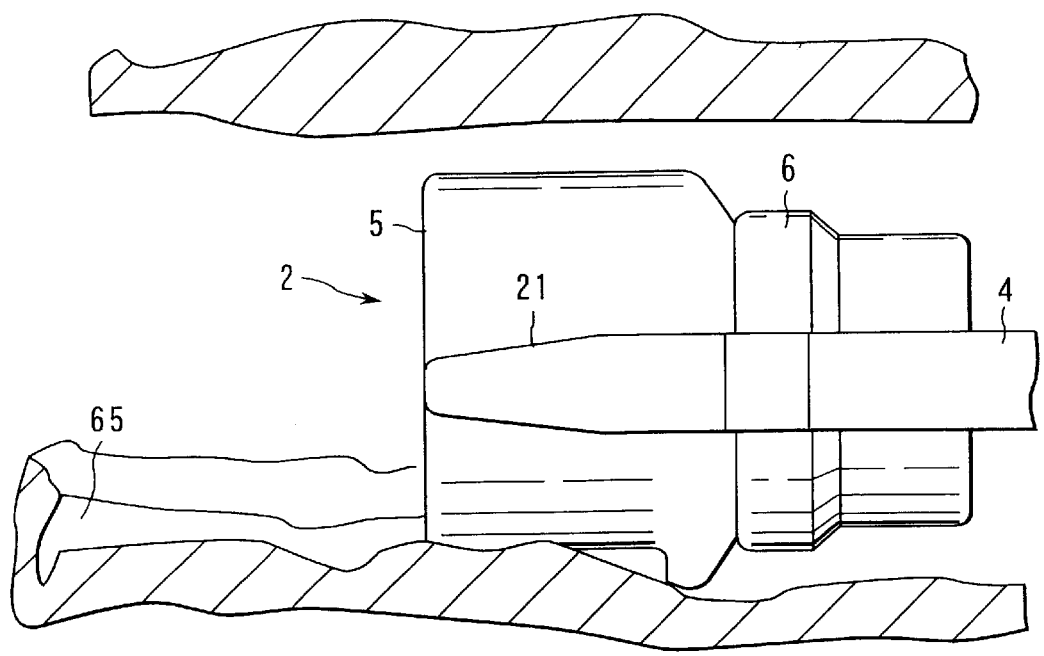
FIG. 15 is an explanatory view showing the use state of the treatment apparatus shown in FIG. 13.
Figure 16:
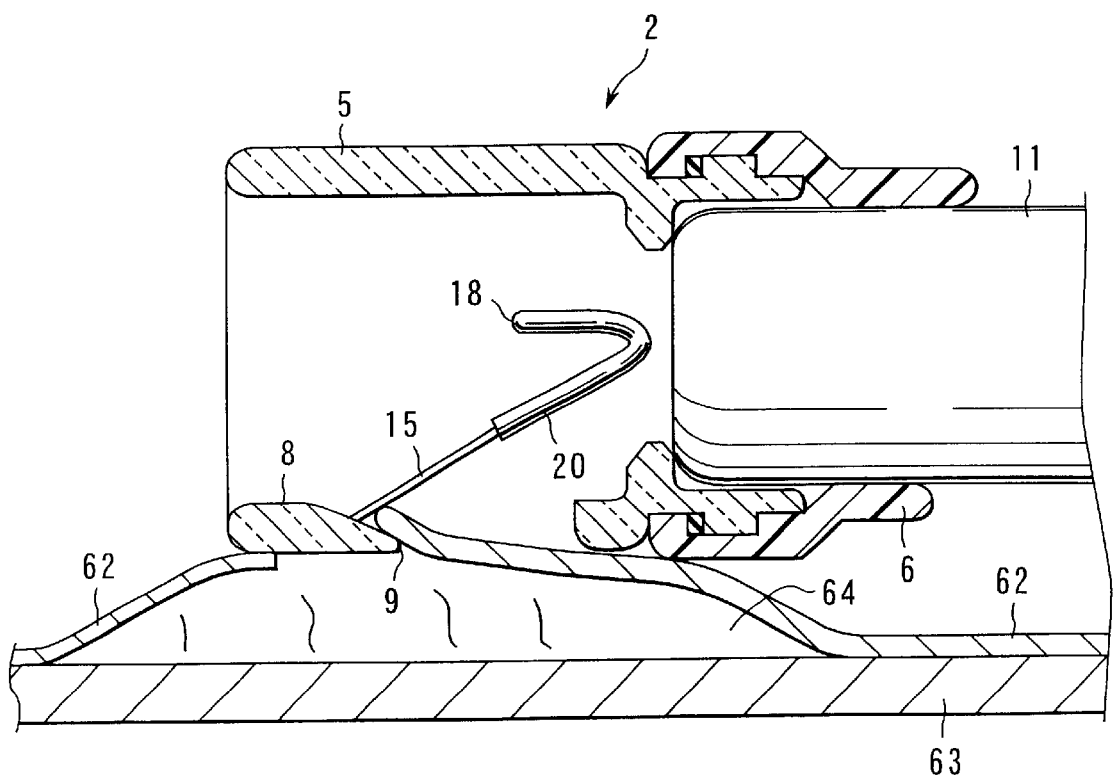
FIG. 16 is a transverse sectional view of the hood portion showing the use state of the treatment apparatus shown in FIG. 13.

As shown in FIGS. 15 and 16, the in-tissue inserting portion 8 is inserted under the mucosa 62, and is further constantly inserted under the mucosa 62 while the endoscope 10 is pulled forwards. In this manner, the mucosa 62 can linearly and continuously be incised.

In addition to the above-described operation, two circular arc incisions are formed by the incising instrument for incising the mucosa circumferentially, as in other embodiments, so that a rectangular incision is formed. Of course, the order of the circular arc incising and linear incising is not limited.

After the mucosa 62 is incised in the rectangular shape in this manner, the physiological saline is injected into the corresponding part, and the mucosa is separated from the muscle layer 63. Thereafter, the part is stripped/collected by the grip forceps.

According to the high-frequency incising apparatus for the endoscope of the third direction, it is possible to incise the mucosa in the axial direction, and it is therefore possible to incise the mucosa 62 in the rectangular shape. Moreover, the incising can be securely carried out with a simple method.

(Fourth Embodiment)

Figure 17:
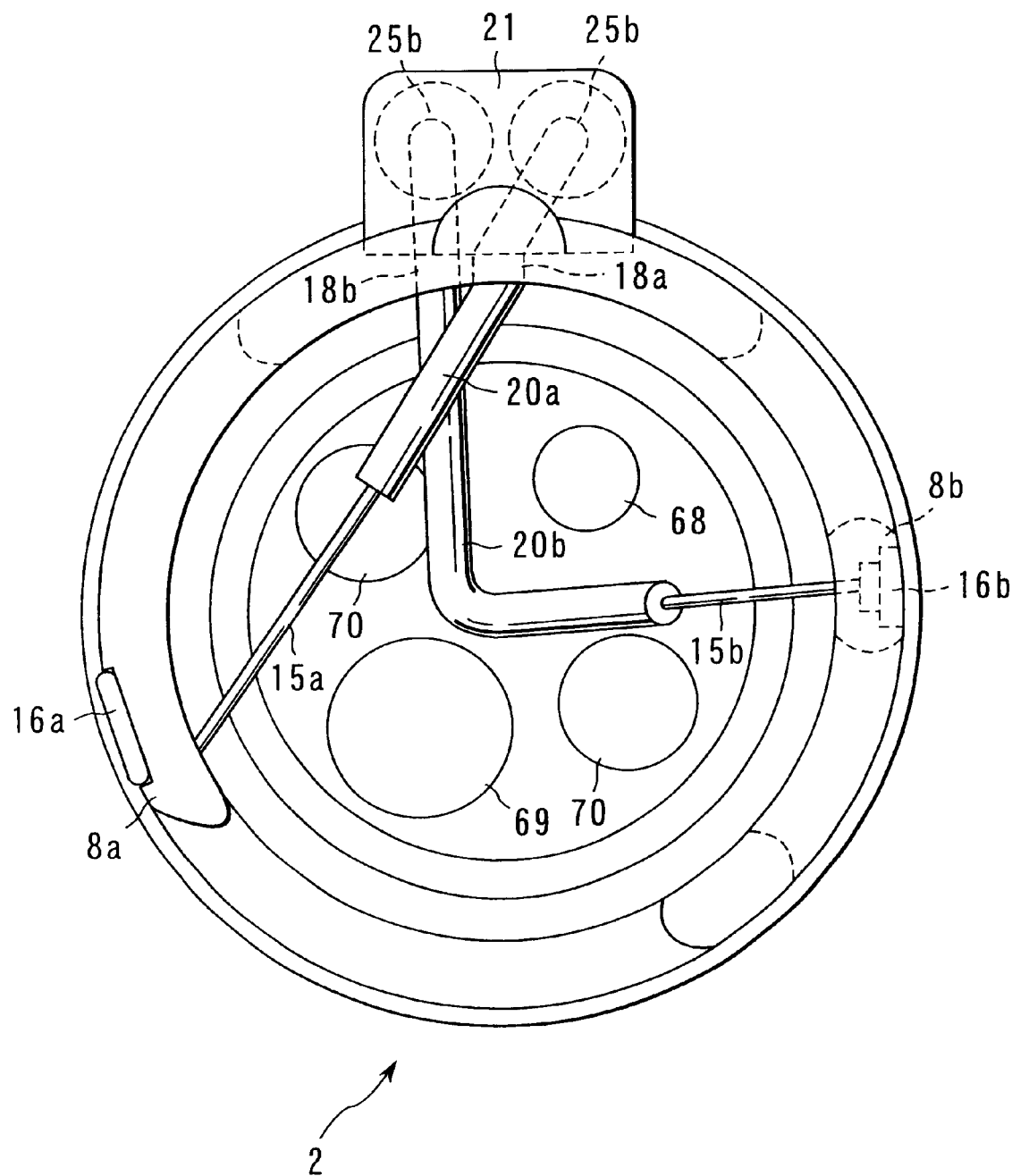
FIG. 17 is a front view of the hood portion of the high-frequency treatment apparatus for the endoscope according to a fourth embodiment of the present invention.
Figure 18:
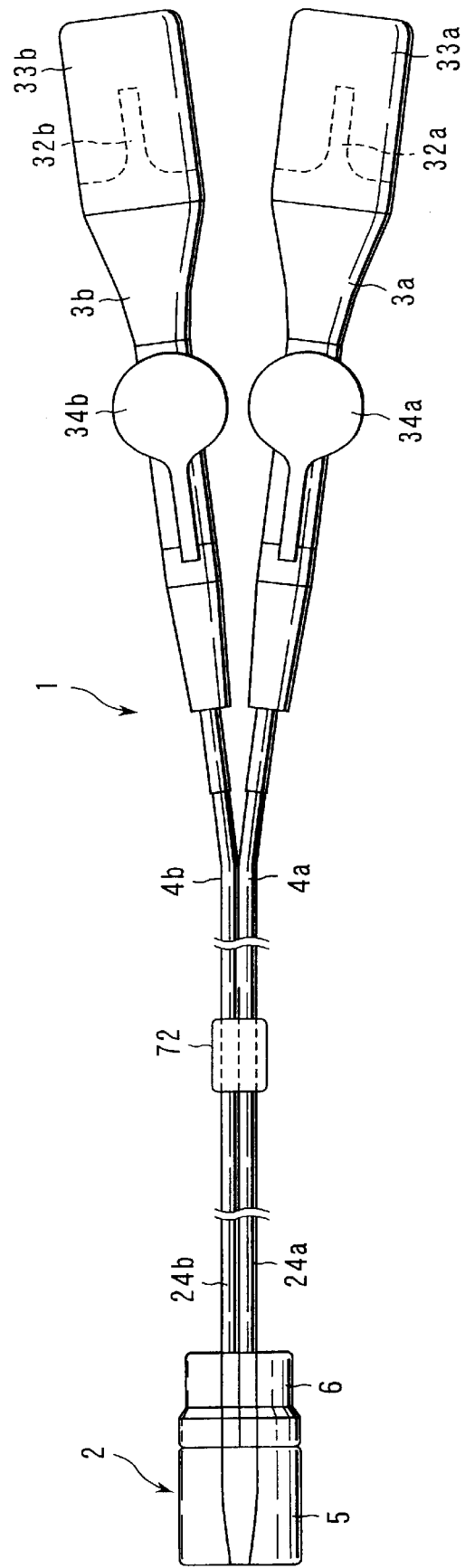
FIG. 18 is a plan view of the high-frequency treatment apparatus for the endoscope.
Figures 19A, 19B:
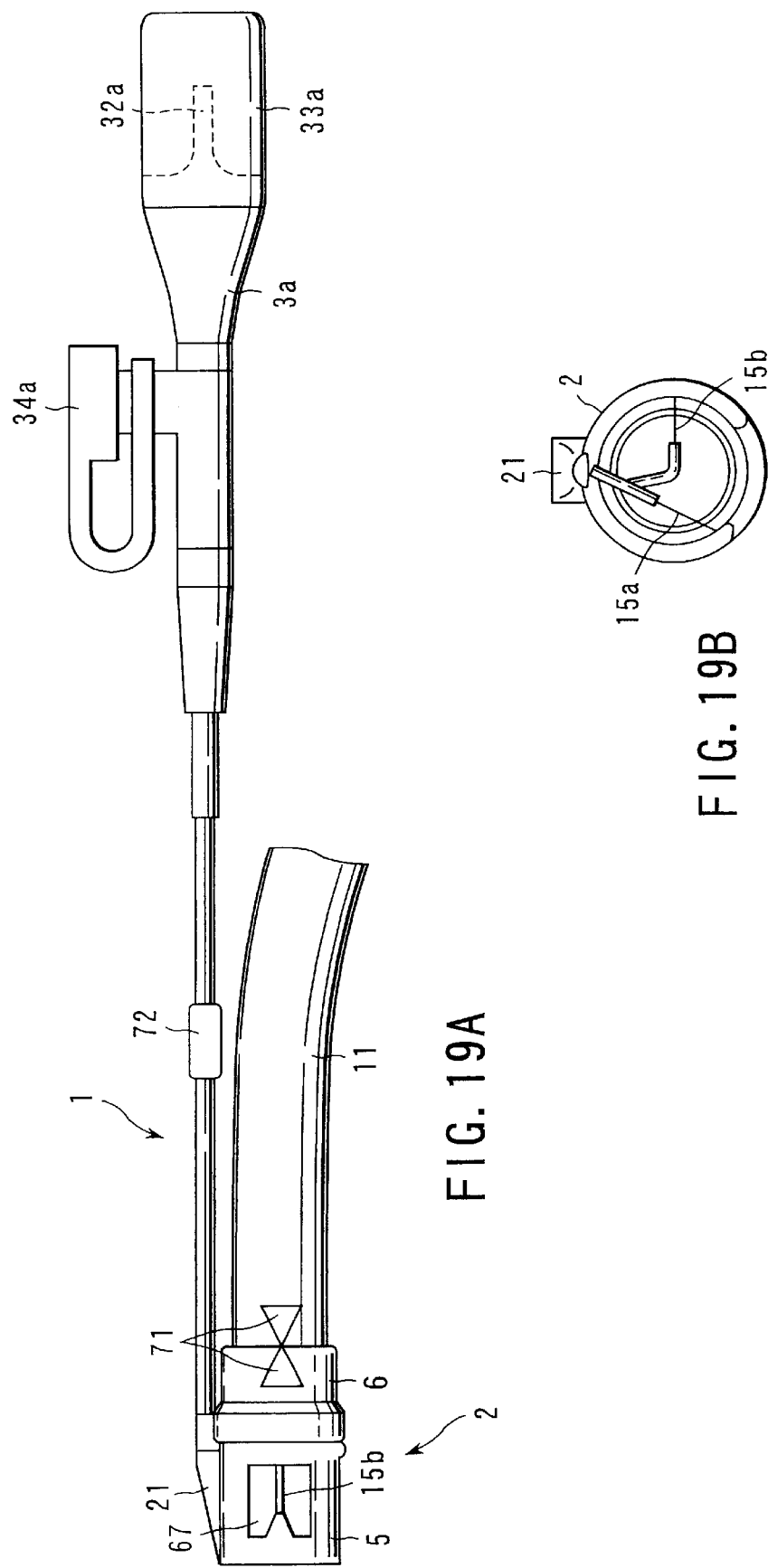
FIG. 19A is a side view of the whole treatment apparatus shown in FIG. 17.
FIG. 19B is a front view of a tip-end portion.

FIGS. 17 to 19 show the treatment apparatus for the endoscope according to a fourth embodiment. The basic constitution of the high-frequency incising apparatus for the endoscope according to the fourth embodiment is the same as that of the first to third embodiments.

FIG. 17 is a diagram of the hood 2 attached to the endoscope 10 seen from the tip-end side. As shown in FIG. 17, for the hood 2, the first or second embodiment is combined with the third embodiment in the same hood 2. That is, an incision line 15a is extended in the chord form in the plane of the circumferential direction, and an incision line 15b is extended in the plane of the axial direction. The incision lines 15a, 15b are insulated/coated, and coated lines 20a, 20b are passed through separate tube sheaths 24a, 24b to form cables 4a, 4b. As shown in FIG. 18, the cables 4a, 4b are connected to connectors 3a, 3b, respectively.

The coated lines 20a, 20b have different colors. For example, at least a portion of the coated line 20a is red-colored, at least a portion of the coated line 20b is blue-colored, and the lines can be distinguished by the different colors. The colors of the coated lines 20a, 20b are not limited to the above colors as long as the colors are different from each other. Moreover, the color of at least a portion of the connector 3a or 3b is constituted to be the same as that of the corresponding coated line 20a or 20b.

Since the color of the connector 3a or 3b is set to agree with that of the corresponding coated line 20a or 20b, it is easy to distinguish the electrode to be connected on the side of the connector 3a or 3b, and accidents because of switch mistakes can be prevented.

Moreover, for example, circle marks are attached to the coated line 20a and connector 3a, and triangular marks are attached to the coated line 20b and connector 3b. These may easily be distinguished using the marks instead of the colors. The marks are not limited to the above-described marks.

Holes 18a, 18b for passing through the coated lines 20a, 20b are formed in the cylindrical main body portion 5 of the hood 2. These holes 18a, 18b are positioned to be relatively close to each other. Thereby, one wire presser 21 is sufficient and can be compact. Moreover, cable insertion ports 25a, 25b for passing through the coated lines 20a, 20b are formed in the wire presser 21.

Moreover, indexes 71 indicating an attachment position of the hood 2 are indicated on the attaching portion 6 of the hood 2 and the tip-end portion 12 of the endoscope 10. These indexes 71 are aligned and the hood 2 is attached to the endoscope 10. Then, the incision lines 15a, 15b are positioned not to obstruct the field of view of the endoscope 10 or the use of other treatment instruments.

Two cables 4a, 4b are brought together by a sheath bundling member 72, and are prevented from being entwined with each other. Moreover, the sheath bundling member 72 may be moved along the cables 4a, 4b. Additionally, the form of the sheath bundling member 72 is not limited to that shown in FIGS. 18 and 19.

Moreover, the cables 4a, 4b may be formed by one two-lumen tube in which two lumens corresponding to the separate tube sheaths 24a, 24b are formed, and the coated lines 20a, 20b may separately be passed through the respective lumens. Moreover, the cables may also be formed by a multi-lumen tube in which a lumen for forming a water channel is further disposed.

As shown in FIG. 18, terminal cover portions 33a, 33b of the respective connectors 3a, 3b are set to be sufficiently longer than connection terminals 32a, 32b. In this manner, when power is supplied to one of the incision lines 15a, 15b, the operator is prevented from manually touching the connection terminal 32a or 32b not connected to the high-frequency power supply by mistake, and from receiving an electric shocked.

It is preferable to allow the colors or indexes of the respective connectors 3a, 3b to differ from each other, so that the incision line 15a or 15b connected to the high-frequency power supply can be recognized.

When the mucosa is resected in the circumferential direction by the high-frequency incising apparatus for the endoscope of the fourth embodiment, the connector 3a is connected to the high-frequency power supply. Thereafter, the mucosa can be resected in the circumferential direction with the same action as that of the first embodiment.

Moreover, when the mucosa is resected in the axial direction, the connector 3b is connected to the high-frequency power supply. Thereafter, the mucosa can be resected in the axial direction with the same action as that of the third embodiment.

According to the high-frequency incising apparatus for the endoscope of the fourth embodiment, the resection in the circumferential direction and the resection in the axial direction can be selectively carried out by one hood 2. Thereby, without changing the hood 2 once attached to the endoscope 10, the mucosa can be resected in the respective directions by one high-frequency incising apparatus, and the mucosa can quickly be resected. Additionally, it is easy to control the range to be resected.

Additionally, when two or more electrodes or incision lines are disposed in this manner, the direction is not limited to the above-described circumferential or axial direction. The electrode or the incision line may appropriately be disposed in a different direction as long as the mucosa can preferably be resected.

(Fifth Embodiment)

Figure 20:
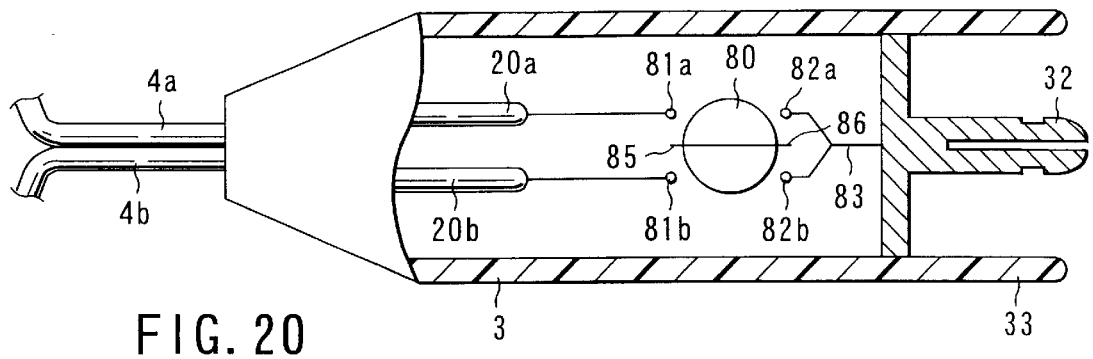
FIGS. 20 to 22 are partial longitudinal sectional views showing various modes of a connector portion of the high-frequency treatment apparatus for the endoscope according to a fifth embodiment of the present invention.
Figure 21:
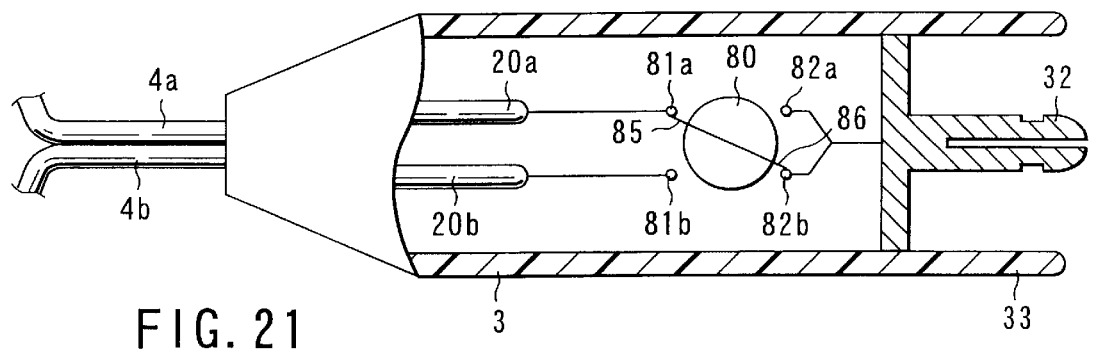
Figure 22:
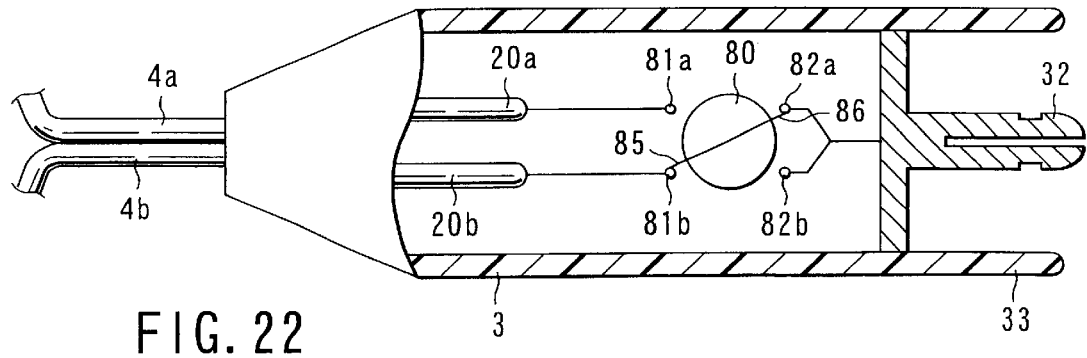

FIGS. 20 to 22 show the high-frequency incising apparatus for the endoscope as the treatment apparatus for the endoscope according to a fifth embodiment. The basic constitution of the high-frequency incising apparatus for the endoscope of the fifth embodiment is the same as that of the fourth embodiment.

In the fifth embodiment, two connectors in the fourth embodiment can be brought together into one connector 3, and the incision lines 15a, 15b to be turned on are selected by a changeover switch 80.

Two coated lines 20a, 20b are connected to first and second electrical contacts 81a, 81b disposed in the connector 3, respectively. Furthermore, the connector 3 includes third electrical contacts 82a, 82b. These third electrical contacts 82a, 82b are electrically connected to the common connection terminal 32 via a conductor 83.

The changeover switch 80 is constituted as a rotary switch, and includes a first piece 85 which can selectively contact the first and second electrical contacts 81a and 81b, and a second piece 86 which can selectively contact the third electrical contacts 82a, 82b. The first and second pieces 85 and 86 are electrically connected to the common connection terminal 32.

The changeover switch 80 can change a connection state with the high-frequency power supply for the first and second electrical contacts 81a and 81b, and there are the following three types of switch states.

A neutral position is a position where the first and second pieces 85 and 86 of the changeover switch 80 do not contact any of the electrical contacts 81a, 81b, 82a, 82b (FIG. 20).

A first connection position (circumferential-direction resection) is a state in which the first piece 85 of the changeover switch 80 contacts the first electrical contact 81a, and the second piece 86 contacts the third electrical contact 82b (FIG. 21).

A second connection position (axial-direction resection) is a state in which the first piece 85 of the changeover switch 80 contacts the second electrical contact 81b, and the second piece 86 contacts the third electrical contact 82a (FIG. 22).

Additionally, the neutral position does not necessarily have to be present. Moreover, the switch is not limited to a rotary switch as long as the position can be switched, and any type of changeover switch may be used.

When the resection is performed in the circumferential direction by the high-frequency incising apparatus for the endoscope according to the fifth embodiment, the changeover switch 80 is rotated counterclockwise from the neutral position. Thereby, the mode is set to a circumferential-direction incision mode in which the incision line 15a is electrically connected to the high-frequency power supply. This incising method is the same as that of the first embodiment.

Moreover, when the resection is performed in the axial direction, the changeover switch 80 is rotated clockwise from the neutral position. Thereby, the mode is set to an axial-direction incision mode in which the incision line 15b is electrically connected to the high-frequency power supply. This incising method is the same as that of the third embodiment.

According to the high-frequency incising apparatus for the endoscope of the fifth embodiment, one connector 3 is sufficient, the need to replace the power cord for connection to the high-frequency power supply is therefore obviated, and the replacement operation is further facilitated.

(Sixth Embodiment)

FIGS. 23 to 30 show the treatment apparatus for the endoscope according to a sixth embodiment. The basic constitution of the high-frequency incising apparatus for the endoscope of the sixth embodiment is the same as that of the first embodiment.

Figures 23, 24:
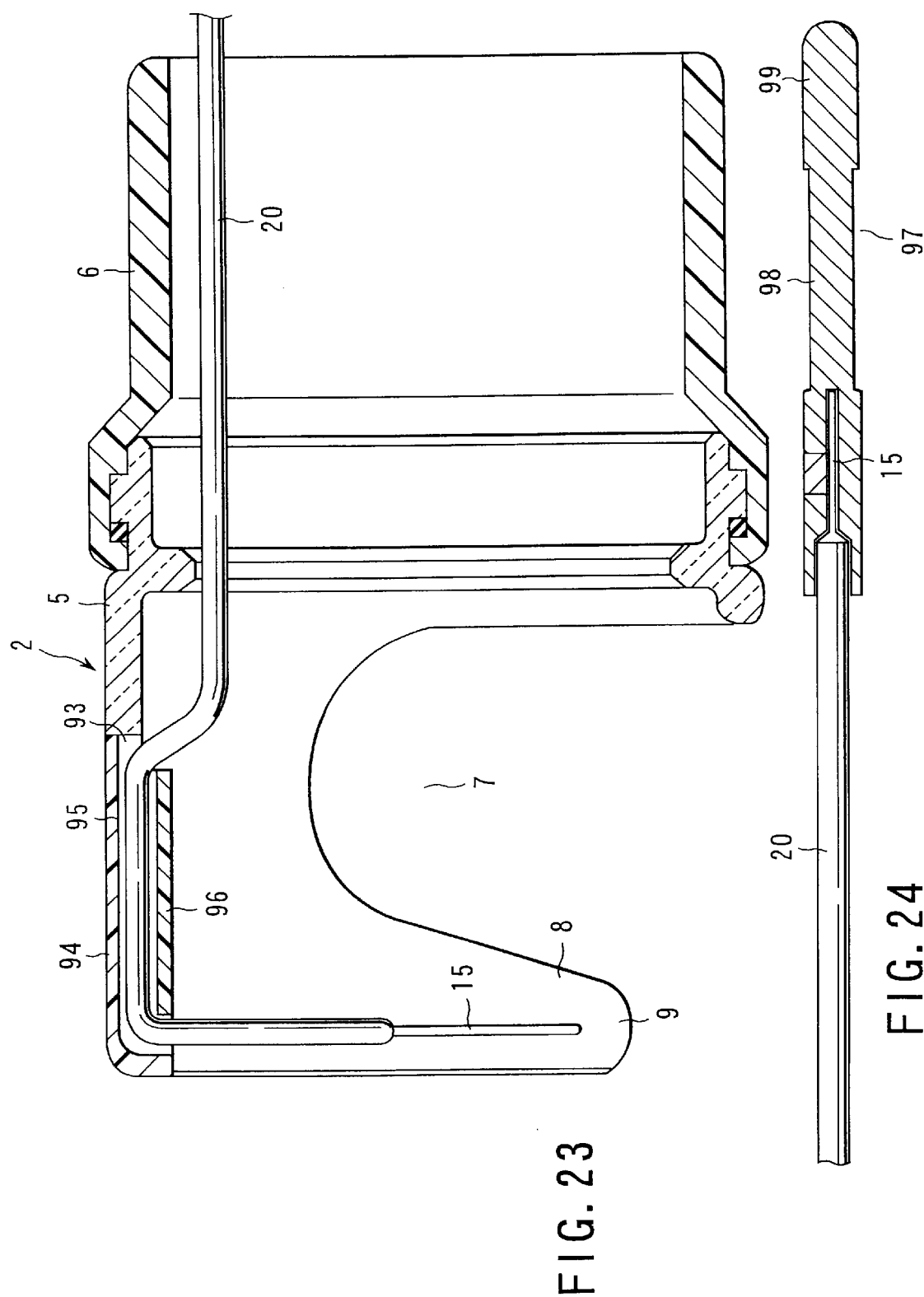
FIG. 23 is a longitudinal sectional view of the hood portion of the high-frequency treatment apparatus for the endoscope according to a sixth embodiment of the present invention.
FIG. 24 is a partial longitudinal sectional view of a terminal of the treatment apparatus shown in FIG. 23.

The high-frequency incising apparatus for the endoscope according to the sixth embodiment includes the hood 2, the coated line 20, a forceps port connection apparatus 91 and a connector portion 92. The hood 2 basically has the same constitution as that of the hood of the first embodiment, but an elongated slit 93 is formed in the axial direction in the cylindrical main body portion 5. A wire passage member 94 is fitted in the elongated cut of the slit 93. The wire passage member 94 is bonded/fixed to the cylindrical main body portion 5. A groove-shaped wire passage 95 opened inside the cylindrical main body portion 5 is formed in the wire passage member 94. As shown in FIG. 23, the portion of the coated line 20 extending from the incision line 15 stretched in the chord form is disposed in the wire passage 95, and extends to the base end along the inside of the cylindrical main body portion 5 and attaching portion 6 of the hood 2 from the wire passage 95. A wire presser 96 is bonded/fixed to the wire passage member 94 via the coated line 20 from the inside of the wire passage 95.

As shown in FIG. 24, a terminal 97 formed of a stainless steel conductor is disposed on the base end of the coated line 20, and the terminal 97 is connected to the base end of the incision line 15. The terminal 97 includes a concave portion 98 and convex portion 99.

The outer diameter of the coated line 20 and terminal 97 is sufficiently smaller than the inner diameter of the treatment instrument insertion passage 69 of the endoscope 10, and is, for example, of the order of 0.3 mm to 1 mm.

Figure 26:
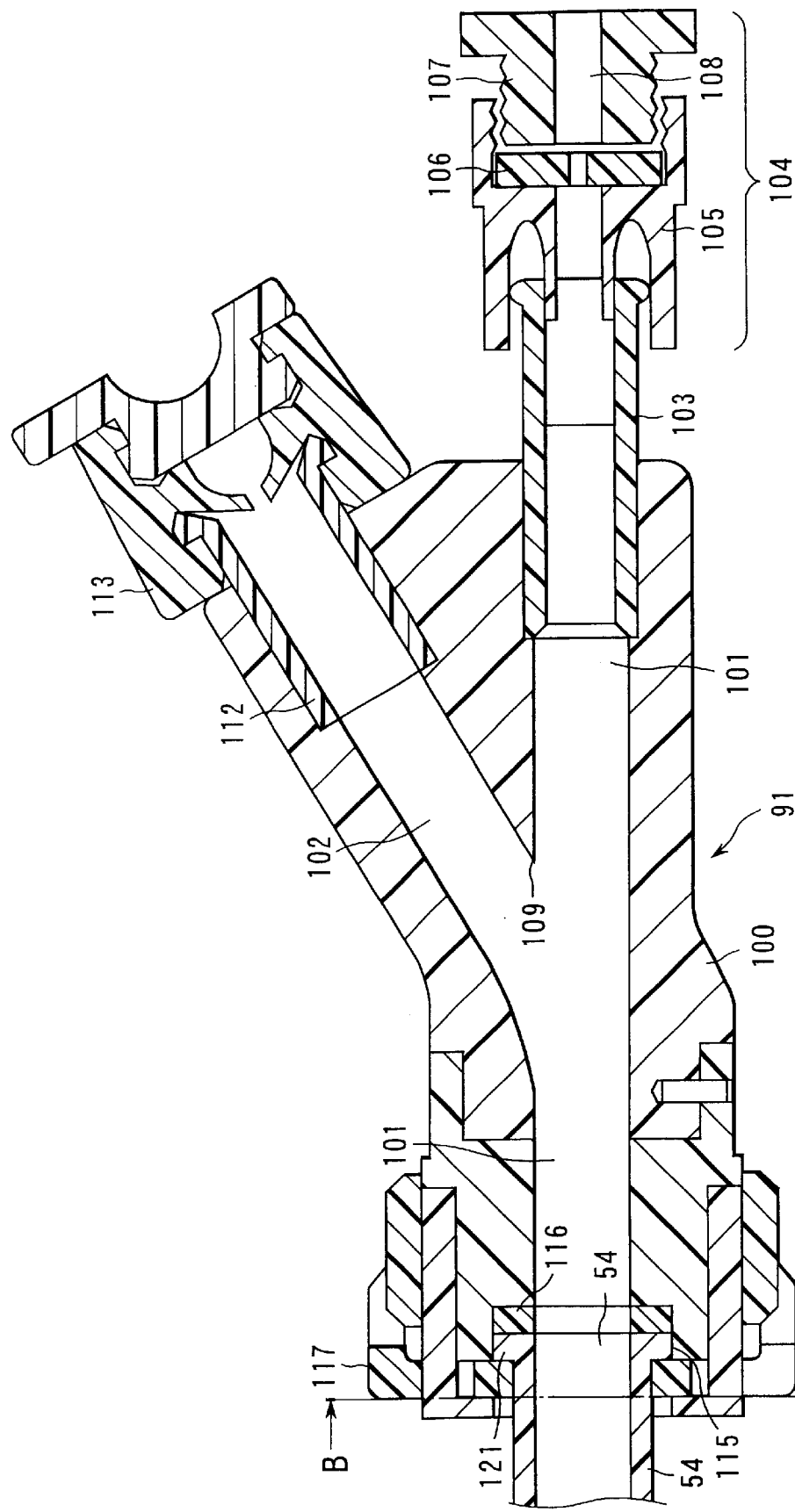
FIG. 26 is a longitudinal sectional view of a forceps port connection apparatus of the high-frequency treatment apparatus for the endoscope.

As shown in FIG. 26, the forceps port connection apparatus 91 has a connection apparatus main body 100. In the connection apparatus main body 100, there are disposed a first insertion inner cavity (first insertion port) 101, and a second insertion inner cavity (second insertion port) 102 branched midway from the first insertion inner cavity 101. A first cap 103 is fit in a hand-side end of the first insertion inner cavity 101, and bonded and fixed to the connection apparatus main body 100.

An attachable/detachable air-tight plug (water-tight plug) 104 is attached to the first cap 103. This air-tight plug 104 is constituted of a cap connection portion 105, O ring 106 superior in elasticity and plug portion 107. A cable insertion hole 108 is formed to the plug portion 107 over from the cap connection portion 105.

Additionally, the connection apparatus main body 100 is separate from the first cap 103, but may integrally be formed. Moreover, the connection apparatus main body 100 and air-tight plug 104 may not be separate and may be integral.

The first insertion inner cavity (first insertion port) 101, first cap 103, cap connection portion 105, O ring 106 and plug portion 107 have inner diameters such that the coated line 20 can be inserted.

On the other hand, the second insertion inner cavity (insertion port) 102 is branched from the first insertion inner cavity (first insertion port) 101 obliquely backwards in the position of a branch point 109 inside the connection apparatus main body 100. A second cap 112 is fit in the hand-side end of the second insertion inner cavity (insertion port) 102, and bonded/fixed to the connection apparatus main body 100. An attachable/detachable forceps plug 113 is attached to the second cap 112, and this keeps the portion of the second cap 112 to be airtight.

A groove 115 in which the treatment instrument insertion port 54 of the endoscope 10 is to be fit is disposed on the tip-end side of the connection apparatus main body 100, and a rubber ring 116 for air tightness is fit in a base-end side inner end of the groove 115. Moreover, an operating slider 117 for switching the fixing/unfixing of the treatment instrument insertion port 54 of the endoscope 10 with respect to the forceps port connection apparatus 91 is disposed in a tip-end side portion of the groove 115. The operating slider 117 can vertically move as shown in FIG. 27.

A gap 118 via which the treatment instrument insertion port 54 of the endoscope 10 is passed is formed in the operating slider 117. Protrusions 119 are disposed around the gap 118. These protrusions 119 serve as stoppers so that the slider 117 is not moved unless moved intentionally during the fixing of the forceps port connection apparatus 91 to the treatment instrument insertion port 54. Moreover, a flange 112 is disposed on the base end of the treatment instrument insertion port 54. The outer diameter of the flange 121 is larger than the outer diameter on the tip-end side.

The gap 118 is divided into first and second regions 123 and 124 via the protrusion 119. The first region 123 is substantially circular, and the inner diameter thereof is smaller than the outer diameter of the flange 121, and larger than the outer diameter of the tip-end portion of the treatment instrument insertion port 54. The second region 124 may have an optional shape, and has a sufficient size such that the treatment instrument insertion port 54 including the flange 121 can sufficiently be passed through.

Figure 28:
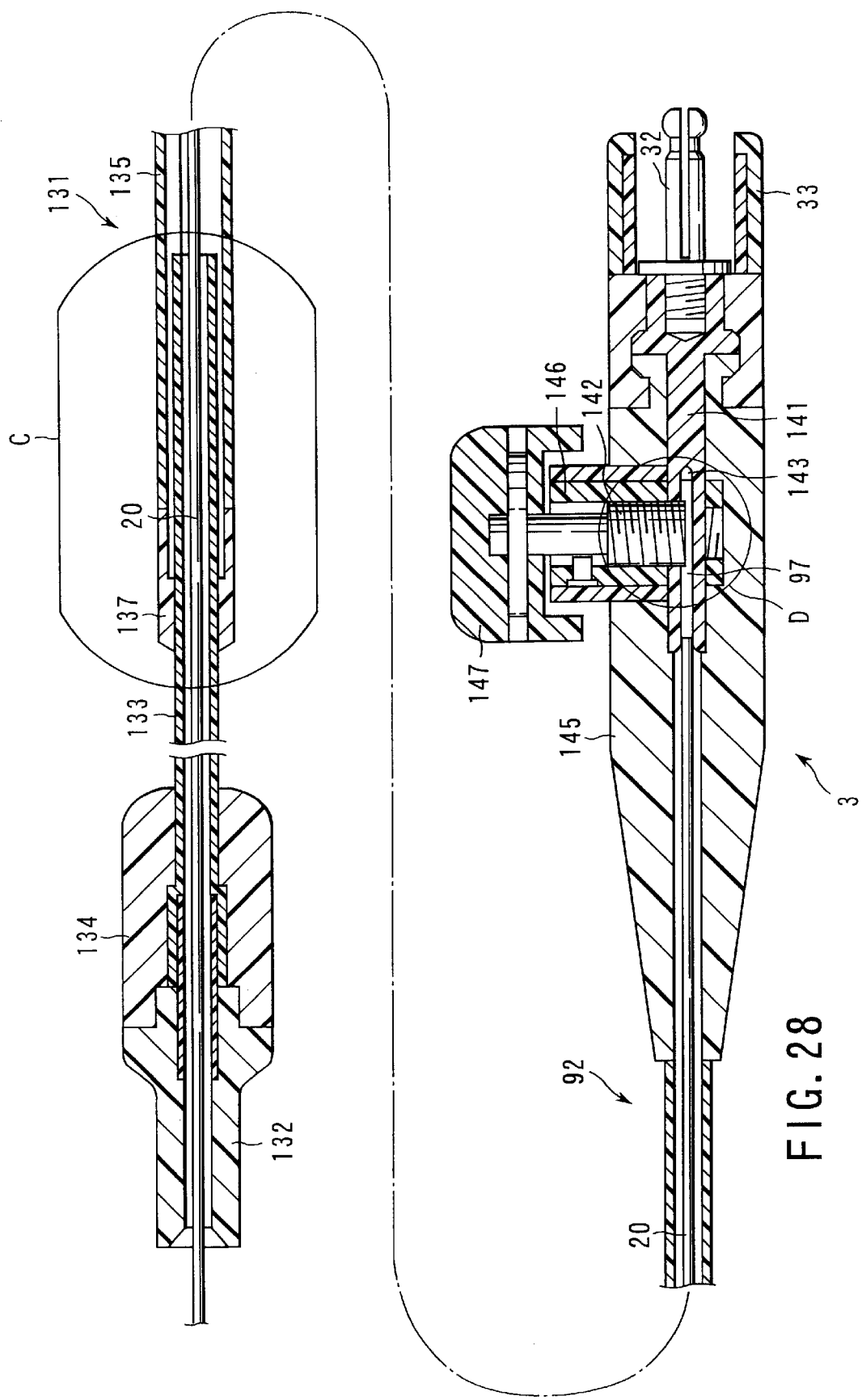
FIG. 28 is a longitudinal sectional view of the connector portion of the high-frequency treatment apparatus for the endoscope.

The connector portion 92 shown in FIG. 25 will next be described. The connector portion 92 is constituted of a tube portion 131 and the connector 3. As shown in FIG. 28, the tube portion 131 is constituted of a connection tip-end portion 132, first cable insertion tube 133, connector 134 of the connection tip-end portion 132 and first cable insertion tube 133, and second cable insertion tube 135. The connection tip-end portion 132 fits in the cable insertion hole 108 formed in the plug portion 107 of the air-tight plug (water-tight plug) 104 in the forceps port connection apparatus 91, and has a mode by which the air-tight plug (water-tight plug) 104 can be connected to the connector portion 92.

Moreover, the first cable insertion tube 133 has a sufficient inner diameter such that the coated line 20 can be passed through. The second cable insertion tube 135 has an inner direction larger than the outer diameter of the first cable insertion tube 133. The inner/outer diameters of the first cable insertion tube 133 and second cable insertion tube 135 are set to appropriate sizes such that the coated line 20 is not kinked. Furthermore, the first cable insertion tube 133 can slide inside the second cable insertion tube 135.

As shown in FIG. 29, a tube diameter enlarging member 136 is fit in the inner cavity of the base-end portion of the first cable insertion tube 133. The outer diameter of the portion of the first cable insertion tube 133 in which the tube diameter enlarging member 136 is fit has a size such that the portion can marginally slide in the second cable insertion tube 135.

Moreover, as shown in FIG. 29, a tube stopper 137 is fixedly connected to the tip end of the second cable insertion tube 135. The inner diameter of the tube stopper 137 is larger than the outer diameter of the portion of the first cable insertion tube 133 excluding the tube diameter enlarging member 136, and smaller than the outer diameter of the portion of the first cable insertion tube 133 with the tube diameter enlarging member 136 fit therein. Thereby, even when the first and second cable insertion tubes 133 and 135 are largely slid in the same direction as that for extending the total length of the connector portion 92, the first cable insertion tube 133 is not disengaged from the second cable insertion tube 135.

As shown in FIG. 28, the connector 3 includes the connection terminal 32, the terminal cover portion 33, a connector 141, and a fixed rod 142. The connector 141 electrically connects the connection terminal 32 to the terminal 97. The connector 141 includes a hole 143 in which the terminal 97 is inserted and stopped. Moreover, the fixed rod 142 has an outer surface formed in a screw shape, and is meshed with a support cylinder 146 attached to a main body member 145 of the connector 3. A knob 147 is attached to the outer end of the fixed rod 142. When the knob 147 is rotated, the fixed rod 142 vertically moves.

When the fixed rod 142 is screwed in, the tip end of the fixed rod 142 abuts on the peripheral side surface of the terminal 97. A small-diameter portion 148 forming a concave portion into which the tip end of the fixed rod 142 abuts is formed in the peripheral side surface of the terminal 97. Therefore, even when the terminal 97 is forcibly pulled out, a tip-end concave portion 149 of the terminal 97 is caught by the fixed rod 142, and the terminal 97 does not come out of the connector 3.

The action by the high-frequency incising apparatus for the endoscope of the sixth embodiment will next be described.

As a preparatory operation, first the forceps port connection apparatus 91 is attached to the treatment instrument insertion port 54 of the endoscope 10. This method comprises:

i) setting the slider 117 of the connection apparatus main body 100 into a position shown by a two-dot chain line in FIG. 27;

ii) fitting the aperture end of the treatment instrument insertion port 54 into the groove 115; and iii) allowing the slider 117 to slide to a position shown by a solid line in FIG. 27.

Thereby, the flange 121 of the treatment instrument insertion port 54 is locked by the protrusion 119 of the slider 117, and is not disengaged from the groove 115. Moreover, the protrusion 119 of the slider 117 has an appropriate elasticity, and a distance therebetween is appropriately smaller than the outer diameter of the treatment instrument insertion port 54 of the endoscope 10. Therefore, the protrusion sufficiently fixes the forceps port connection apparatus 91 to the treatment instrument insertion port 54. Additionally, since the protrusion 119 has elasticity, the protrusion can be detached by moving the slider 117. Since the groove 115 is sufficiently narrow, air does not leak from the groove.

Subsequently, the coated line 20 is inserted through the endoscope 10 from the tip end of the treatment instrument insertion passage 69, passed through the first insertion inner cavity (insertion port) 101 in the forceps port connection apparatus 91, and drawn out of the cable insertion hole 108.

Thereafter, the hood 2 is attached to tip-end portion 12 of the endoscope 10, and the coated line 20 is fully pulled out. In this case, the coated line 20 and terminal 97 are sufficiently thin, and are therefore easily inserted into the treatment instrument insertion passage 69. Furthermore, even when the coated line 20 is inserted into the treatment instrument insertion passage 69, another treatment instrument can be inserted in the same treatment instrument insertion passage 69 and used.

Subsequently, the plug portion 107 is rotated and the O ring 106 is compressed. Then, the inner diameter of the O ring 106 to which pressure is applied is reduced, a gap present between the coated line 20 and the hole of the O ring 106 is eliminated, and air tightness is kept in the air-tight plug (water-tight plug) 104. When the coated line 20 is not inserted, the plug portion 107 is fully screwed in. Even when the portion is pressed onto the O ring 106, the inner diameter of the O ring 106 is not broken out, and the air tightness in the forceps port connection apparatus 91 is not kept.

Next, as shown in FIG. 30, the terminal 97 is inserted into the terminal stopper hole 143 of the connector portion 92, and inserted until the terminal is stopped by the innermost end of the terminal stopper hole 143. Thereafter, the knob 147 is rotated and the terminal 97 is fixed to the connector 141.

Finally, the connection tip-end portion 132 is fit in the cable insertion hole 108 of the plug portion 107.

When the fixed rod 142 is fastened by the knob 147, the tip end of the fixed rod 142 bites in the small-diameter portion (concave portion) 148 of the terminal 97. Therefore, even when the terminal 97 is forcibly pulled out, the concave portion 149 of the terminal 97 is caught by the fixed rod 142, and the terminal 97 does not come out of the connector 3.

As described above, the tube portion 39 can slide in a sufficiently large range, and the whole length of the first and second cable insertion tubes 133 and 135 can be adjusted.

The incising method by the high-frequency incising apparatus for the endoscope according to the sixth embodiment is the same as that of the first embodiment.

According to the high-frequency incising apparatus for the endoscope according to the sixth embodiment, since the coated line 20 is passed through the treatment instrument insertion passage 69, the outer diameter of a scope diameter is suppressed, and therefore the instrument can easily be inserted in the body.

Moreover, since the coated line 20 is passed into the treatment instrument insertion passage 69, a possibility of leakage of current into the body from the coated line 20 is reduced without limit.

Furthermore, since the forceps port connection apparatus 91 and connector portion 92 are disposed, the kink of the portion of the coated line 20 exposed from the treatment instrument insertion port 54 can be prevented.

Additionally, since the tube portion 131 is elastic, a fine error of the length of the coated line 20 projecting from the plug portion 107 is flexibly handled, and the whole exposed coated line 20 can be protected by a tube material. Thereby, much precision of the length of the coated line 20 is not required. Moreover, even in the endoscope 10 having a different length, the coated line 20 can be used without changing the length thereof.

Moreover, the structure described in the sixth embodiment is not applied only to the hood 2 with the incision line 15 disposed in the tip end thereof, and is effective for any inserting type of the high-frequency treatment instrument.

(Seventh Embodiment)

Figure 31:
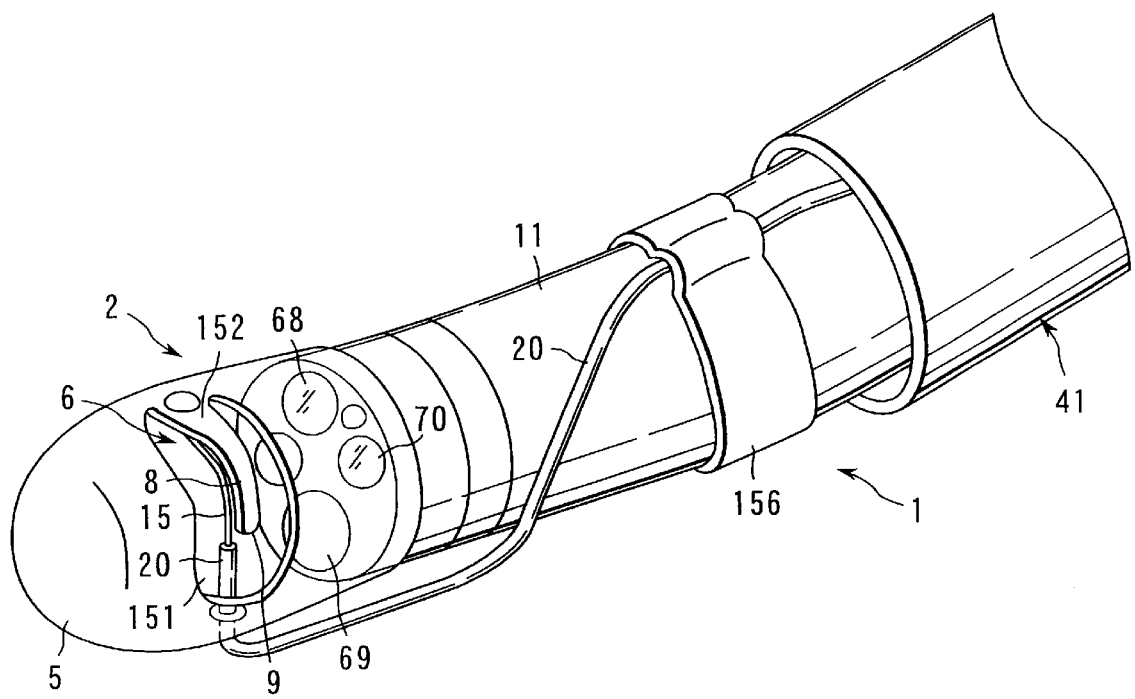
FIG. 31 is a perspective view of the vicinity of the hood portion of the treatment apparatus for the endoscope according to a seventh embodiment of the present invention.
Figure 32:
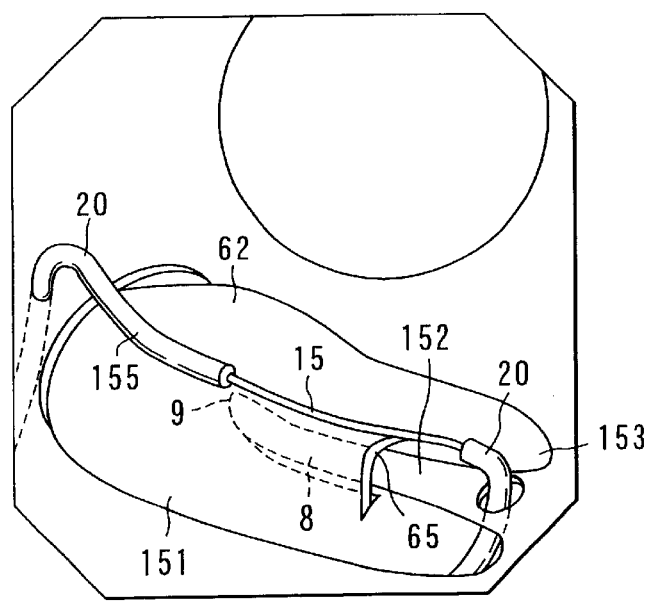
FIG. 32 is a diagram of an endoscope image reflecting the use state of the treatment apparatus shown in FIG. 31.

FIGS. 31 and 32 show the treatment apparatus for the endoscope according to a seventh embodiment. The basic constitution of the high-frequency incising apparatus for the endoscope as the seventh embodiment is the same as that of the first embodiment.

The hood 2 of the high-frequency incising apparatus for the endoscope of the seventh embodiment has a bullet shape in which the tip end of the cylindrical main body portion 5 is closed. Moreover, the tip end of the hood 2 is not limited to the bullet shape, and may have a dome shape or a chambered flat shape. A U-shaped side aperture 151 is disposed as an opening in the cylindrical main body portion 5.

In the side aperture 151, the in-tissue inserting portion 8 is disposed to project from one end of the peripheral direction of the side aperture 151 to the other end of the peripheral direction. The in-tissue inserting portion 8 may project from either the left or right side of the side aperture 151. Moreover, the shape of the side aperture 151 may be elliptical, circular, or triangular as long as the in-tissue inserting portion 8 is projected. For the size of the side aperture 151, the width is in the range of 4 mm to 20 mm, and the length is preferably of the order of 4 mm to 20 mm.

Moreover, the tip end of the incision line 15 is bent in the vicinity of a base end 152 of the in-tissue inserting portion 8, and fixed to the base end 152. A bent portion 153 is raised/formed inside the in-tissue inserting portion 8. The incision line 15 is disposed along the peripheral direction to the side aperture 151 from the inside of the in-tissue inserting portion 8 as if bridged. A distance between the in-tissue inserting portion 8 and incision line 15 is in the range of 1 mm to 3 mm.

Moreover, the incision line 15 is coated with an insulation coat 155 to an inner-side position in the tip end 9 of the in-tissue inserting portion 8. That is, the incision line 15 is exposed only inside the in-tissue inserting portion 8.

In the seventh embodiment, the coated line 20 as a cable is not passed through a tube sheath, and is fixed directly to the inserting portion 11 of the endoscope 10 by a medical tape 156. This prevents the outer diameter of the inserting portion 11 of the endoscope 10 from increasing.

The action by the high-frequency incising apparatus for the endoscope of the seventh embodiment will be described next. The operation performed until the small incision 65 is added to the mucosa 62 and the in-tissue inserting portion 8 is inserted under the mucosa 62 is the same as that of the first embodiment.

Next, the portion corresponding to the side aperture 151 is brought into contact with the mucosa 62, and the sucking operation of the endoscope 10 is performed. Thereby, when air in the hood 2 is sucked and the air becomes thin, the mucosa 62 is sucked up into the side aperture 151. The mucosa 62 is sufficiently sucked up, the mucosa 62 is brought in close contact with the incision line 15, power is supplied to the incision line 15 and the mucosa 62 is incised. The above-described operation is repeated, and the inner wall of the lumen organ is incised in an annular shape.

According to the high-frequency incising apparatus for the endoscope of the seventh embodiment, since the tip end of the hood 2 is closed, the mucosa 62 is not sucked from the tip-end side. Therefore, the mucosa 62 of the unintended portion is not incised by mistake. Moreover, since the coated line 20 is not passed through the tube sheath, the outer diameter of the inserting portion 11 of the endoscope 10 is not enlarged.

(Eighth Embodiment)

Figure 33:
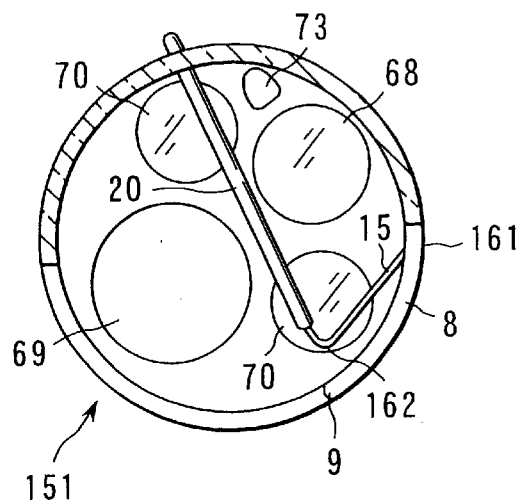
FIG. 33 is a transverse sectional view of a hood of the treatment apparatus for the endoscope according to an eighth embodiment of the present invention.

FIG. 33 shows the treatment apparatus for the endoscope according to an eighth embodiment. The basic constitution of the high-frequency incising apparatus for the endoscope as the eighth embodiment is the same as that of the above-described seventh embodiment.

As shown in FIG. 33, the incision line 15 of the eighth embodiment substantially forms an "L" shape in which an acute angle is formed between a long leg portion and short leg portion. That is, a bent point 162 of the "L" shape is positioned on the side of a base end 161 a little distant from the tip end 9 of the in-tissue inserting portion 8, and the portion of the incision line 15 positioned further on the base-end side is positioned inside the in-tissue inserting portion 8. Moreover, the portion of the coated line 20 is disposed apart from the portion of the in-tissue inserting portion 8 and the opening portion of the side aperture 151.

Moreover, when the hood 2 is attached to the endoscope 10, as shown in FIG. 33, the coated line 20 is disposed so that the line is not positioned in front of the treatment instrument insertion passage 69. Moreover, the incision line 15 or the coated line 20 is positioned not to obstruct the front surface of the observation window (objective lens) 68. Additionally, a reference numeral 73 in FIG. 33 denotes a nozzle.

The action of the eighth embodiment is the same as that of the seventh embodiment. As the effect of the eighth embodiment, since the incision line 15 and coated line 20, particularly the portion of the coated line 20 are not positioned in the vicinity of the inside of the side aperture 151, the mucosa 62 can easily be sucked into the side aperture 151.

Moreover, since the coated line 20 does not extend to the front surface of the treatment instrument insertion passage 69, an operation of raising the mucosa 62 from the side aperture 151 with the grip forceps projected from the treatment instrument insertion passage 69 and inserting the in-tissue inserting portion 8 into the mucosa, or making an injection is not obstructed. Furthermore, since the incision line 15 or the coated line 20 does not extend to the front surface of the observation window (objective lens) 68, the view field of the endoscope 10 is easily secured. As a result, according to the eighth embodiment, the method becomes further easy.

(Ninth Embodiment)

Figure 34:
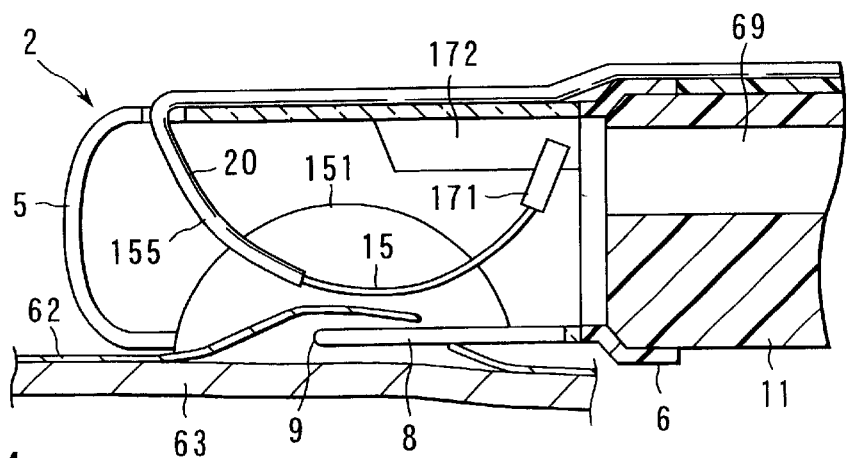
FIG. 34 is a longitudinal sectional view showing the use state of the treatment apparatus for the endoscope according to a ninth embodiment of the present invention.
Figure 35:
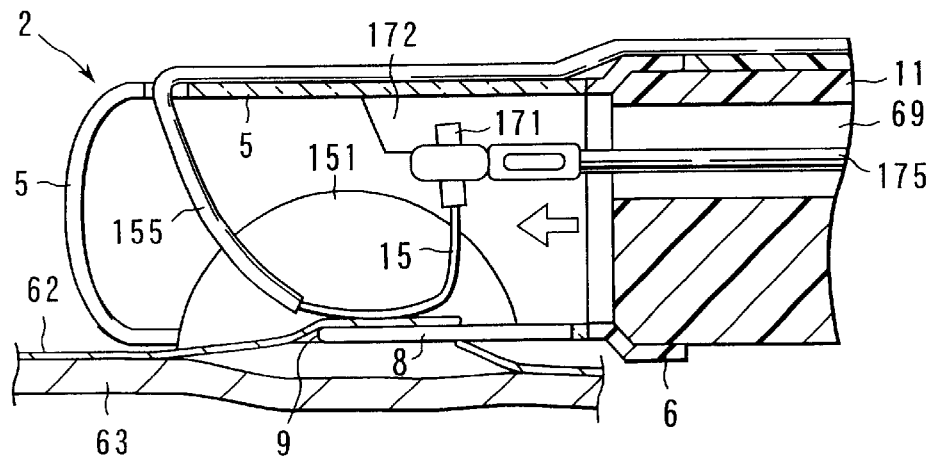
FIG. 35 is a longitudinal sectional view showing the use state of the treatment apparatus shown in FIG. 34.

FIGS. 34 and 35 show the treatment apparatus for the endoscope according to a ninth embodiment. The basic constitution of the high-frequency incising apparatus for the endoscope as the ninth embodiment is the same as that of the above-described first embodiment.

Moreover, the constitution of the hood 2 is substantially the same as that of the seventh embodiment. The incision line 15 and in-tissue inserting portion 8 are arranged in the axial direction. The in-tissue inserting portion 8 is made of ceramic superior in high-frequency resistance, and bonded/fixed to the hood 2. The in-tissue inserting portion 8 may be a heat-resistant glass material which is not fused by high-frequency heat, or a resin superior in high-frequency resistance.

Moreover, the in-tissue inserting portion 8 extends to the tip end of the side aperture 151 from the base end thereof. Furthermore, the incision line 15 is formed of a stainless steel spring line material only in the hood 2, and a soft linear material in the vicinity of the attaching portion 6 of the hood 2. Additionally, the incision line 15 may be a restorable material, such as a super elastic alloy.

The incision line 15 is disposed substantially in the U shape above the in-tissue inserting portion 8, and the end of the incision line 15 on the hand side is positioned in air in the hood 2. The hand-side end of the incision line 15 positioned in air forms an insulator portion 171. Moreover, two guide plates 172 are disposed in parallel on opposite sides of the end of the incision line 15 with a width a little larger than the outer diameter of the insulator portion 171.

As shown in FIG. 34, the incision line 15 is coated with the electrical insulation coat 155 to a portion right above the tip end 9 of the in-tissue inserting portion 8.

Moreover, the coated line 20 as the cable is the same as that of the seventh embodiment. Furthermore, the cable is the same as that of the first embodiment.

In the action of the ninth embodiment, the operation performed until the small incision 65 is added to the mucosa 62 is the same as that of the first embodiment. Thereafter, the endoscope 10 is moved forwards/backwards and rotated, and the in-tissue inserting portion 8 is thereby slipped under the mucosa 62.

Subsequently, the insulator portion 171 on the tip end of the incision line 15 is grasped with grip forceps 175, and pushed inwards/forwards. Then, as shown in FIG. 35, the incision line 15 is bent, and closely adheres to the mucosa 62. In this case, a tool for grasping the insulator portion 171 is not limited to the grip forceps and, for example, snare forceps or basket forceps may be used.

Moreover, the shape of the incision line 15 is changed, and the insulator portion 171 may be picked and pulled until the incision line 15 closely adheres to the mucosa 62.

Furthermore, the incision line 15 is superior in elasticity. Therefore, when a force for pushing out the grip forceps 175 is weakened, the line reversibly returns to its original shape. Moreover, the guide plates 172 on the opposite sides of the insulator portion 171 regulate the leftward/rightward movement of the insulator portion 171. Therefore, even when the incision line 15 is bent, the line is substantially correctly positioned on the in-tissue inserting portion 8.

Additionally, when the insulator portion 171 is pushed inwards, the incision line 15 is strongly pushed into the mucosa 62. Therefore, the mucosa 62 held between the in-tissue inserting portion 8 and incision line 15 is stretched to be thin, and easily cuts.

Subsequently, power is supplied to the incision line 15, and the mucosa 62 between the in-tissue inserting portion 8 and incision line 15 is linearly incised. Moreover, the endoscope 10 is pushed forwards, and the mucosa 62 is similarly incised. This is repeated several times, and the mucosa 62 is continuously resected. The subsequent operation is the same as that of the third embodiment.

According to the ninth embodiment, when the insulator portion 171 of the incision line 15 is pushed inwards, the incision line 15 is strongly pushed into the mucosa 62. Therefore, the mucosa 62 held between the in-tissue inserting portion 8 and incision line 15 is stretched to be thin, and easily cuts.

(Tenth Embodiment)

Figure 36:
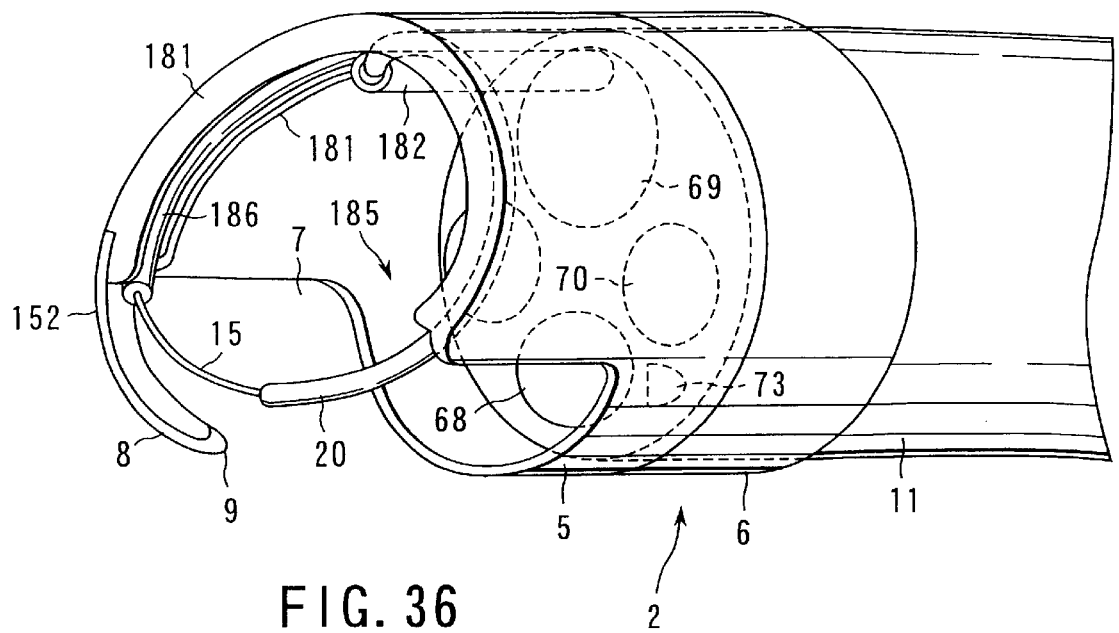
FIG. 36 is a perspective view showing the hood portion of the treatment apparatus for the endoscope according to a tenth embodiment of the present invention.

FIG. 36 shows the treatment apparatus for the endoscope according to a tenth embodiment. The basic constitution of the high-frequency incising apparatus for the endoscope of the tenth embodiment is the same as that of the above-described sixth embodiment.

The tip end of the cylindrical main body portion 5 in the hood 2 of the tenth embodiment is obliquely cut, and a forward portion thereof is opened. The in-tissue inserting portion 8 has inner/outer surfaces coated with a ceramic coat, is made of stainless steel, and is tapered to form a spatula shape.

Moreover, two guide rings 181 are obliquely arranged in the tip edge of the hood 2. The width of the guide ring 181 is in the range of 0.2 mm to 2 mm. Moreover, an interval between two guide rings 181 is 0.2 mm to 2 mm.

Additionally, the tip end of the cylindrical main body portion 5 may not be oblique, as long as the guide rings 181 are obliquely attached.

The hood 2 includes a guide tube 182 positioned on the tip-end side of the endoscope 10. The guide tube 182 is disposed so that the tip-end portion thereof is in a middle position between two guide rings 181 and the base end of the guide tube 182 is passed through the treatment instrument insertion passage 69 of the endoscope 10. The guide tube 182 is superior in slip property, and is made, for example, of Teflon resin.

Curled portions of the incision line 15 and coated line 20 having loop shapes are disposed between two guide rings 181. An electrical insulator portion 186 formed in the tip end of a loop 185 is positioned/fixed so that the end of the portion abuts on the guide tube 182. Moreover, the other end of the loop 185 is passed through the guide tube 182 inserted through the treatment instrument insertion passage 69, guided to the hand side of the endoscope 10, and connected to the high-frequency power supply (not shown). The exposed portion of the incision line 15 is positioned inside the in-tissue inserting portion 8.

The action of the tenth embodiment will next be described. In the action, the operation performed until the in-tissue inserting portion 8 is inserted under the mucosa 62 is the same as that of the first embodiment.

Figure 25:
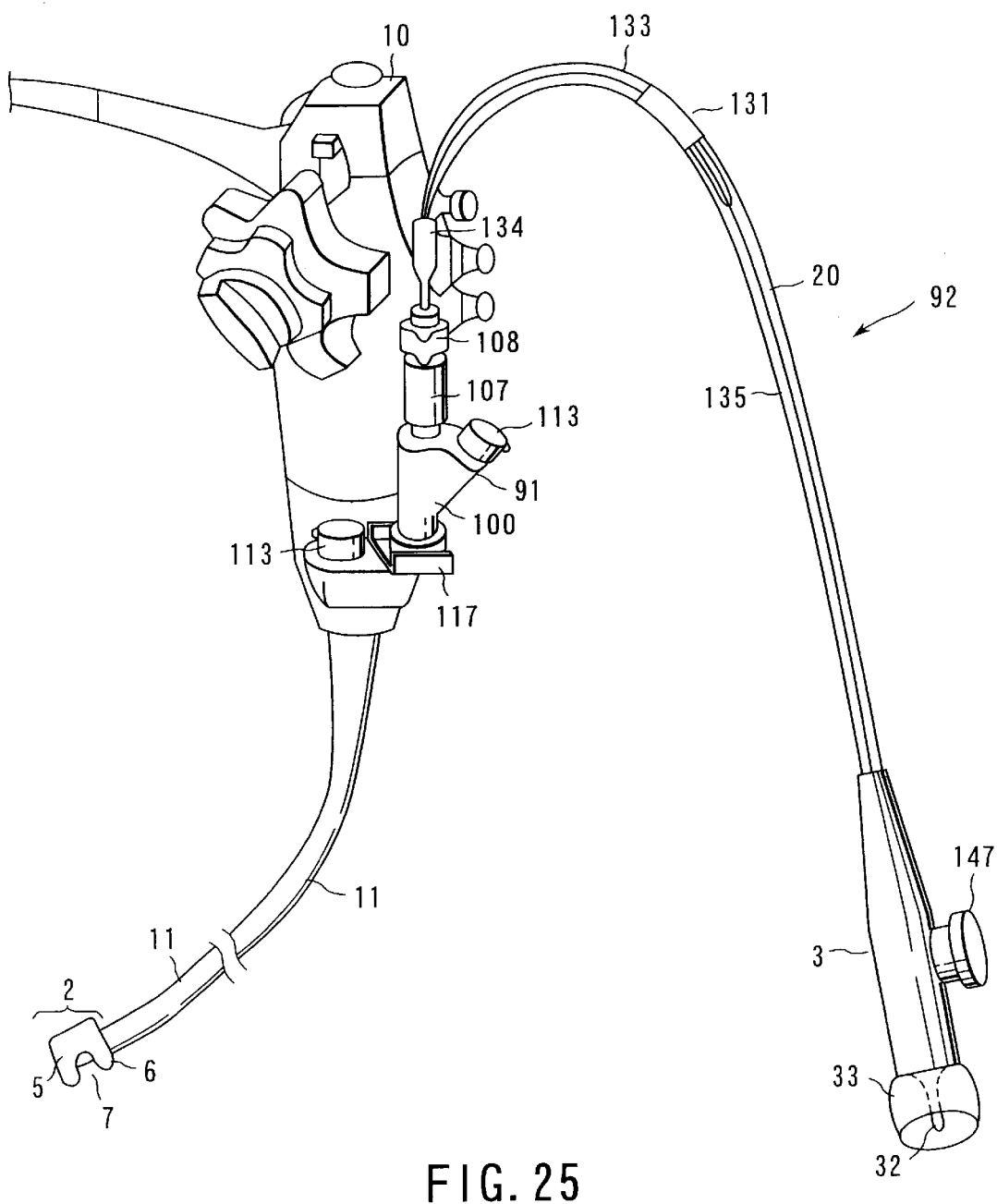
FIG. 25 is a perspective view showing the use state of the treatment apparatus shown in FIG. 23.

Thereafter, the first cable insertion tube 133 shown in FIG. 25 is held, and the second cable insertion tube 135 is pushed forwards so that the coated line 20 is pushed outwards (not shown). Then, the diameter of the loop 185 of the incision line 15 and coated line 20 increases along the guide rings 181, and the incision line 15 apart from the inner surface of the in-tissue inserting portion 8 by a predetermined distance approaches the inner surface of the in-tissue inserting portion 8. In this case, since the guide rings 181 are obliquely disposed, the loop 185 smoothly expands without being caught.

Additionally, the hand side of the coated line 20 may be distinguished, for example, by a red color as a warning color in order to prevent the incision line 15 from being detached from the in-tissue inserting portion 8 because of the excessively enlarged portion of the loop 185 of the incision line 15. Moreover, a stopper may be disposed on the coated line 20 on the hand side from the guide tube 182.

Thereafter, the incision line 15 contacts the mucosa 62 on the in-tissue inserting portion 8. Furthermore, after the coated line 20 is pushed outwards and the mucosa 62 is sufficiently held between the incision line 15 and in-tissue inserting portion 8, power is supplied to the incision line 15 and the mucosa 62 is incised.

Additionally, when the mucosa 62 is thick and is not easily cut, the in-tissue inserting portion 8 inserted under the mucosa 62 is scooped up by the angle operation, the mucosa 62 is stretched and the portion of the incision line 15 is pressed onto the mucosa 62. The above-described operation is repeated so that the mucosa of the lumen organ is incised in an annular shape.

Moreover, according to the tenth embodiment, the treatment by the treatment instrument, or the sucking operation is used less. Therefore, even when the guide tube 182 is inserted through the treatment instrument insertion passage 69, the tube is not an obstruction.

According to the tenth embodiment, an effect similar to that of the ninth embodiment is obtained.

(Eleventh Embodiment)

Figure 37:
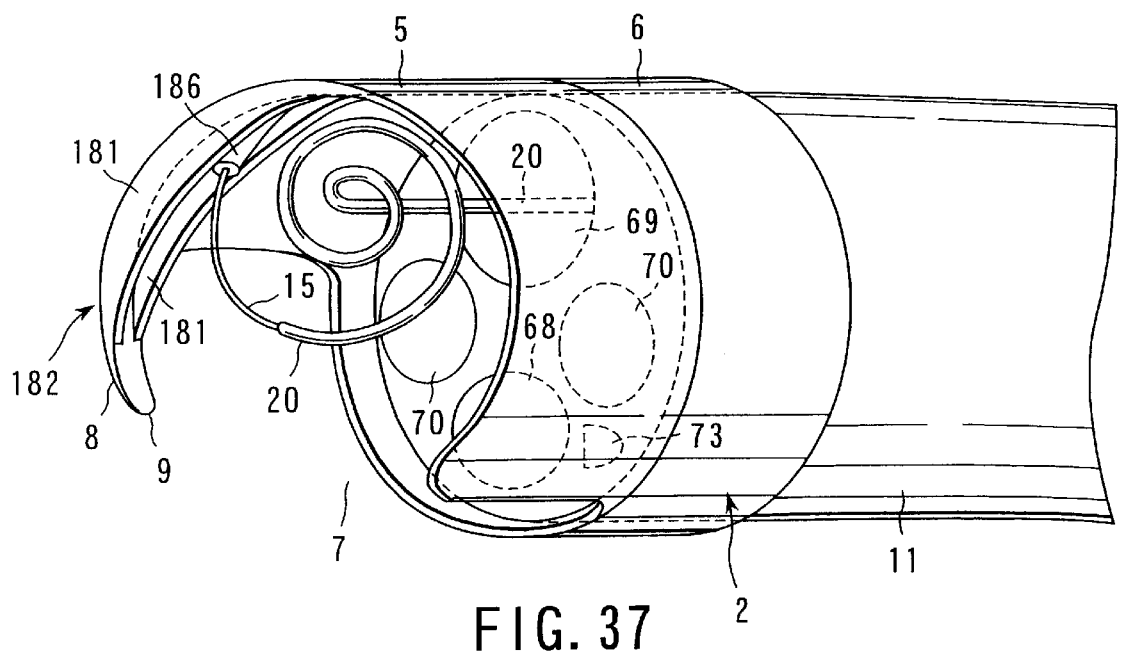
FIG. 37 is a perspective view showing the hood portion of the treatment apparatus for the endoscope according to an eleventh embodiment of the present invention.

FIG. 37 shows the treatment apparatus for the endoscope according to an eleventh embodiment. The basic constitution of the high-frequency incising apparatus for the endoscope as the eleventh embodiment is the same as that of the above-described sixth embodiment.

The hood 2 of the eleventh embodiment is different from the hood of the sixth embodiment in that the tip end of the cylindrical main body portion 5 is cut at right angles. Two guide rings 181 are formed to extend midway into the in-tissue inserting portion 8, and positioned on the opposite sides of the in-tissue inserting portion 8. The range in which the guide rings 181 are disposed is about ¼ of the whole circumference of the cylindrical main body portion 5.

Moreover, the curvature of the guide rings 181 is larger than the curvature of the inner diameter of the cylindrical main body portion 5. The inner periphery of each guide ring 181 forms a gently continuing slope midway in the in-tissue inserting portion 8. Furthermore, the guide ring 181 is integrally formed of the same material as that of the cylindrical main body portion 5, but may separately be formed.

Furthermore, the incision line 15 is formed of a super elastic metal line, and the tip end thereof has a shape wound in a spiral form. The incision line 15 is disposed apart from the inner surface of the in-tissue inserting portion 8 by the predetermined distance, but can be deformed so that the line abuts on the inner surface of the in-tissue inserting portion 8 by the operation. Additionally, the tip edge of the incision line 15 is coated with an insulator of an elastic material such as rubber inferior in slippage, and this portion is disposed as an insulator portion 186. The insulator portion 186 is contained between two guide rings 181, and fixed therebetween.

The operation of the eleventh embodiment performed until the in-tissue inserting portion 8 is inserted under the mucosa 62 is the same as that of the tenth embodiment. Moreover, when the in-tissue inserting portion 8 is inserted under the mucosa 62, the slope of the inner periphery of the guide ring 181 serves as a wedge. When the in-tissue inserting portion 8 is inserted, the mucosa 62 is detached from the muscle layer 63.

After the in-tissue inserting portion 8 is inserted into the mucosa 62 up to the base end thereof, the coated line 20 is rotated counterclockwise as seen from the base end of the endoscope 10. Then, the spiral loop of the tip end expands, and the incision line 15 abuts on mucosa 62 ridden onto the in-tissue inserting portion 8.

Furthermore, when the coated line 20 is rotated, the incision line 15 pushes the mucosa 62 inwards in a U form between the guide rings 181. In this state, power is supplied to the incision line 15, and the mucosa 62 is incised. In this case, the incision line 15 abuts the in-tissue inserting portion 8 from the base end in which the guide rings 181 are disposed on opposite sides. Therefore, the incision line 15 is not disengaged from the in-tissue inserting portion 8.

Moreover, when the coated line 20 is released on the hand side, the line returns to its original shape by a restoring force of the super elastic metal, and the in-tissue inserting portion 8 is detached from the incision line 15.

The above-described operation is repeated, and the mucosa of the lumen organ is incised in the annular shape.

According to the eleventh embodiment, the effect is obtained similarly as the ninth embodiment. Moreover, the mucosa 62 is pushed between the guide rings 181, and therefore the mucosa 62 is pushed inwards and easily cuts. Furthermore, since the incision line 15 contacts the mucosa 62 from the stretched base-end portion of the mucosa 62, it is easy to incise the mucosa. Additionally, the part to be incised is considerably above the muscle layer 63, and there is therefore an advantage that the influence of generated heat is not exerted onto the muscle layer 63.

(Twelfth Embodiment)

FIGS. 38 and 39 show the treatment apparatus for the endoscope according to a twelfth embodiment.

The high-frequency incising apparatus for the endoscope as the treatment apparatus for the endoscope of the twelfth embodiment has a constitution including a long high-frequency knife (spatula type knife) 187 which can be inserted through the treatment instrument insertion passage 69 of the endoscope 10 in addition to the hood 2.

For the hood 2, the tip end of the cylindrical main body portion 5 is cut at right angles, and a tip-end aperture 188 opened forwards is formed in the side wall. A cutout 189 connected to the tip-end aperture 188 is disposed in the tip end of the cylindrical main body portion 5. Additionally, instead of the cutout 189, a side aperture may be formed in the shape of a hole separated from the tip-end aperture 188 in the side wall.

The hood 2 includes the in-tissue inserting portion 8 projecting forwards in the region of the cutout 189. The in-tissue inserting portion 8 is a member which substantially has an "L" transverse sectional shape with two leg portions having an equal length, the tip end of the in-tissue inserting portion 8 is obliquely cut, and the tip end thereof is tapered.

As shown in FIG. 38, the in-tissue inserting portion 8 is prepared by bending a stainless steel plate coated with the ceramic coat substantially at 90 degrees, and is bonded/fixed to the hood 2. Additionally, the in-tissue inserting portion 8 may be a halved pipe having a semicircular sectional shape.

Moreover, the high-frequency knife 187 is formed by twisting the tip end of a steel strip 190 and sharpening the tip end thereof. The high-frequency knife 187 excluding only the tip end is coated with the insulation coat. A portion behind a twisted portion (loop) 191 of the high-frequency knife 187 is gently curled. The high-frequency knife 187 can be contained in a sheath 192. When the high-frequency knife 187 is pulled toward the hand side, the knife is contained in the sheath 192. The sheath 192 is formed of a resin having high electrical insulation, such as a fluorine resin.

In the portion behind the steel strip 190, a torque transmission tube 193 is formed of a meshed steel wire coated with a tube so that torque is easily transmitted.

Additionally, instead of the torque transmission tube, a multi-wound coil may be used. In this case, a cable for supplying a high-frequency current is contained in the middle of the coil.

The action of the twelfth embodiment will next be described. After the sheath 192 is projected from the treatment instrument insertion passage 69 in the body cavity, the high-frequency knife 187 is removed from the sheath 192. Then, in order to allow the tip end of the high-frequency knife 187 to contact the inside of the bent portion in the vicinity of the tip end of the in-tissue inserting portion 8, the sheath 192 is moved forwards/backwards and rotated, the high-frequency knife 187 is rotated, and the sheath and knife are positioned.

Subsequently, the high-frequency knife 187 is once pulled and contained in the sheath 192.

Subsequently, the in-tissue inserting portion 8 is inserted into the small incision formed beforehand.

Subsequently, by the angle operation of the endoscope 10, the mucosa 62 is scooped up by the in-tissue inserting portion 8. In this case, the position of the in-tissue inserting portion 8 under the mucosa 62 is checked with the endoscope image and the mucosa 62 is extended with tension.

Next, the high-frequency knife 187 is slowly removed from the sheath 192. Then, the high-frequency knife 187 is bent, the tip end of the high-frequency knife 187 contacts the mucosa 62, power is supplied and the sheath 192 is pulled. Alternatively, while power is supplied, the inserting portion 11 of the endoscope 10 is pulled without pulling the sheath 192. Then, the mucosa 62 held between the tip end of the high-frequency knife 187 and the in-tissue inserting portion 8 cuts.

In this case, the high-frequency knife 187 is positioned beforehand. Therefore, when the high-frequency knife 187 is taken out, the mucosa 62 is held between the high-frequency knife 187 and the in-tissue inserting portion 8 in the vicinity of the tip end of the in-tissue inserting portion 8.

Here, another example of the method of incising the mucosa will be described with reference to FIGS. 40 to 42. The apparatus shown in FIG. 40 is constituted of a laser probe 195. The tip end of the laser probe 195 is curled. By operation on the hand side, the laser probe 195 can be rotated while projecting from an outlet of the treatment instrument insertion passage 69 of the endoscope 10. Moreover, the laser probe 195 may freely be curled with the fingers.

Moreover, in the apparatus shown in FIG. 41, a cap 196 is disposed on the tip end of the laser probe 195, a mirror 197 is obliquely attached to the cap 196, and an outgoing direction of light emitted via the mirror 197 can obliquely be bent. An attachment angle of the mirror 197 can be adjusted at a free angle via a hinge 198 with fingers. Of course, the angle of the mirror 197 may remotely be operated by a wire operation from the outside of the body cavity. Moreover, the mirror 197 attached to the cap 196 at a variable angle may be replaced in accordance with the size of the affected area.

Furthermore, as shown in FIG. 42, the tip end of the laser probe 195 is obliquely formed so that light may be emitted in an oblique direction. Moreover, the laser probe 195 may be constituted such that the tip end thereof is cut off at a free angle in accordance with the size of the affected area with blades such as a cutter.

Additionally, for the rotation of the laser beam, in addition to the rotation of the probe 195, the mirror 197 may also be rotated.

An incising method using the probe 195 will next be described. A solution which absorbs the laser beam having a specific wavelength beforehand, and prevents the muscle layer positioned deeper than the solution from being incised is injected under the mucosa of a seat of disease. For example, physiological saline mixed with indocyanine green (ICG) is suitable for semiconductor laser.

Thereby, the mucosa layer is separated from the muscle layer, and only the mucosa is cut without damaging the muscle layer.

Subsequently, the locally injected portion is irradiated with the laser beam such as a semiconductor laser beam and the mucosa is cut. In this case, first the portion is irradiated with a low-energy guiding laser beam (beam serving as a pointer instead of a pilot rod, such as ruby laser), a beam trace is drawn around the seat of disease, and the position to be incised may be targeted.

Subsequently, the mucosa is quickly irradiated with a high-energy laser beam, and cut in a circular form. In this case, attention is paid so that the tip-end position of the probe 195 is not changed.

Moreover, in this case, since the injected solution having the specific color absorbs the energy of the laser beam, only the mucosa is correctly incised, and the muscle layer is not damaged.

According to the incising method, even a large seat of disease can safely be incised.

(Thirteenth Embodiment)

FIGS. 43 to 52 show the treatment apparatus for the endoscope according to a thirteenth embodiment.

Figure 43A:
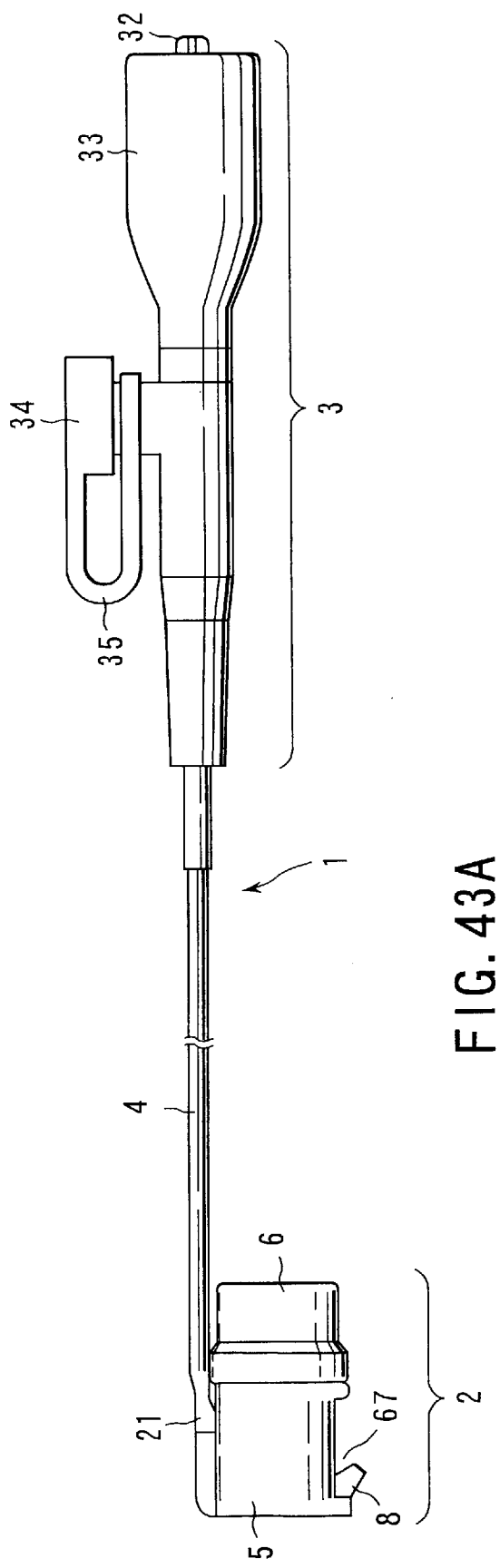
FIG. 43A is a side view of the whole treatment apparatus for the endoscope according to a thirteenth embodiment of the present invention.
Figure 43B:
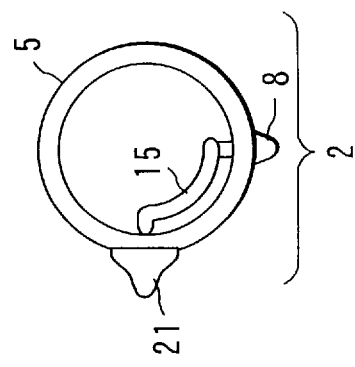
FIG. 43B is a front view of the tip end portion.

As shown in FIG. 43, the treatment apparatus for the endoscope according to the thirteenth embodiment is formed as the high-frequency incising apparatus 1, and includes the hood 2 to be inserted into the body, connector 3, and cable 4 for connecting the hood 2 to the connector 3. The cable 4 may be a thermally contractible tube.

The hood 2 is constituted of the cylindrical main body portion 5 and attaching portion 6. The cylindrical main body portion 5 is formed of the material similarly as described above in a substantially cylindrical shape. The cylindrical main body portion 5 has an outer diameter of 8 mm to 18 mm, and inner diameter of 6 mm to 16 mm. Furthermore, the attaching portion 6 is a soft cylindrical member, and formed of soft materials such as rubber materials including silicon rubber, PVC, and thermoplastic elastomer. The attaching portion 6 has an inner diameter such that the portion can closely be attached to the tip-end portion 12 in the inserting portion 11 of the endoscope 10, and is attachable/detachable with respect to the tip-end portion 12.

Figure 46:
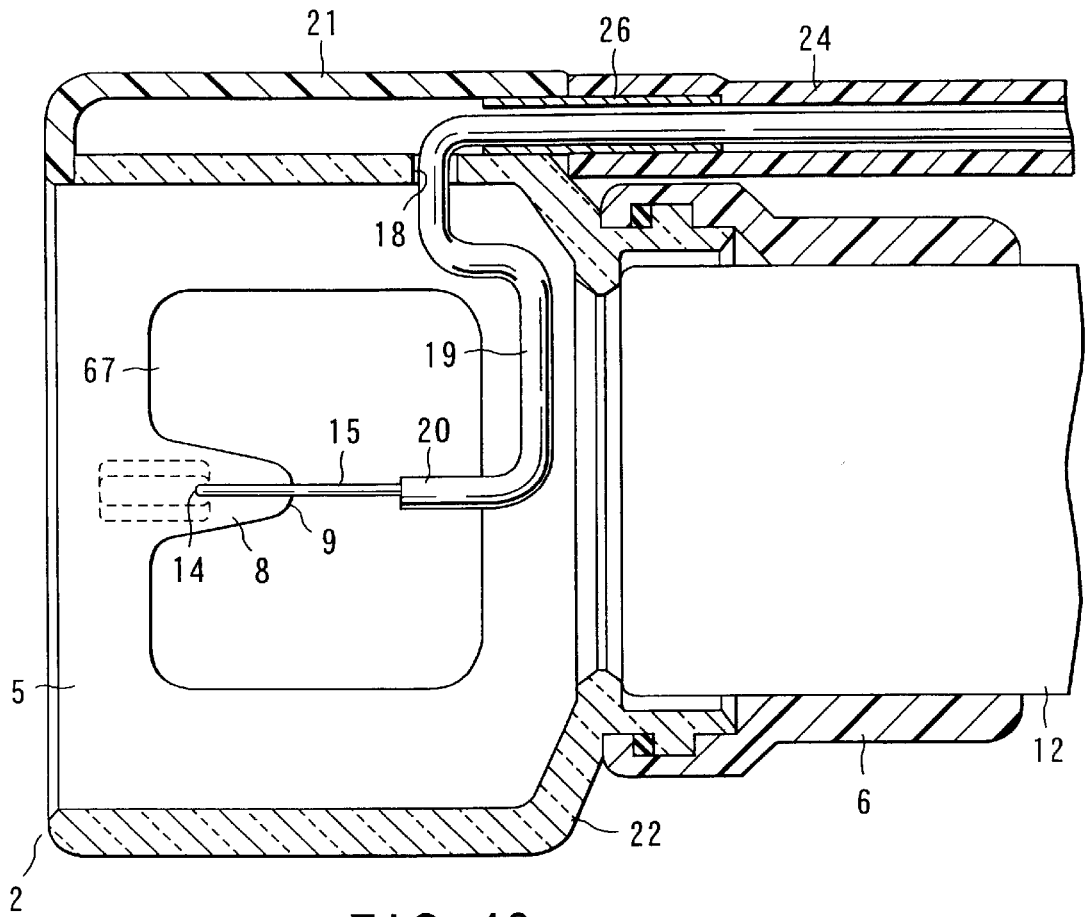
FIG. 46 is a longitudinal sectional view of the vicinity of the hood of the treatment apparatus of FIG. 45 along the plane substantially vertical to a sheet surface of FIG. 45.
Figure 47:
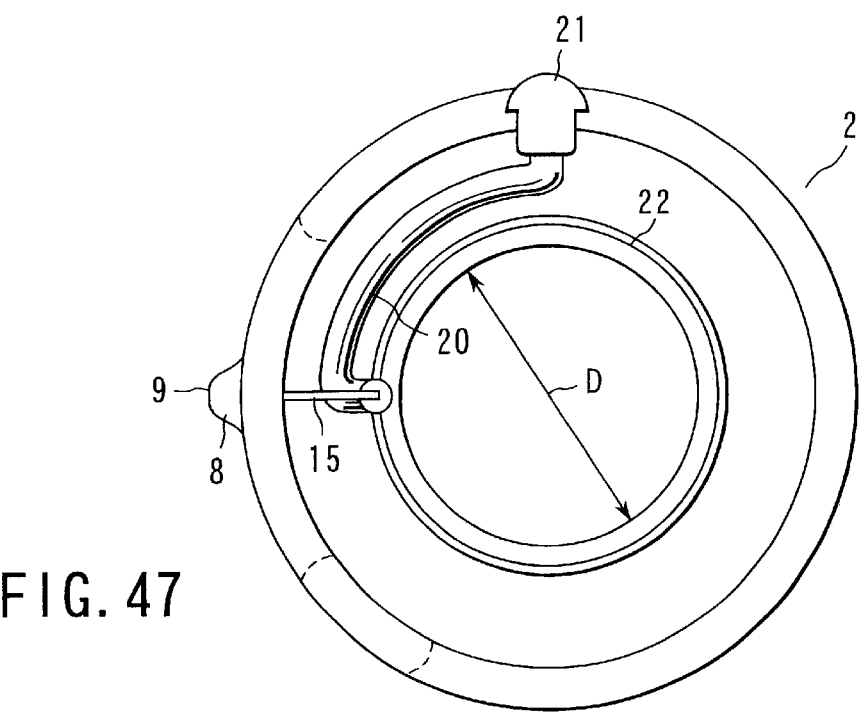
FIG. 47 is a transverse sectional view of the hood of the treatment apparatus shown in FIG. 45.

As shown in FIG. 46, the side aperture 67 as the opening is disposed in the side wall of the cylindrical main body portion 5, and the tongue-shaped in-tissue inserting portion 8 projecting toward the base end is integrally disposed on the tip edge of the side aperture 67.

Moreover, for the size of the side aperture 67, the width is preferably in the range of 1 mm to 10 mm, and the length is 3 mm to 10 mm. Furthermore, the in-tissue inserting portion 8 is elongate, and sharpened toward the tip end, and the tip end 9 of the in-tissue inserting portion 8 is rounded.

The in-tissue inserting portion 8 preferably has a length of 1 mm to 5 mm. Moreover, the thickness of the in-tissue inserting portion 8 is preferably in the range of 0.5 to 2 mm in a root portion, and 0.1 to 0.5 mm in the tip-end portion. Furthermore, the width of the in-tissue inserting portion 8 is preferably in the range of 1 mm to 8 mm in the root portion, and 0.5 mm to 4 mm in the tip-end portion. Moreover, the in-tissue inserting portion 8 may have an elliptical, quadrangular or triangular shape, as long as the shape is elongate.

Figure 45:
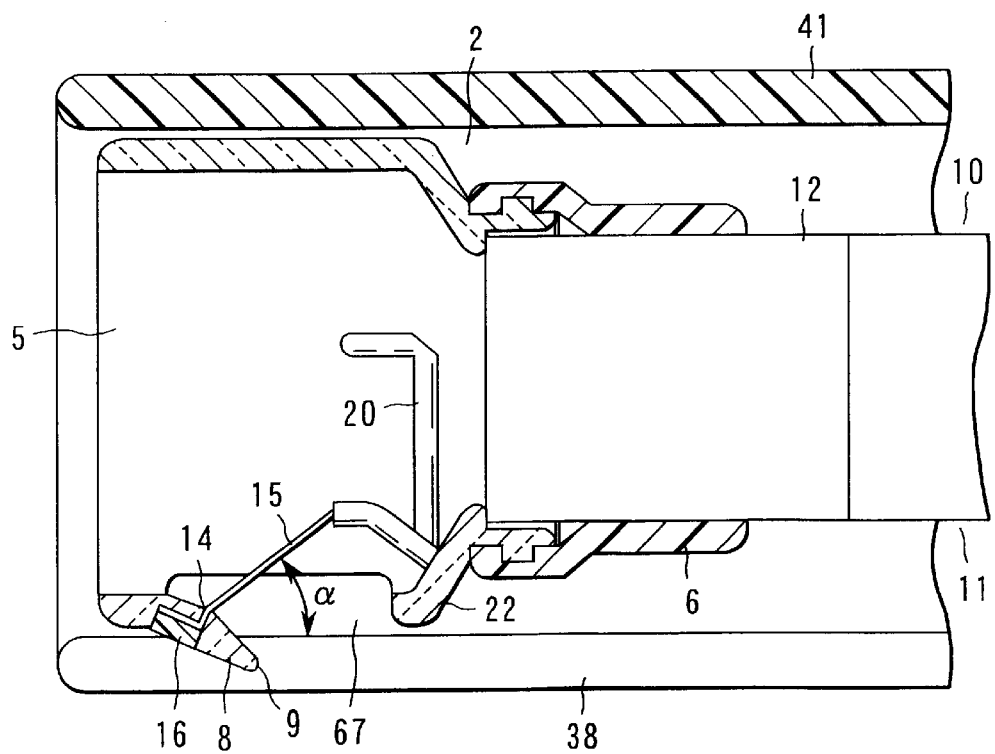
FIG. 45 is a longitudinal sectional view of the vicinity of the hood of the treatment apparatus for the endoscope according to the thirteenth embodiment of the present invention.

As shown in FIG. 45, the in-tissue inserting portion 8 projects outwardly from the outer peripheral surface of the cylindrical main body portion 5. The projecting amount of the in-tissue inserting portion 8 to the outside is in the range of 0.1 mm to 10 mm.

Figure 52:
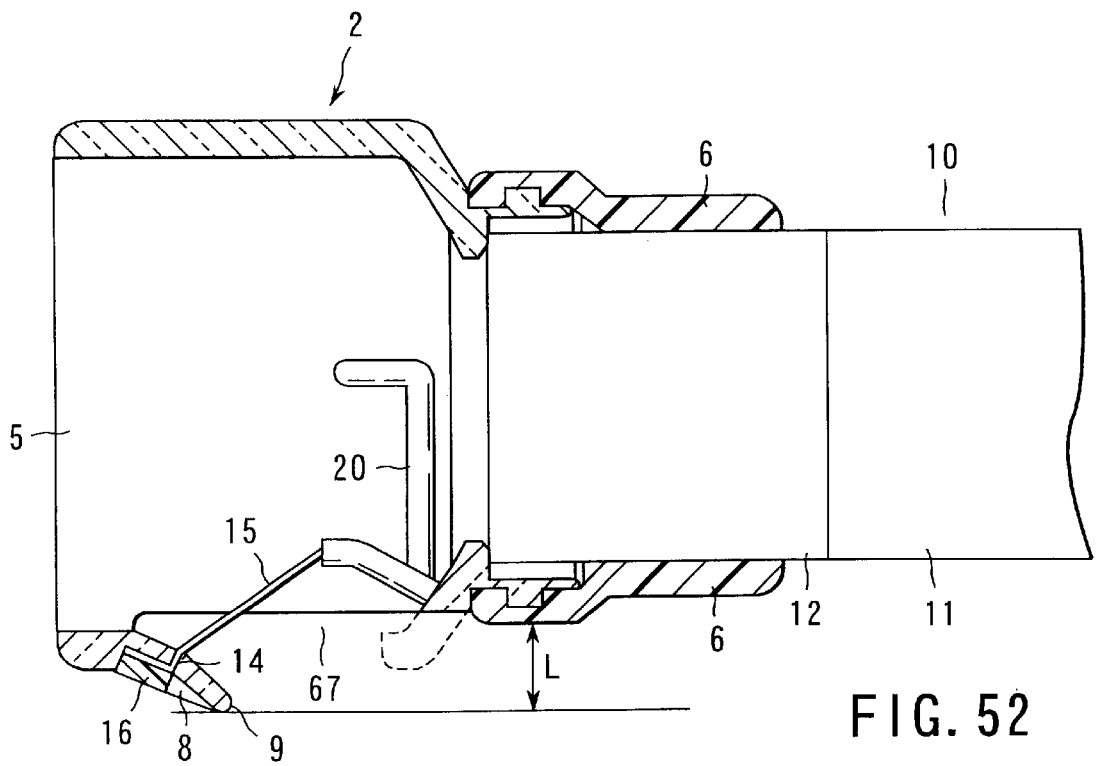
FIG. 52 is an explanatory view showing a projecting amount of an in-tissue inserting portion 8 of the treatment apparatus shown in FIG. 45.

Moreover, the in-tissue inserting portion 8 is integral with the 05, but does not have to be integral, and may be attached to the cylindrical main body portion 5 with the adhesive. In this case, the in-tissue inserting portion 8 may be formed of the material other than that of the cylindrical main body portion 5. Furthermore, as shown in FIG. 52, a portion of the cylindrical main body portion 5 shown by a broken line may be cut off. Thereby, a projecting amount L of the in-tissue inserting portion 8 to the outside increases, and the in-tissue inserting portion 8 can more easily be inserted under the mucosa.

The small hole 14 is made in the in-tissue inserting portion 8. The tip end of the incision line 15 formed of the metal wire superior in conductivity, such as stainless steel and gold is inserted into the hole 14 from the inside, and bent outside. The bent portion is covered with the wire cover portion 16 from the outside, and the incision line is bonded/fixed to the in-tissue inserting portion 8.

Moreover, the small hole 14 is positioned 0.5 to 3 mm from the tip end of the in-tissue inserting portion 8. Furthermore, the outer diameter of the incision line 15 is in the range of 0.05 mm to 3 mm, preferably 0.15 mm to 0.3 mm.

Additionally, the wire cover portion 16 is formed by the material superior in high-frequency resistance and electrical insulation similarly as the cylindrical main body portion 5. Connection means of the wire cover portion 16 to the in-tissue inserting portion 8 is not limited to adhesion, and other bonding methods such as thermal welding may be used.

Moreover, the incision line 15 is formed by stripping and exposing the conductive portion of the coated line 20 by an optional distance from the contact with the in-tissue inserting portion 8. Furthermore, the portion of the incision line 15 from which the conductive portion is exposed has a length of 1 mm to 10 mm. For the other portion, the surface of the conductive portion is coated with the electrical insulation coat 19 such as the fluorine resin. The electrical insulation coat 19 preferably has a thickness of the order of 0.5 mm to 1 mm. Moreover, as shown in FIG. 45, the angle α of the incision line 15 to the mucosa is in the range of 0° to 180°, preferably 15° to 75°.

Therefore, as shown in FIG. 45, the incision line 15 is disposed so that the line first extends in the axial direction from the contact with the in-tissue inserting portion 8, and thereafter the portion of the coated line 20 coated with the electrical insulation coat 19 is positioned outside a minimum diameter D (see FIG. 47) in a base-end portion 22 and in the vicinity of the base-end portion 22 of the cylindrical main body portion 5. Thereby, the coated line 20 does not obstruct the endoscopic view field, and further the coated line 20 does not hinder the treatment instrument from being moved forwards/backwards from the tip-end portion 12 of the endoscope 10. The guided coated line 20 is passed through the side hole 18 of the cylindrical main body portion 5 and bent, further passed through the cable 4, guided into the connector 3, and connected to the high-frequency power supply.

The portion of the coated line 20 passed through the side hole 18 and connected to the connector 3 is covered with the tube sheath 24 of the cable 4. Thereby, current is prevented from leaking into the body. The tube sheath 24 is formed of the material superior in electrical insulation such as the fluorine resin. For the size of the tube sheath 24, the inner diameter is preferably in the range of 0.5 mm to 2 mm, and the thickness is of the order of 0.1 mm to 1 mm. The tube sheath 24 extends to the base end from the bonded portion with the wire presser 21, and is connected to the connector 3. The wire presser 21 is connected to the tube sheath 24 via the intermediary pipe 26.

Moreover, outside the cylindrical main body portion 5, the wire presser 21 superior in electrical insulation is disposed to cover the coated line 20 from the outside. The wire presser 21 may be integral with the cylindrical main body portion 5.

Figure 48:
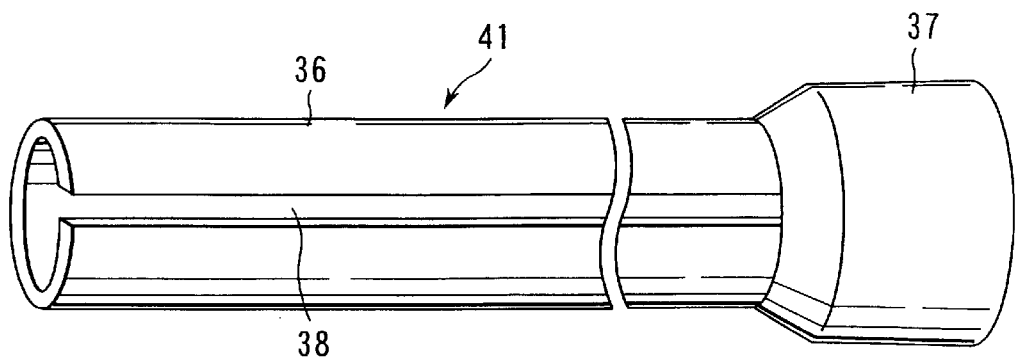
FIG. 48 is a perspective view of the over tube for use in the treatment apparatus shown in FIG. 45.

The constitution of the over tube 41 for use in guiding the endoscope 10 with the high-frequency incising apparatus 1 attached thereto into the body will next be described. As shown in FIG. 48, the over tube 41 is constituted of a tube main body 36 and an endoscope insertion port 37 connected to the base end of the main body. The tube main body 36 is formed of polyurethane, vinyl chloride, or preferable resins such as the fluorine resin. Moreover, to facilitate the insertion into the body, and the rotation of the endoscope 10, the tube main body 36 is more preferably formed of a material superior in slippage, such as the fluorine resin. Furthermore, the tube main body 36 has an outer diameter of 12 mm to 20 mm, especially preferably 15 mm to 18 mm. The inner diameter of the tube main body 36 is not limited as long as the inserting portion 11 of the endoscope 10 can be inserted through.

A slit 38 formed along the axial direction is disposed in the tube main body 36. When the slit 38 is disposed, and the hood 2 is inserted into the tube main body 36, as shown in FIG. 45, the in-tissue inserting portion 8 projecting outwards enters the slit 38. Therefore, the hood 2 can be inserted into the tube main body 36 without increasing the inner/outer diameter of the tube main body 36. Therefore, the width of the slit 38 is in the range of 1 mm to 9 mm, especially preferably 2 mm to 5 mm.

Figure 44:
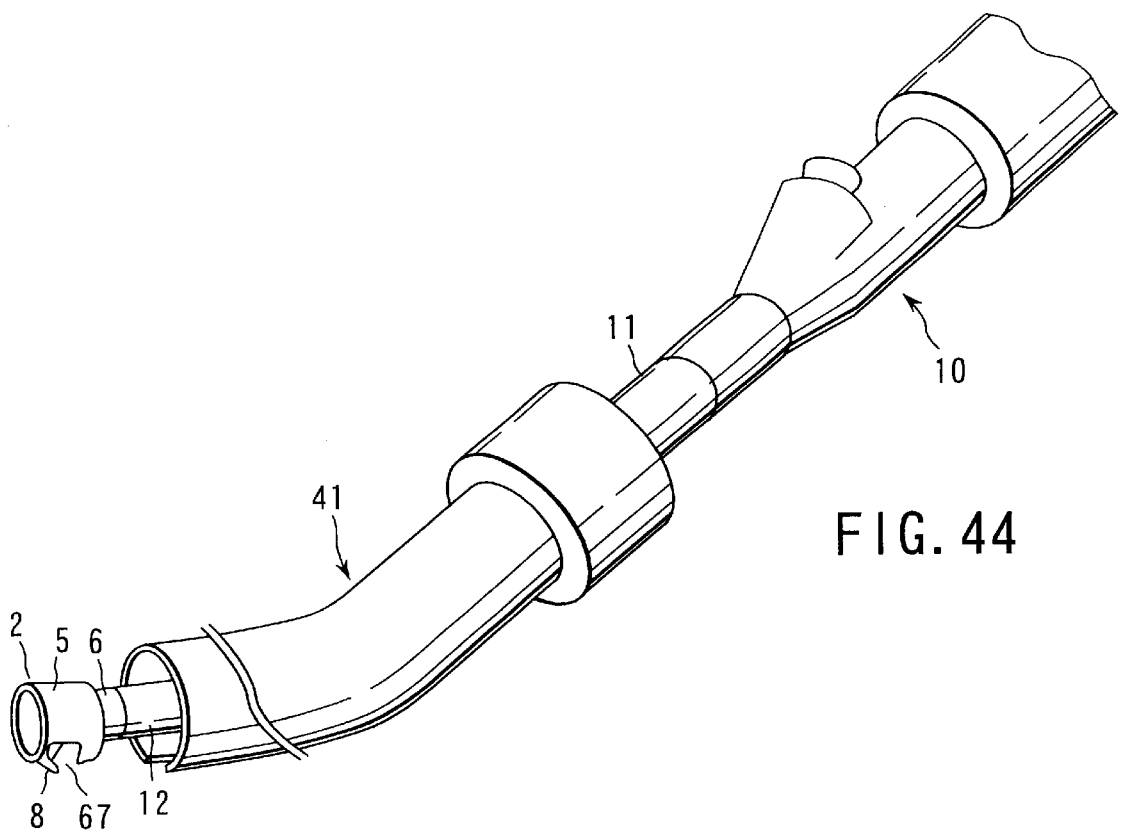
FIG. 44 is a perspective view of the use state of the inserting portion of the endoscope with the high-frequency treatment apparatus for the endoscope attached thereto and the over tube for guiding the inserting portion of the endoscope into a body.

The high-frequency incising apparatus for the endoscope according to the thirteenth embodiment will next be described. First, as shown in FIG. 44, the hood 2 is attached to the tip-end portion 12 of the endoscope 10. Thereafter, the cable 4 is fixed to several positions of the inserting portion 11 of the endoscope 10 with the medical tape. This fixed state is not shown.

After the preparation, as shown in FIG. 44, the endoscope 10 is inserted into the over tube 41. Furthermore, the connector 3 and high-frequency power supply (not shown) are connected via a power cord (not shown).

Subsequently, after the over tube 41 with the high-frequency incising apparatus 1 attached thereto is inserted into the body cavity, only the high-frequency incising apparatus 1 is moved forwards to target parts of the lumen organ, such as esophagus, duodena, small intestine, and large intestine, together with the endoscope 10.

When the portion of the hood 2 of the high-frequency incising apparatus 1 reaches the target part such as the lumen organ, a syringe needle (not shown) is used to inject the physiological saline under the mucosa of the target part, the connective tissue 64 between the mucosa 62 and muscle layer 63 is allowed to absorb the physiological saline, and the connective tissue 64 is expanded. Then, the mucosa 62 is detached from the muscle layer 63, expanded in the bump shape, stretched, and easily cut.

Subsequently, the needle-shaped scalpel (not shown) adds the small incision 65 to the mucosa 62 expanded in the bump shape. The mucosa is expanded in the bump shape by the physiological saline. Therefore, when the needle-shaped scalpel is used to add the small incision 65 to the mucosa 62, the muscle layer 63 is not damaged.

Figure 49:
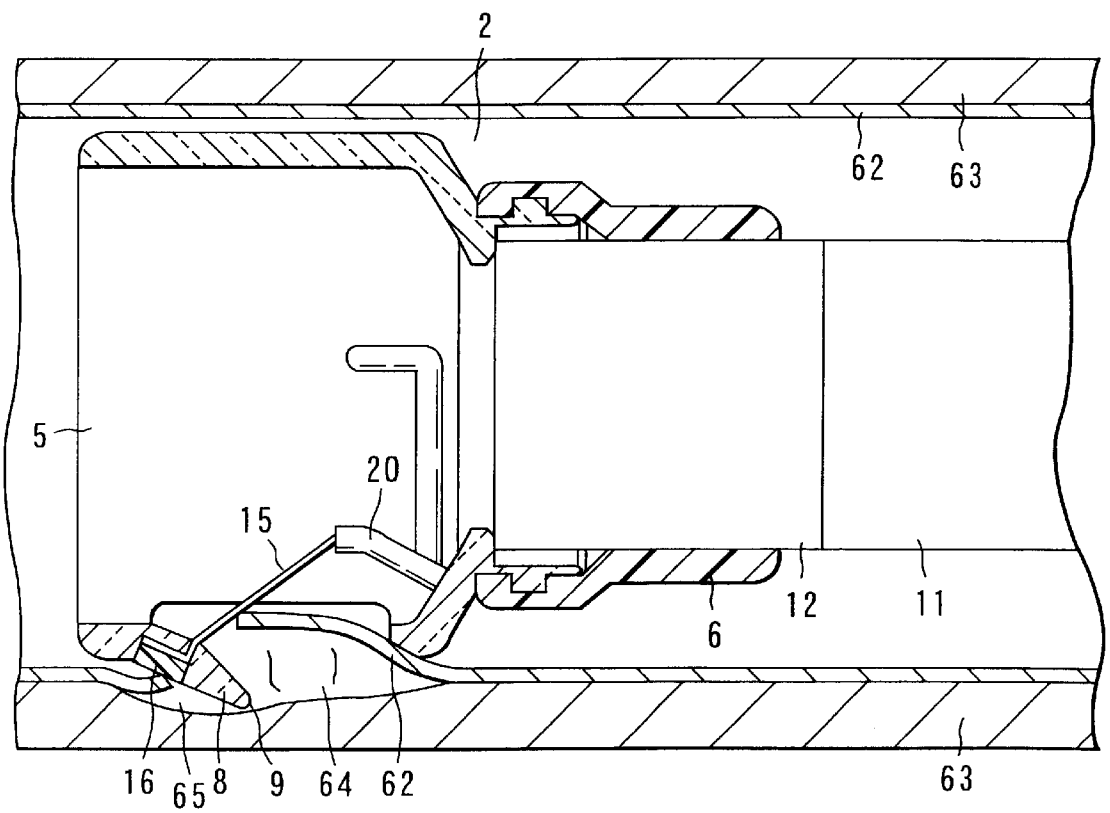
FIG. 49 is a longitudinal sectional view of the use state of the treatment apparatus shown in FIG. 45.
Figure 50:
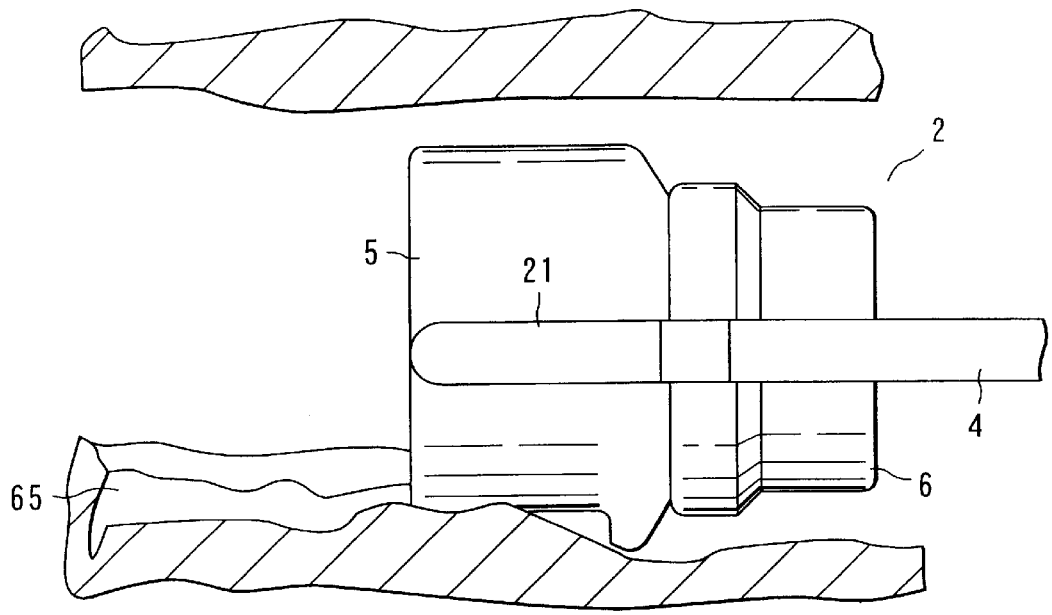
FIG. 50 is an explanatory view of the use state of the treatment apparatus shown in FIG. 45.

By the forward/backward moving operation of the inserting portion 11 of the endoscope 10 and the bending operation of the inserting portion 11 of the endoscope 10, the in-tissue inserting portion 8 is positioned above the small incision 65. Thereafter, by the forward/backward moving operation of the inserting portion 11 of the endoscope 10, as shown in FIGS. 49 and 50, the tip end 9 of the in-tissue inserting portion 8 is slipped/inserted via the small incision 65 formed by the needle-shaped scalpel. In this case, the inserting portion 11 is moved forwards/backwards while performing the sucking operation of the endoscope 10, so that the tip end 9 of the in-tissue inserting portion 8 easily comes under the mucosa 62.

Moreover, since the tip end 9 of the in-tissue inserting portion 8 is formed to be round, the backside of the mucosa 62 and the muscle layer 63 are not damaged. Additionally, the muscle layer 63 is not pierced.

After the in-tissue inserting portion 8 is slipped into the small incision 65, the inserting portion 11 of the endoscope 10 is pulled toward the hand side so that the mucosa 62 closely adheres to the incision line 15. Thereafter, when power is supplied to the incision line 15, the mucosa 62 closely adhering to the incision line 15 is cut. Additionally, even when the portion having the electrical insulation coat 19 contacts the mucosa 62, the mucosa is not cut.

When the above-described operation is repeated, the inner wall of the lumen organ is incised at two left and right places of the affected area in the axial direction. Thereafter, when the rear side and anal side of the affected area are transversely incised with the needle-shaped scalpel, a rectangular incision surrounding the region including the affected area is incised. Of course, the order of the adding of the axial incision and transverse incision is not limited.

Figure 51:
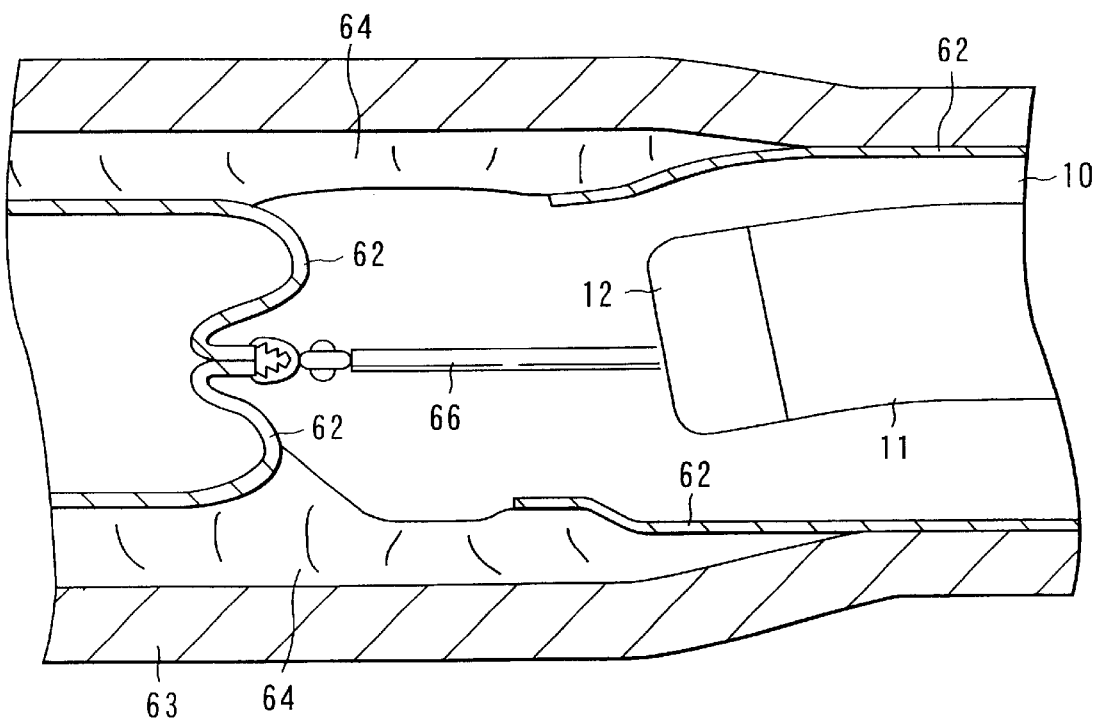
FIG. 51 is an explanatory view of a state in which the treatment apparatus shown in FIG. 45 is used to recover the incised mucosa.

After the mucosa 62 is incised in the rectangular shape, the physiological saline is injected into the corresponding part and the part is separated from the muscle layer 63. Thereafter, as shown in FIG. 51, the mucosa 62 is stripped/collected by the grip forceps 66.

According to the thirteenth embodiment, the safe and easy method is possible in the axial incision. Since the window width of the side aperture 67 is sufficiently narrow, the wire-shaped incision line 15 can constantly and strongly be pressed onto the mucosa 62 without turning over the mucosa 62 during the incision and the incision is facilitated. The nail-shaped in-tissue inserting portion 8 projects in a direction in which the mucosa 62 is scooped. Therefore, the tip end 9 of the in-tissue inserting portion 8 is easily inserted under the mucosa 62, and the tip end 9 of the in-tissue inserting portion 8 can be pushed forwards between the mucosa 62 and muscle layer 63. The in-tissue inserting portion 8 can easily incise the mucosa without being caught by the mucosa 62.

(Fourteenth Embodiment)

Figure 53:
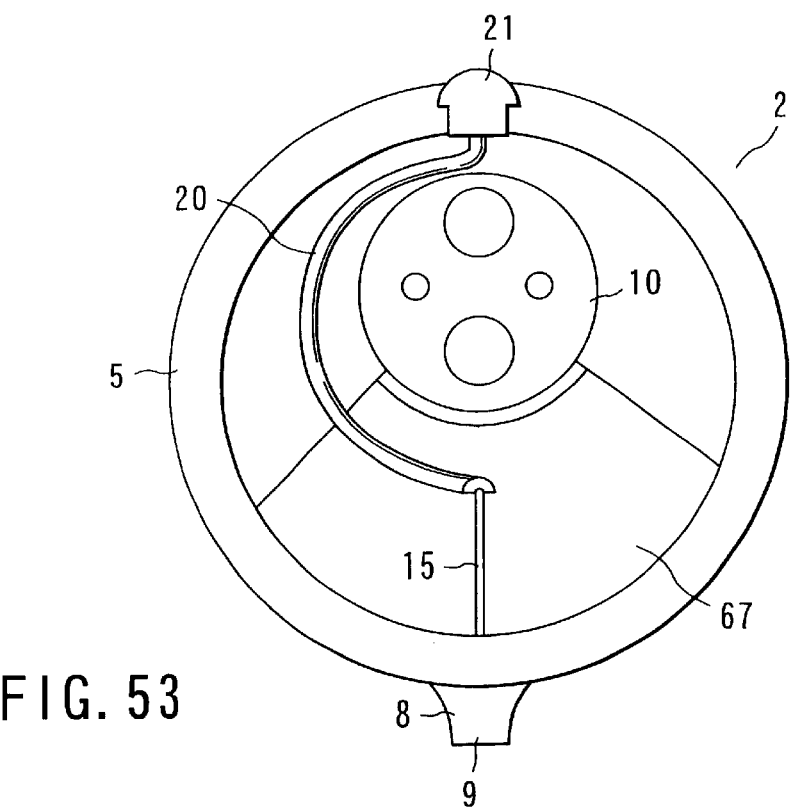
FIG. 53 is a front view in the use state of the treatment apparatus for the endoscope according to a fourteenth embodiment of the present invention.
Figure 54:
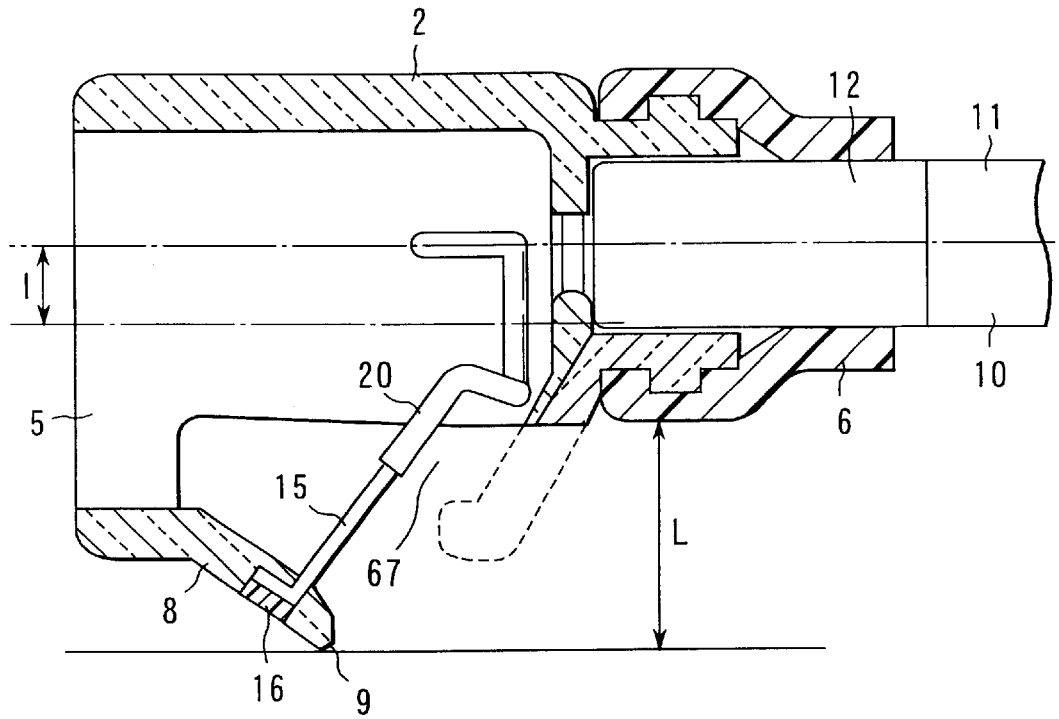
FIG. 54 is a longitudinal sectional view in the use state of the treatment apparatus shown in FIG. 53.
Figure 55:
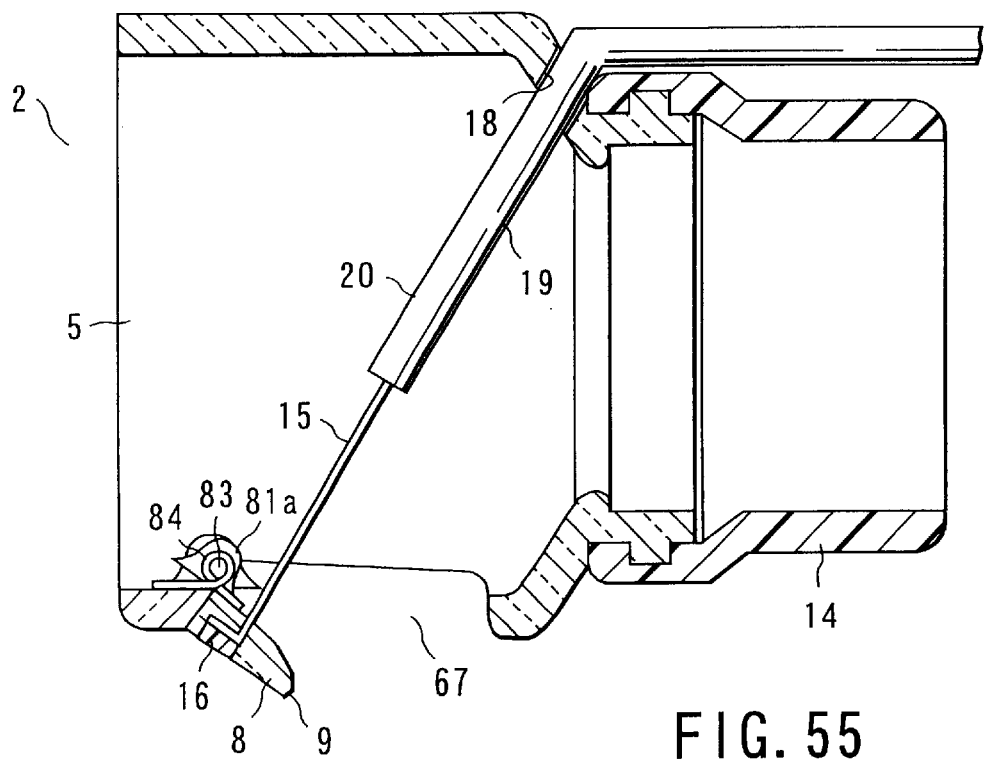
FIG. 55 is a longitudinal sectional view of the hood of the high-frequency treatment apparatus for the endoscope according to a fifteenth embodiment of the present invention.

FIGS. 53 and 54 show the treatment apparatus for the endoscope according to a fourteenth embodiment. The treatment apparatus is formed as the high-frequency incising apparatus for the endoscope similar to that of the thirteenth embodiment in broad terms.

Moreover, in the high-frequency incising apparatus for the endoscope according to the fourteenth embodiment, as shown in FIG. 54, the cylindrical main body portion 5 of the hood 2 becomes eccentric sideways by an optional distance 1 with respect to a transverse section center of the tip-end portion 12 of the endoscope 10. The distance 1 is preferably in the range of 0.1 mm to 10 mm.

Since the main body portion is eccentric as described above, the projecting amount L of the in-tissue inserting portion 8 in FIG. 52 in the thirteenth embodiment is kept to be the same, and the outer diameter of the cylindrical main body portion 5 can be reduced by the distance 1 as shown in FIG. 54. Therefore, the inserting portion can more easily be inserted/detached with respect to the body cavity. The other action and effect are the same as those of the thirteenth embodiment.

(Fifteenth Embodiment)

FIGS. 55 to 64 show the treatment apparatus for the endoscope according to a fifteenth embodiment. The treatment apparatus is formed as the high-frequency incising apparatus for the endoscope similar to that of the thirteenth embodiment in broad terms.

Figure 56:
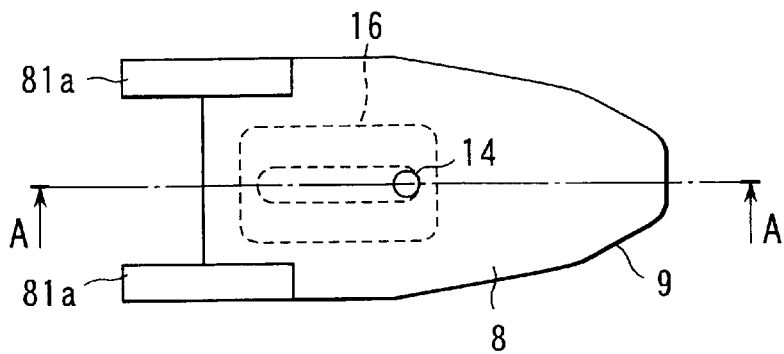
FIG. 56 is a front view of the in-tissue inserting portion of the treatment apparatus shown in FIG. 55.
Figure 57:
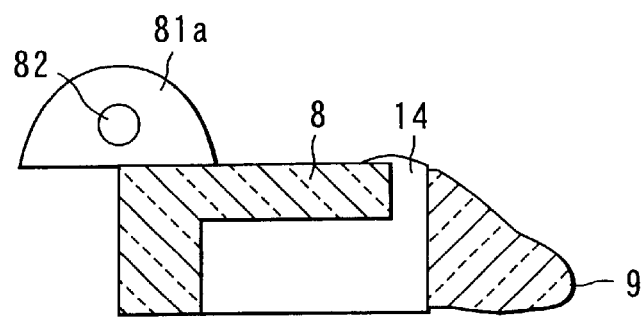
FIG. 57 is a longitudinal sectional view of the in-tissue inserting portion.
Figure 58:
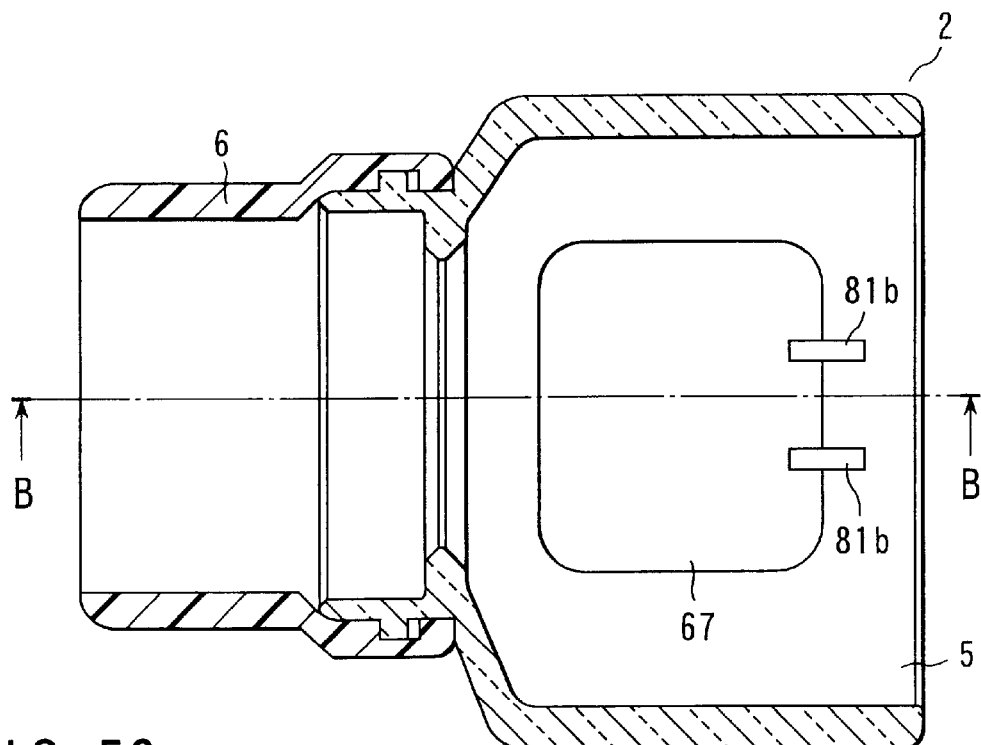
FIG. 58 is a sectional view of the hood of the treatment apparatus shown in FIG. 55 along the plane substantially vertical to the sheet surface of FIG. 55.
Figure 59:
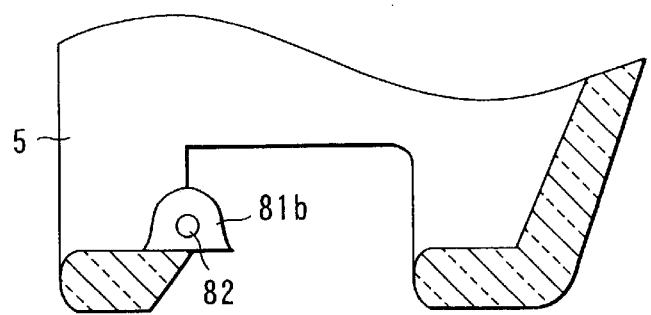
FIG. 59 is a partial enlarged sectional view of the hood of the treatment apparatus shown in FIG. 55.
Figure 60:
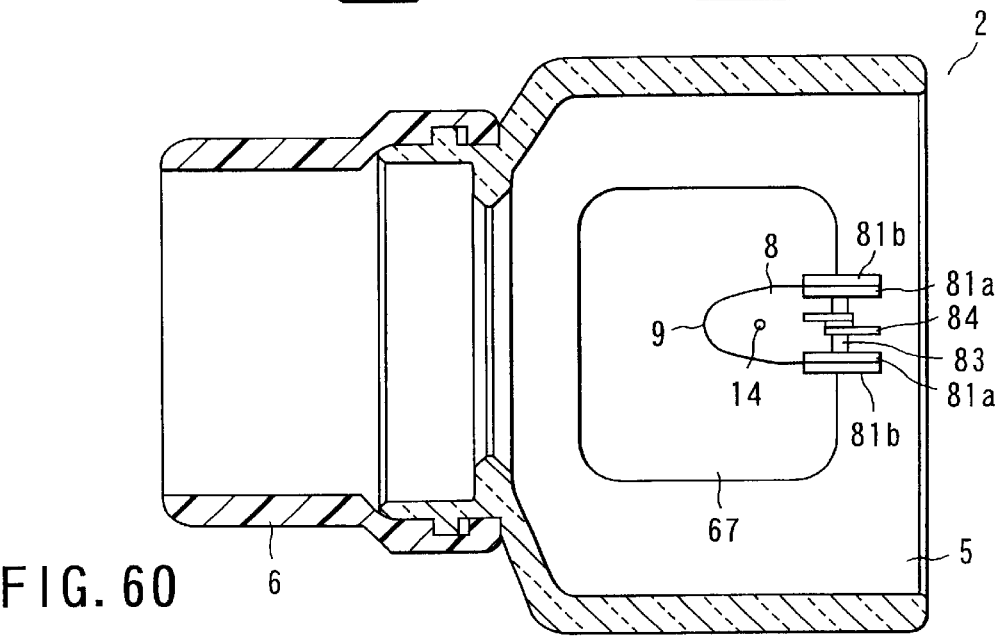
FIG. 60 is a sectional view similar to FIG. 58, in a state in which the in-tissue inserting portion is attached.

Moreover, in the high-frequency incising apparatus for the endoscope in the fifteenth embodiment, the cylindrical main body portion 5 of the hood 2 is separate from the in-tissue inserting portion 8, and the in-tissue inserting portion 8 can be projected/retrojected with respect to the outer surface of the cylindrical main body portion 5. As shown in FIGS. 56 and 57, the in-tissue inserting portion 8 includes support pieces 81*a* fixed to the base-end inner surface, and as shown in FIG. 59, the cylindrical main body portion 5 includes support pieces 81*b* fixed to the inner surface. Axial holes 82 are formed in the respective support pieces 81*a*, 81*b*. As shown in FIG. 60, an axial pin 83 is inserted through the axial holes 82 of the respective support pieces 81*a*, 81*b* so that the in-tissue inserting portion 8 is axially supported by the cylindrical main body portion 5. The axial pin 83 is fixed to the support pieces 81*b*, and is rotatable with respect to the support pieces 81*a*. Furthermore, the outer periphery of the axial pin 83 is wound with a spring 84. One end of the spring 84 abuts on and stops at the inner surface of the in-tissue inserting portion 8, and the other end of the spring 84 abuts on and stops at the inner surface of the cylindrical main body portion 5. The spring 84 is positioned between two left and right support pieces 81*a*, 81*b*, and is bias means for applying a force to the in-tissue inserting portion 8 in the projecting direction.

That is, the in-tissue inserting portion 8 is always biased in an outwardly projecting direction. In this case, the bias force of the spring 84 is sufficient for projecting the in-tissue inserting portion 8. Moreover, when the coated line 20 is pulled, the in-tissue inserting portion 8 can easily be contained in the cylindrical main body portion 5. Therefore, the in-tissue inserting portion 8 is projected by the bias force of the spring 84, and the in-tissue inserting portion 8 is contained/retracted by pulling the coated line 20 toward the base end.

Figure 61:
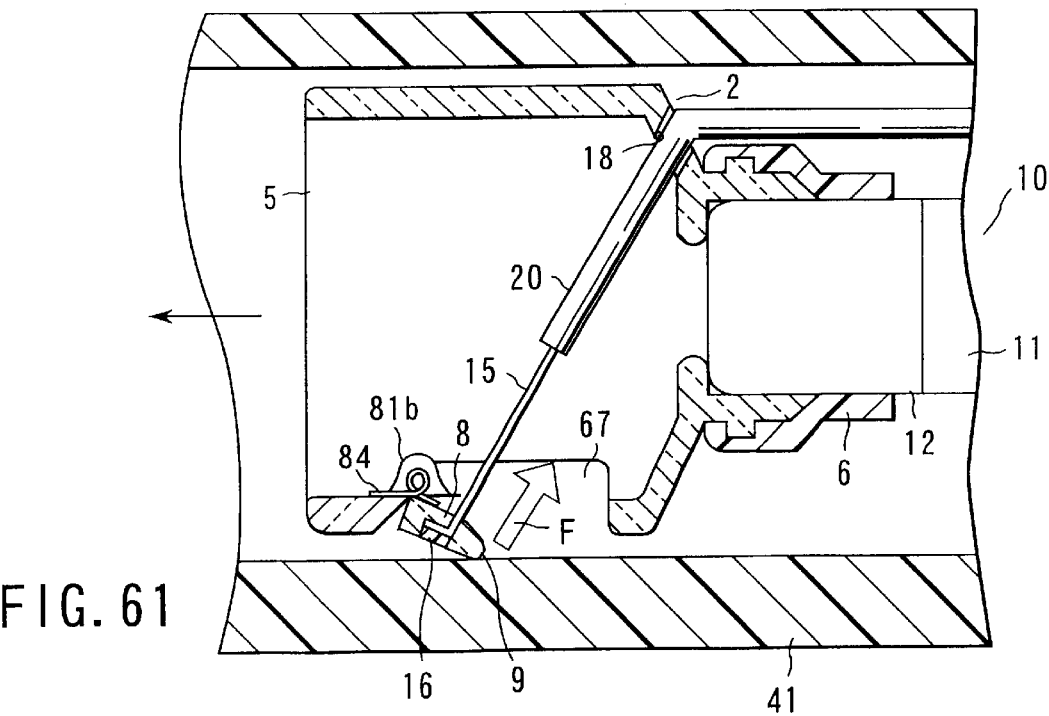
FIG. 61 is a longitudinal sectional view showing that the treatment apparatus shown in FIG. 55 is contained in the over tube.
Figure 62:
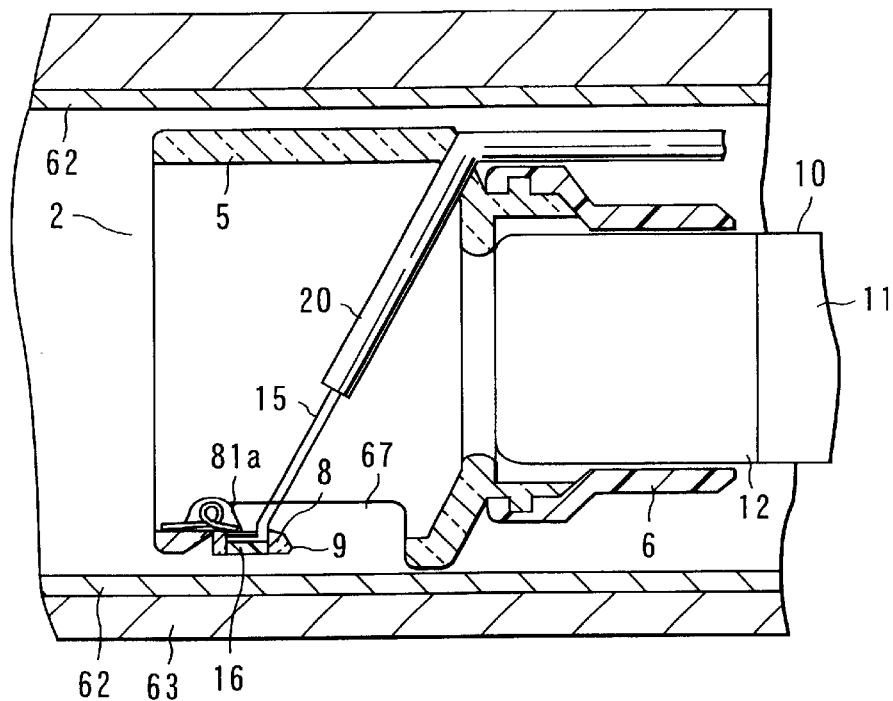
FIG. 62 is a longitudinal sectional view showing that the treatment apparatus shown in FIG. 55 is inserted in a body cavity.

The action of the hood 2 in the high-frequency incising apparatus for the endoscope of the fifteenth embodiment will be described. When the hood is inserted into the over tube 41, as shown in FIG. 61, the in-tissue inserting portion (claw) 8 receives a force F in a contained direction from the over tube 41, and is thereby rotated inwards and retracted into the cylindrical main body portion 5. The in-tissue inserting portion 8 can be rotated and retracted in this manner. Therefore, when the inserting portion 11 is simply pushed inwards, the portion can easily be inserted even to the over tube 41 having no slit.

Additionally, the method of forming the small incision 65 is the same as that of the fourteenth embodiment. When the tip end 9 of the in-tissue inserting portion 8 is inserted into the small incision 65, the automatic projection of the in-tissue inserting portion 8 by the bias force of the spring 84 is awaited. Thereafter, the tip end 9 of the in-tissue inserting portion 8 is inserted into the small incision 65 and the mucosa is incised in the axial direction.

After the incision, the coated line 20 is pulled by operation on the hand side. Then, the in-tissue inserting portion 8 rotates, and is contained in the cylindrical main body portion 5 of the hood 2 (see FIG. 62). Thereafter, the high-frequency incising apparatus is extracted through the over tube 41. The subsequent stripping/collecting method of the mucosa is the same as that of the fourteenth embodiment.

According to the fifteenth embodiment, in the incision of the axial direction, the safe and easy method is possible. Moreover, since the in-tissue inserting portion 8 can be projected/retrojected, the in-tissue inserting portion 8 is moved backwards into the hood 2 during the inserting/detaching of the endoscope 10, and the endoscope can easily be inserted into the over tube 41 or the body.

Additionally, the fifteenth embodiment may be modified as follows. First, the support pieces 81*a* for connection may be formed integrally with the in-tissue inserting portion 8. When the pieces are separately formed, the pieces may be bonded/fixed to the in-tissue inserting portion 8. In this case, the support pieces 81*a* may be formed of materials other than those of the in-tissue inserting portion 8. Of course, the support pieces 81*b* may be formed integrally with or separately from the cylindrical main body portion 5 of the hood 2.

Moreover, the positions of the two support pieces 81*a*, 81*b* is not limited to a position in which the support piece 81*a* is held between the support pieces 81*b* during the assembling of the cylindrical main body portion 5 with the in-tissue inserting portion 8. Conversely, the support piece 81*b* may be positioned between the support pieces 81*a*.

The in-tissue inserting portion 8 is biased in the projecting direction by the spring 84. Conversely, the portion may be biased in a direction in which the portion is contained in the cylindrical main body portion 5. In the latter case, the in-tissue inserting portion 8 is projected by pushing the coated line 20 outwards toward the tip end, and the in-tissue inserting portion 8 is contained by the bias force of the spring 84. In this case, the bias force of the spring 84 is sufficient for containing the projected in-tissue inserting portion 8 in the cylindrical main body portion 5, and is sufficient to such an extent that the in-tissue inserting portion 8 is kept in a projected state by pushing the coated line 20 toward the tip end. Moreover, the mode of the biasing spring 84 is not limited to the above-described mode.

A method of connecting the cylindrical main body portion 5 to the in-tissue inserting portion 8 is not limited to the method shown in the drawing. Moreover, the spring 84 may be omitted. In this case, the in-tissue inserting portion 8 is projected/retrojected by moving the coated line 20 forwards/backwards on the hand side.

Moreover, the in-tissue inserting portion 8 and cylindrical main body portion 5 are integrally constituted, and formed of materials having elasticity and superior in electrical insulation and high-frequency resistance, such as rubber materials including silicon rubber, PVC, and thermoplastic elastomer. The in-tissue inserting portion 8 may be constituted to be elastically deformed.

Figure 63:
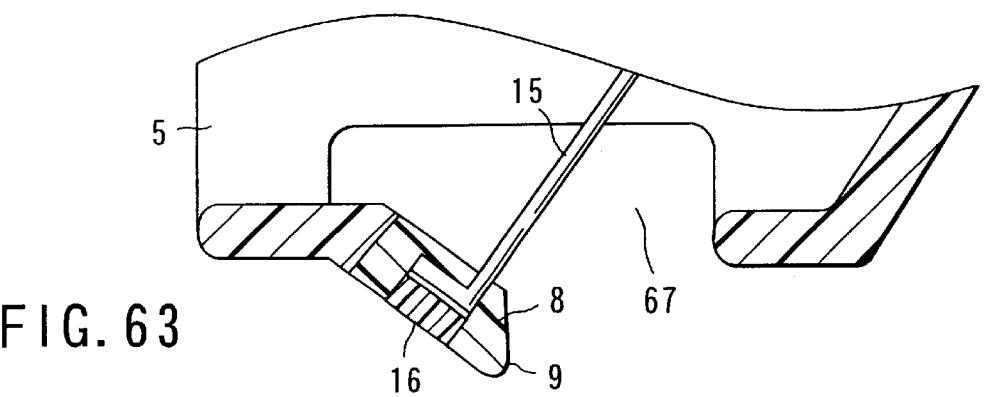
FIG. 63 is a longitudinal sectional view of the deformed in-tissue inserting portion of the treatment apparatus shown in FIG. 55.
Figure 64:
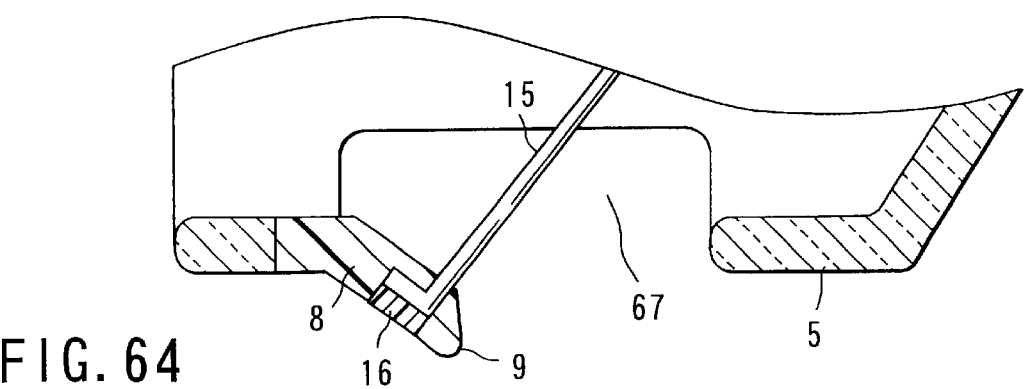
FIG. 64 is a longitudinal sectional view of another deformed in-tissue inserting portion of the treatment apparatus shown in FIG. 55.

Even in this case, the in-tissue inserting portion 8 and cylindrical main body portion 5 may separately be formed, and may be bonded/fixed to each other. For example, as shown in FIG. 63, the material having elasticity may be used in the material of the cylindrical main body portion 5, and the material superior in electrical insulation and high-frequency resistance may be used in the material of the in-tissue inserting portion 8. Alternatively, as shown in FIG. 64, a transparent material may be used in the material of the cylindrical main body portion 5, and the elastic material superior in insulation and high-frequency resistance may be used in the material of the in-tissue inserting portion 8.

In the former case, the in-tissue inserting portion 8 is projected by the elastic force of the cylindrical main body portion 5, and the in-tissue inserting portion 8 is contained by pulling the coated line 20 toward the base end. In this case, the elastic force of the material of the cylindrical main body portion 5 is sufficient for projecting the in-tissue inserting portion 8, and is sufficient to such an extent that the in-tissue inserting portion 8 is easily contained by pulling the coated line 20 toward the base end.

In the latter case, the in-tissue inserting portion 8 is projected by the elastic force of the in-tissue inserting portion 8, and the in-tissue inserting portion 8 is contained by pulling the coated line 20 toward the base end. In this case, the elastic force of the material of the in-tissue inserting portion 8 is sufficient for projecting the in-tissue inserting portion 8, and is sufficient to such an extent that the in-tissue inserting portion 8 is easily contained by pulling the coated line 20 toward the base end. Moreover, the shapes of the respective support pieces 81a, 81b are not limited to the above-described shapes.

(Sixteenth Embodiment)

Figure 65:
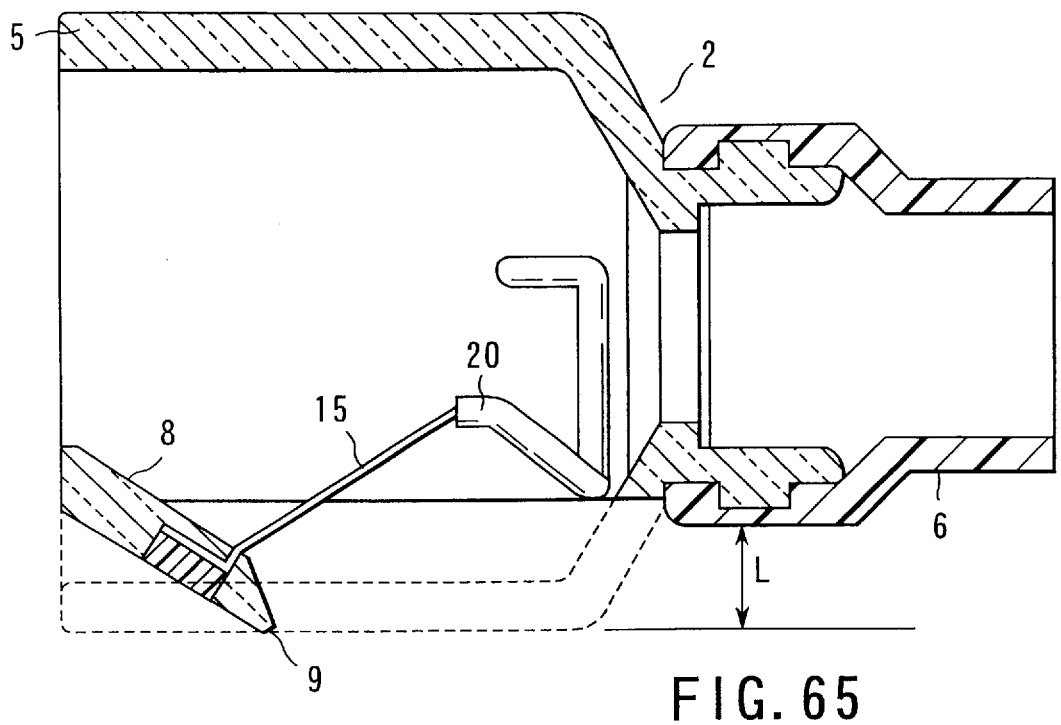
FIG. 65 is a longitudinal sectional view showing that the high-frequency treatment apparatus for the endoscope is inserted in the body cavity according to a sixteenth embodiment of the present invention.
Figure 66:
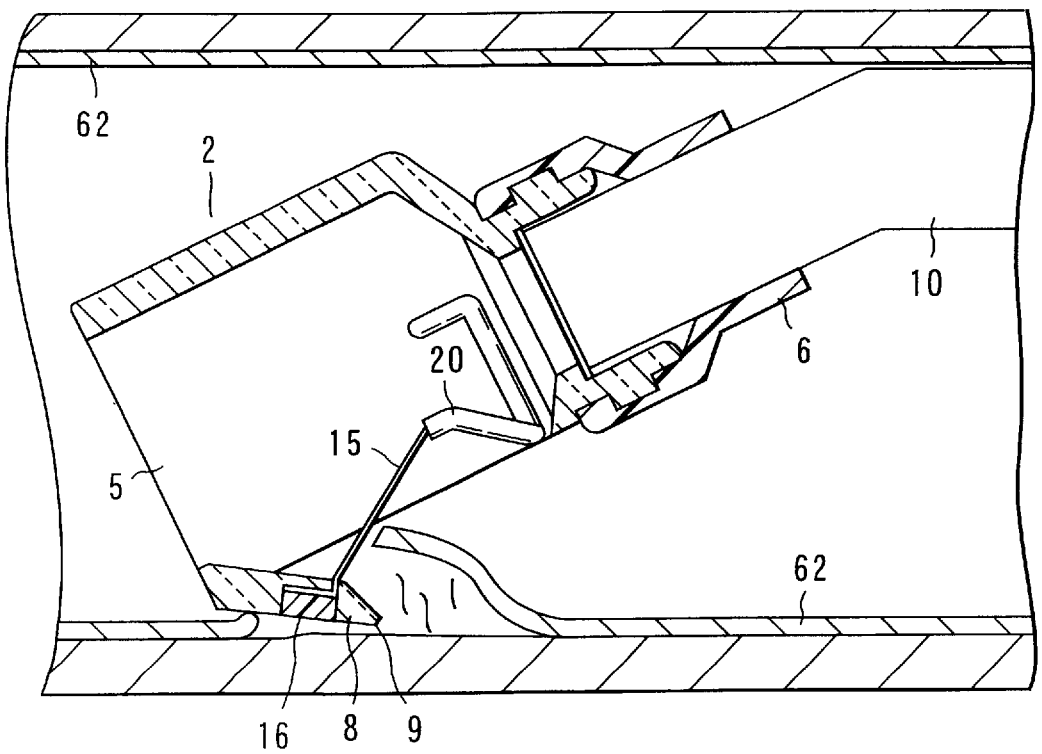
FIG. 66 is a longitudinal sectional view in the use state of the treatment apparatus shown in FIG. 65.
Figure 67:
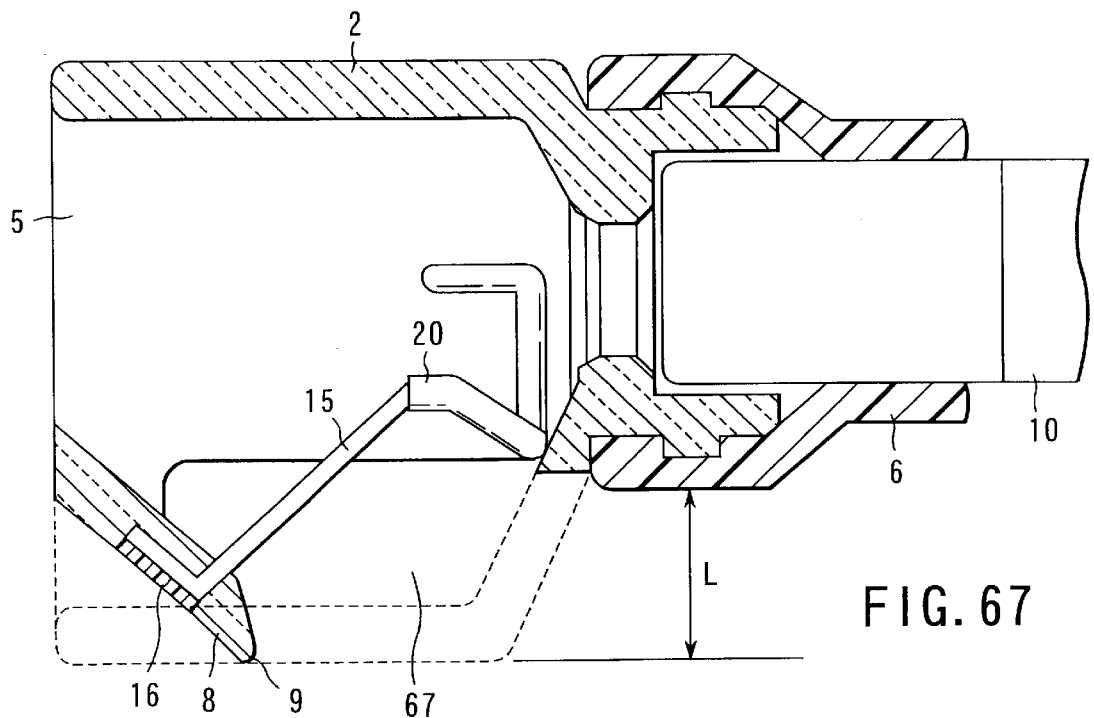
FIG. 67 is a longitudinal sectional view of a modification example of the treatment apparatus shown in FIG. 65.

FIGS. 65 to 67 show the treatment apparatus for the endoscope according to a sixteenth embodiment. The treatment apparatus is formed as the high-frequency incising apparatus for the endoscope similar to that of the thirteenth embodiment in broad terms.

Moreover, in the high-frequency incising apparatus for the endoscope in the sixteenth embodiment, the hood 2 is constituted as shown in FIG. 65. The portion shown by a broken line in FIG. 65 shows the shape of the cylindrical main body portion 5 of the hood 2 in the above-described thirteenth embodiment.

In the sixteenth embodiment, as shown in FIG. 65, since the portion shown by the broken line is omitted, the in-tissue inserting portion 8 projects from the outer surface of the hood 2 by a distance L. Moreover, the tip-end portion of the cylindrical main body portion 5 with the in-tissue inserting portion 8 formed therein is inclined/formed so that the tip end turns inwards. Thereby, the tip end 9 of the in-tissue inserting portion 8 is directed obliquely downwards.

The action of the sixteenth embodiment is the same as that of the thirteenth embodiment. Moreover, for the effect of the sixteenth embodiment, since the in-tissue inserting portion 8 projects obliquely downwards, the tip end 9 of the in-tissue inserting portion 8 is easily inserted under the mucosa. Furthermore, the tip-end portion of the cylindrical main body portion 5 is inclined inwards. Therefore, even when the inserting portion 11 of the endoscope 10 is curved in a mucosa direction as shown in FIG. 66, the in-tissue inserting portion 8 does not turn upwards. The tip end 9 of the in-tissue inserting portion 8 is therefore securely pushed and moved between the mucosa and muscle layer, and the in-tissue inserting portion 8 can easily incise the mucosa without being caught by the mucosa.

Moreover, since the portion shown by the broken line of FIG. 65 is omitted from the cylindrical main body portion 5, the in-tissue inserting portion 8 is projected. Therefore, as compared with the thirteenth embodiment, the outer shape is small, and the insertion property into the body cavity is superior.

Additionally, the portion inclined inwards is not limited to the portion shown in FIG. 65. That is, as long as the tip end of the projecting portion of the in-tissue inserting portion 8 is inclined inwards, the inclined portion may extend over the whole periphery or the half periphery of the tip end of the cylindrical main body portion 5. Moreover, as shown in FIG. 67, the cylindrical main body portion 5 may be formed to be eccentric with respect to the transverse section center of the endoscope 10. In this case, the projecting amount L can be enlarged without increasing the outer diameter of the cylindrical main body portion 5.

(Seventeenth Embodiment)

Figure 68:
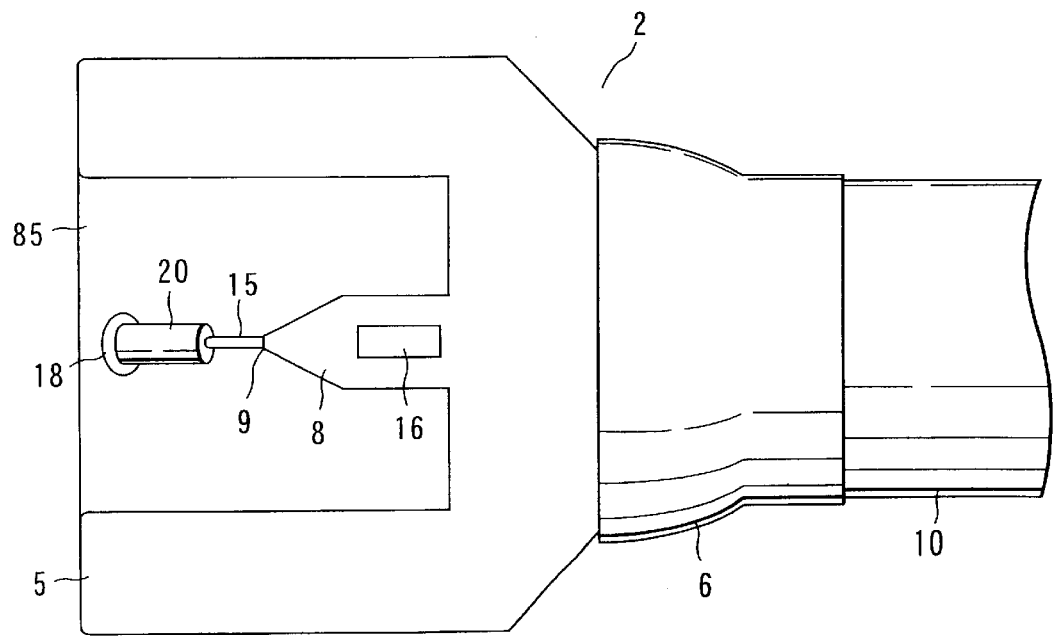
FIG. 68 is a lower surface view of the hood of the high-frequency treatment apparatus for the endoscope according to a seventeenth embodiment of the present invention.
Figure 69:
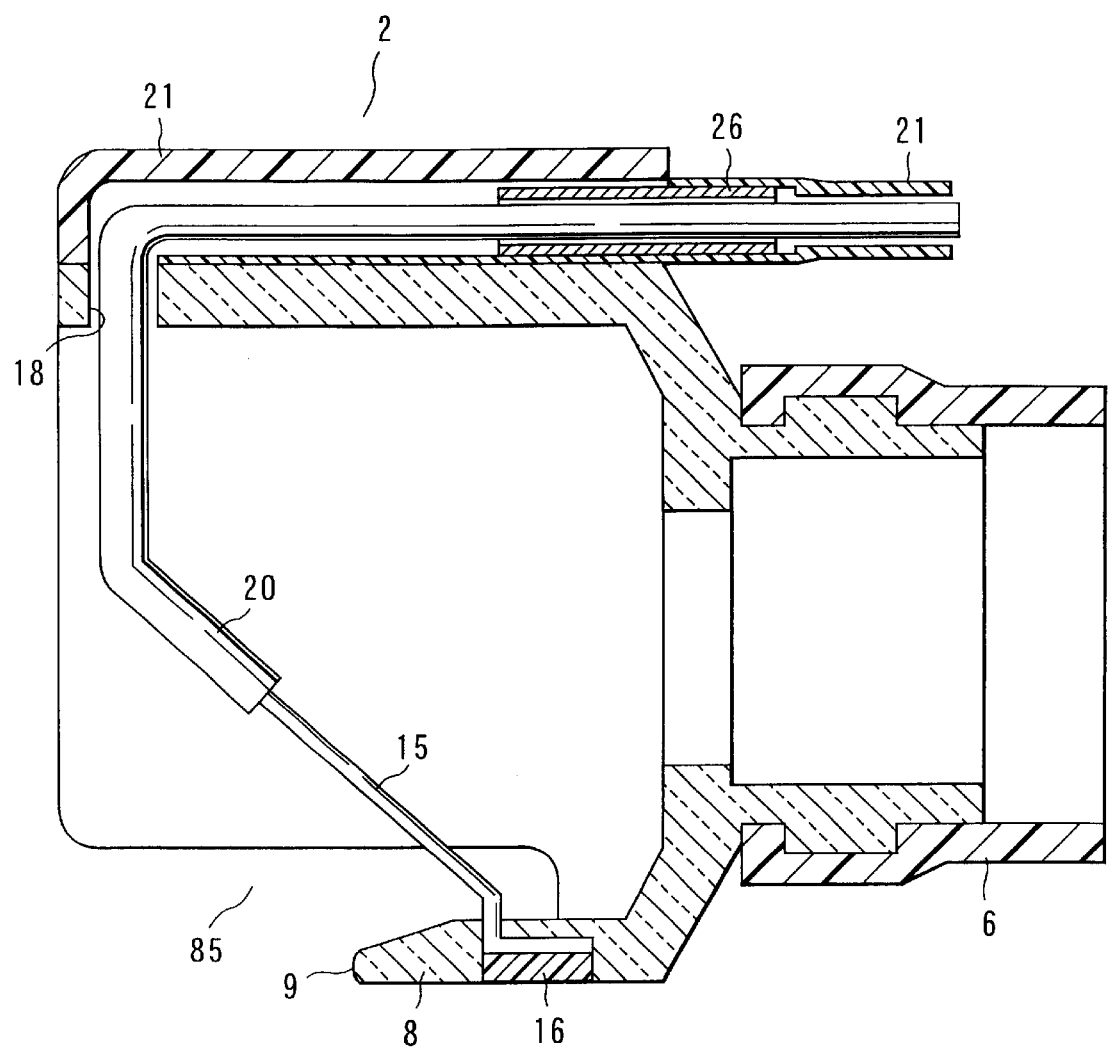
FIG. 69 is a longitudinal sectional view of the high-frequency treatment apparatus shown in FIG. 68.
Figure 70:
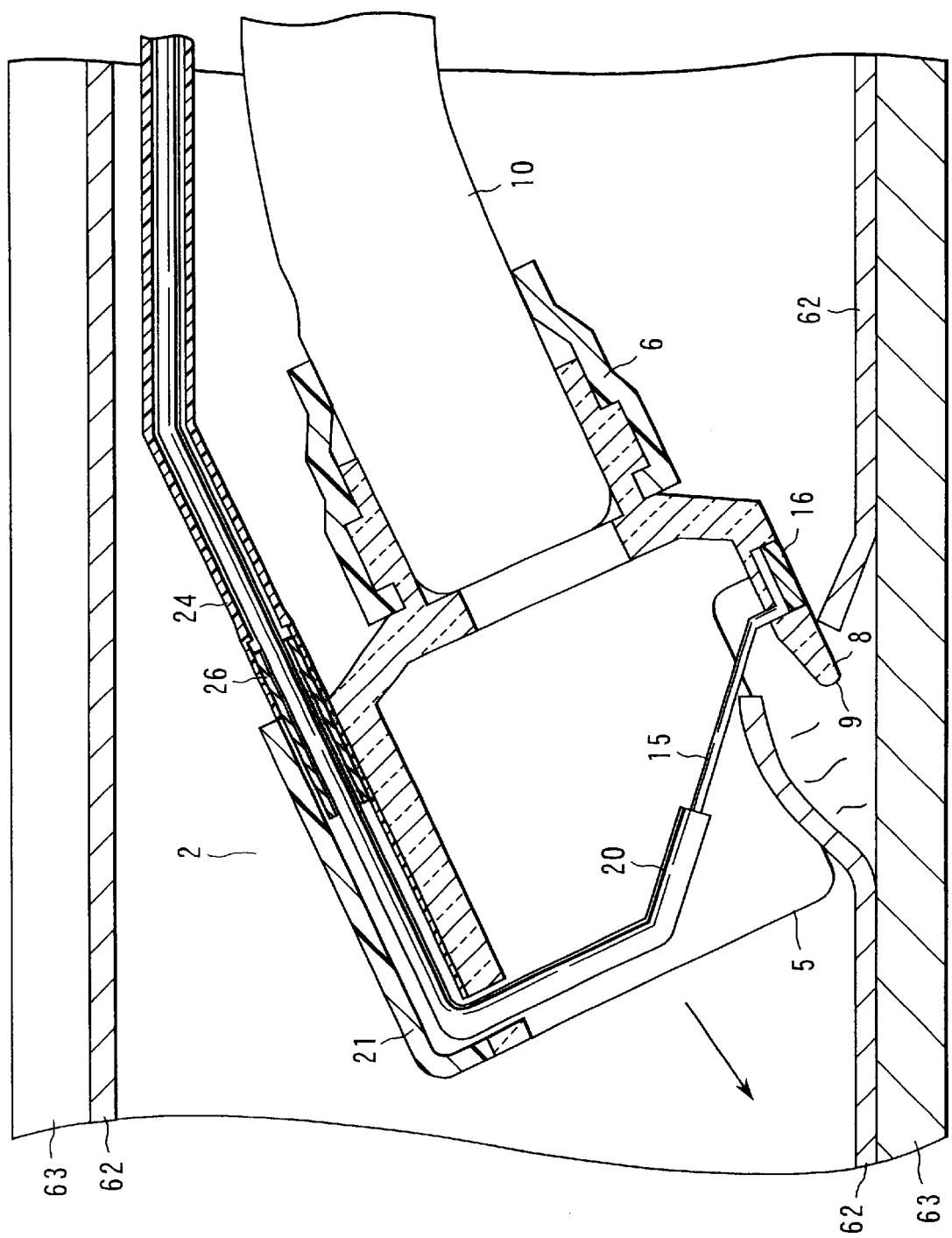
FIG. 70 is a longitudinal sectional view of the use state of the treatment apparatus shown in FIG. 68.

FIGS. 68 to 70 show the treatment apparatus for the endoscope according to a seventeenth embodiment. The treatment apparatus is formed as the high-frequency incising apparatus for the endoscope similar to that of the thirteenth embodiment in broad terms.

Moreover, the hood 2 of the high-frequency incising apparatus for the endoscope according to the seventeenth embodiment is constituted as shown in FIG. 68. In the seventeenth embodiment, the in-tissue inserting portion 8 projects toward the tip end of the hood 2. Furthermore, the in-tissue inserting portion 8 may be formed integrally with the cylindrical main body portion 5, or may be formed separately and bonded/fixed.

A cutout 85 opened forwards from opposite sides is disposed in the cylindrical main body portion 5, and the in-tissue inserting portion 8 is directed forwards in the cutout 85. Moreover, for the size of the cutout 85, the width is in the range of 1 mm to 15 mm, and the length is 1 mm to 15 mm. Especially preferably, the width is 3 mm to 9 mm, and the length is 4 mm to 8 mm. Furthermore, instead of the cutout 85, the side aperture may be disposed.

The side hole 18 for introducing the coated line 20 is positioned and formed relatively on the front end of the cylindrical main body portion 5. After the coated line is introduced into the cylindrical main body portion 5 in a diametric direction, the incision line 15 advances obliquely downwards, and is connected to the in-tissue inserting portion 8 projecting forwards.

The action of the high-frequency incising apparatus for the endoscope according to the seventeenth embodiment is the same as the thirteenth embodiment until the small incision 65 is formed. After the small incision, the inserting portion 11 of the endoscope 10 is moved forwards/backwards and the tip end 9 of the in-tissue inserting portion 8 is inserted under the mucosa 62 from the small incision 65.

Subsequently, when the inserting portion 11 of the endoscope 10 is pushed into the body cavity, the incision line 15 closely abuts on the mucosa 62. In this state, power is supplied, and the mucosa 62 is incised in the axial direction.

According to the high-frequency incising apparatus for the endoscope of the seventeenth embodiment, in the axial incision, the safe and easy method is possible. Moreover, as shown in FIG. 70, when the tip-end portion 12 of the inserting portion 11 is pressed onto the mucosa 62 to be incised by the curving operation of the endoscope 10, the front portion is opened by the cutout 85, and the in-tissue inserting portion 8 is directed obliquely downwards. The tip end 9 of the in-tissue inserting portion 8 securely comes under the mucosa 62 taken in the portion of the cutout 85, and is pushed and moved forwards between the mucosa 62 and muscle layer 63. The in-tissue inserting portion 8 is not caught by the mucosa 62.

Since the in-tissue inserting portion 8 is directed obliquely downwards as described above, the tip end 9 of the in-tissue inserting portion 8 is easily inserted under the mucosa 62.

(Eighteenth Embodiment)

Figure 71:
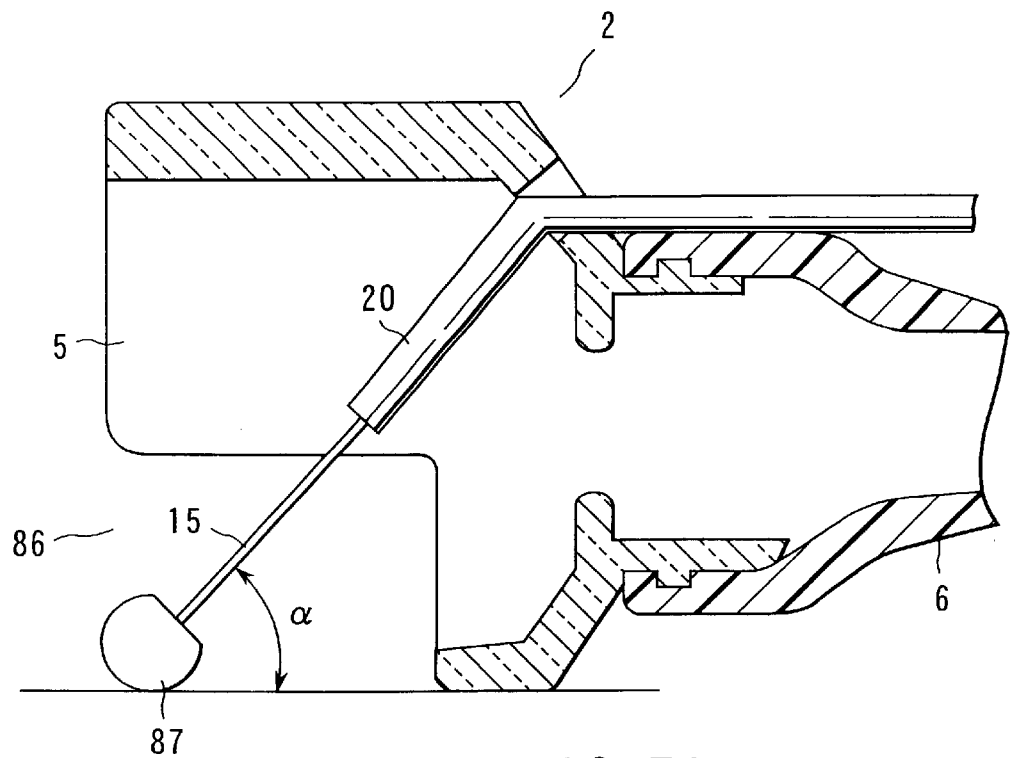
FIG. 71 is a longitudinal sectional view of the hood portion of the treatment apparatus for the endoscope according to an eighteenth embodiment of the present invention.

FIG. 71 shows the treatment apparatus for the endoscope according to an eighteenth embodiment. The treatment apparatus is formed as the high-frequency incising apparatus for the endoscope similar to that of the thirteenth embodiment in broad terms.

Moreover, as shown in FIG. 71, a cutout 86 extending to the tip end is disposed in the cylindrical main body portion 5 of the hood 2. For the size of the cutout 86, the width is in the range of 2 mm to 15 mm, and the length is 2 mm to 15 mm. Especially preferably, the width is 4 mm to 9 mm, and the length is 4 mm to 9 mm.

As shown in FIG. 71, the incision line 15 is obliquely disposed toward the lower cutout 86 from the rear upper portion of the hood 2. A tip-end insulation portion 87 having a substantially spherical shape is disposed on the tip end of the incision line 15, and has a diameter larger than the outer diameter of the incision line 15. The tip-end insulation portion 87 is formed of the material superior in electrical insulation and heat resistance, such as ceramic. Moreover, the tip-end insulation portion 87 has an outer diameter of 0.1 mm to 5 mm, especially preferably 0.5 mm to 2 mm. The shape of the tip-end insulation portion 87 is not limited to the shape shown in FIG. 71. The angle α of the incision line 15 to the mucosa 62 is in the range of 0° to 180°, especially preferably 15° to 75°.

The action of the high-frequency incising apparatus for the endoscope of the eighteenth embodiment is the same as that of the thirteenth embodiment until the small incision 65 is formed. After the small incision, by the forward/backward moving operation and angle operation of the inserting portion 11 of the endoscope 10, the tip-end insulation portion 87 disposed on the tip end of the incision line 15 is inserted into the small incision 65. Here, the tip-end insulation portion 87 functions as the in-tissue inserting portion.

During the incision of the circumferential direction, after the tip-end insulation portion 87 is inserted into the small incision 65, the inserting portion 11 of the endoscope 10 is rotated around the axis, and the mucosa 62 and incision line 15 are allowed to closely abut on each other. Thereafter, power is supplied to the incision line 15 and the mucosa 62 is incised.

For the incision of the circumferential direction, the affected area is incised at two places on mouth and alley sides. In this case, since the tip-end insulation portion 87 contacts the muscle layer 63, the current does not flow in the muscle layer 63.

Moreover, during the axial incision, after the tip-end insulation portion 87 is inserted in the small incision 65, the inserting portion 11 of the endoscope 10 is pulled so as to allow the mucosa 62 and incision line 15 to closely abut on each other. Thereafter, power is supplied to the incision line 15 and the mucosa 62 is incised. Additionally, for the axial incision, two left and right parts of the affected area are incised.

The treatment after the rectangular incision is added to the mucosa 62 as described above is the same as that of the thirteenth embodiment.

According to the high-frequency incising apparatus for the endoscope of the eighteenth embodiment, in the circumferential and axial incisions, the safe and easy method is possible with one device.

(Nineteenth Embodiment)

Figure 72:
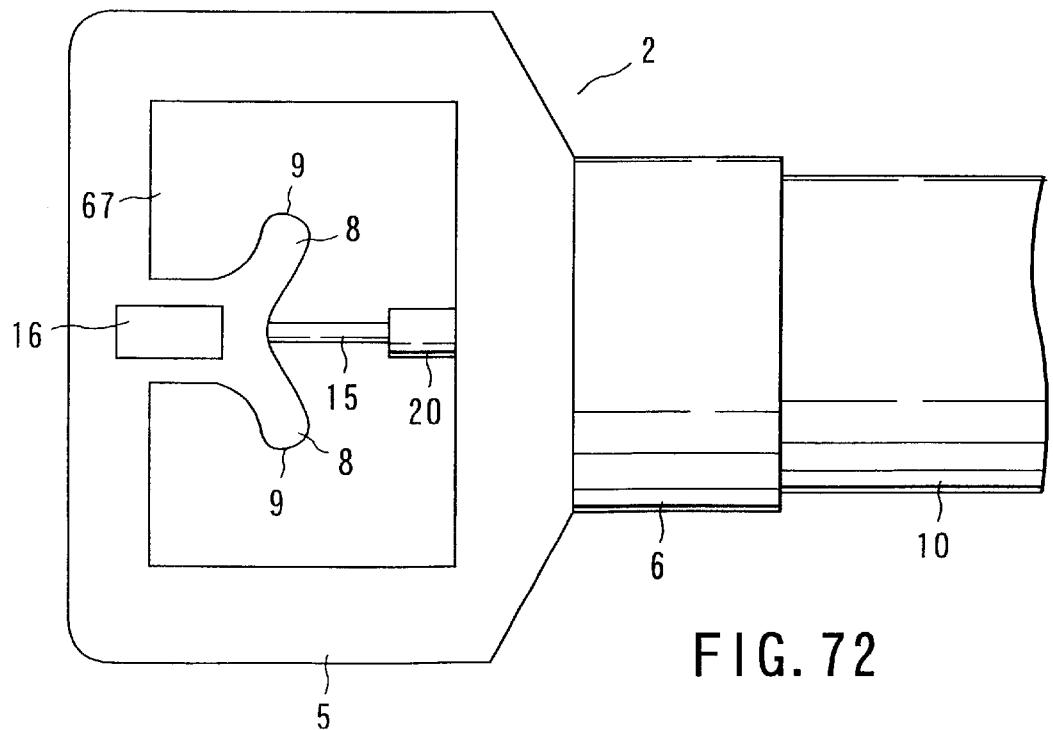
FIG. 72 is a lower surface view of the hood portion of the treatment apparatus for the endoscope according to a nineteenth embodiment of the present invention.

FIG. 72 shows the treatment apparatus for the endoscope according to a nineteenth embodiment. The treatment apparatus is formed as the high-frequency incising apparatus for the endoscope similar to that of the thirteenth embodiment in broad terms.

Moreover, in the high-frequency incising apparatus for the endoscope in the nineteenth embodiment, the hood 2 is constituted as shown in FIG. 72. That is, in the nineteenth embodiment, the in-tissue inserting portion 8 is branched into two so that the portion is symmetrically divided outwards on the tip-end side. Moreover, the respective portions of the in-tissue inserting portion 8 may be integral or may be separate and bonded/fixed. Furthermore, the in-tissue inserting portion 8 may not be symmetrically divided. Additionally, two portions of the in-tissue inserting portion 8 may not have the same size.

A using method is the same as that of the fourteenth embodiment. However, since the mucosa 62 is pushed from side to side and incised by the outwardly two-forked in-tissue inserting portion 8, the mucosa 62 of the part contacting the incision line 15 is pulled from side to side and becomes thin. The mucosa 62 is easily incised.

(Twentieth Embodiment)

FIGS. 73 to 76 show the treatment apparatus for the endoscope according to a twentieth embodiment.

Figure 73:
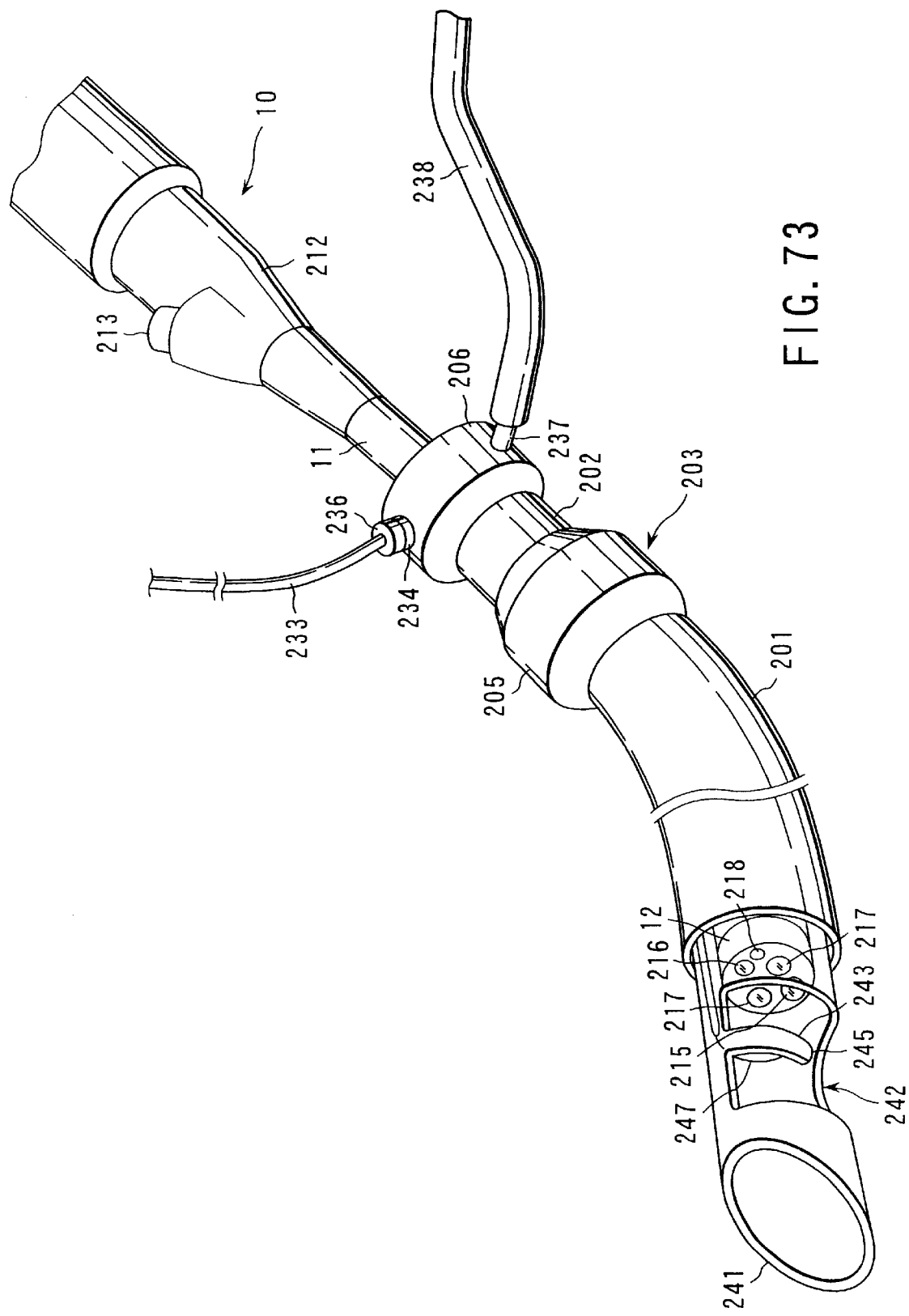
FIG. 73 is a perspective view schematically showing the treatment apparatus for the endoscope according to a twentieth embodiment.

FIG. 73 is a perspective view of a use state, schematically showing the treatment apparatus for the endoscope according to the twentieth embodiment. The treatment apparatus for the endoscope includes a guide tube 203 including an outer cylinder (sheath) 201 and inner cylinder 202. The inner cylinder 202 is inserted in the outer cylinder 201 so that the inner cylinder can slid, move forwards/backwards, and rotate. The flexible inserting portion 11 of the endoscope 10 is inserted into the inner cylinder 202. When the inserting portion 11 of the endoscope 10 is inserted in the guide tube 203, the inner cylinder 202 and inserting portion 11 can slide, move forwards/backwards, and rotate.

An inlet 213 of the treatment instrument insertion passage (channel) is formed in an operating portion 212 of the endoscope 10. An outlet 215 of the treatment instrument insertion passage is formed in the tip-end surface of the tip-end portion 12 in the inserting portion 11. Additionally, an observation window 216, lighting windows 217, and nozzle 218 are disposed in the tip-end surface of the tip-end portion 12. Here, the endoscope 10 constitutes a direct side type endoscope, but may be a squint embodiment as long as forward observation is possible.

A large-diameter cap 205 also serving as a grip portion is disposed on the base end of the outer cylinder 201 in the guide tube 203. Moreover, a large-diameter cap 206 also serving as the grip portion is also disposed on the base end of the inner cylinder 202. The caps 205 and 206 include air-tight seals constituted to secure air tightness with fit components and not to block the rotation/forward and backward movement of the components.

FIG. 74 shows the structure of the caps 205 and 205 with the air-tight seals incorporated therein. These constitutions will be described. A rear-end portion of a tube material 221 forming the outer cylinder 201 is fit with a tapered portion 223 disposed in the tip end of a main body 222 in the cap 205. The portion is pressed by a fastening screw ring 224, brought into the airtight state, and connected to the cap 205. Moreover, a flange 225 is formed in the rear-end portion of the main body 222 in the cap 205, and an annular rubber seal 226 is attached to the flange 225 in an airtight manner. The diameter of the middle hole in the rubber seal 226 is slightly smaller than the outer diameter of the inner cylinder 202 inserted in the hole. Therefore, the rubber seal 226 holds a gap with the inner cylinder 202 to be airtight.

Similarly, the rear-end portion of a tube material 227 forming the inner cylinder 202 is fit with a tapered portion 229 disposed in the tip end of a main body 228 in the cap 206. The portion is pressed by a fastening screw ring 230, brought into the airtight state, and connected to the cap 206. Moreover, two annular rubber sheet seals 231 are fastened/fixed by a stop screw ring 232 in the rear end of the main body 228 in the cap 206. The inner diameter of each sheet seal 231 is formed to be slightly smaller than the outer diameter of the inserting portion 11 of the endoscope 10. Therefore, each sheet seal 231 holds a gap with the inserting portion 11 of the endoscope 10 to be airtight.

Two holes are formed in the main body 228 in the cap 206 for the inner cylinder 202 and positioned before the sheet seals 231. A high-frequency cable 233 is inserted into one hole, and a flanged cap 234 for the cable is attached to the hole. A rubber plug 236 having a slit in the middle thereof is attached to a flange 235 of the cap 234 to be attachable/detachable and airtight.

To the other hole, a tapered flanged cap 237 for the tube with a thin tip end is attached. A tube 238 for backflow is connected via the cap 237, and the rear end of the tube 238 is connected to a backflow apparatus (not shown).

Examples of the outer cylinder 201 of the guide tube 203 include porous polytetrafluoroethylene superior in flexibility and slippage. The outer cylinder 201 is shorter than the inner cylinder 202 of the guide tube 203, and the inner diameter of the outer cylinder 201 is slightly larger than the outer diameter of the inner cylinder 202. Moreover, the outer diameter of the outer cylinder 201 is usually 18 mm or less, so that the cylinder can orally be inserted in esophagus by toponarcosis. The outer cylinder 201 has a thickness of about 1 mm. The material of the inner cylinder 202 of the guide tube 203 is a fluorine-based elastomer resin, and the inner cylinder 202 is transparent, flexible, and superior in heat resistance and electrical insulation.

As shown in FIG. 73, the tip end of the inner cylinder 202 of the guide tube 203 is obliquely cut, and the tip edge is formed as a sharp edge 241.

Moreover, a side aperture 242 substantially U-shaped as seen from the side is opened to extend over substantially a half circumference in one side portion behind the tip end of the inner cylinder 202. A incising instrument holding portion 243 projects toward the middle of the side aperture 242 from one edge (side) positioned in the circumferential direction in the side aperture 242 integrally with the circumferential portion of the inner cylinder 202 and at the same curvature as that of the inner cylinder. That is, the incising instrument holding portion 243 has a strip shape which projects in a transverse direction (circumferential direction) from one side wall of the side aperture 242. The tip end of the incising instrument holding portion 243 forms a tapered incising instrument introducing portion 245. Here, the incising instrument introducing portion 245 is gradually thinned toward the tip-end portion thereof, and the tip edge thereof is formed to be round. A portion of the incising instrument holding portion 243 including the incising instrument introducing portion 245 serves as the in-tissue inserting portion during the treatment of the tissue in the body cavity as described above. The tip end of the incising instrument holding portion 243 or the inner cylinder 202 serves as a base for supporting the in-tissue inserting portion. This also applies to other embodiments and modification examples described hereinafter.

The incising instrument introducing portion 245 is formed substantially by 2 mm from the tip end of the incising instrument holding portion 243 along the circumference of the inner cylinder 202. A conductive wire 247 which generates heat by a high-frequency electrode, that is, high-frequency current extends to the base of the incising instrument holding portion 243 from behind the incising instrument introducing portion 245, and is straight extended in a position through which the inserting portion 11 of the endoscope 10 is inserted. The incising instrument holding portion 243 is formed like a bow whereas the wire 247 is formed as a string. Moreover, in the twentieth embodiment, the wire 247 serving as the high-frequency electrode is disposed on the incising instrument holding portion 243 with the incising instrument introducing portion 245 formed on the tip end thereof. When the high-frequency current is supplied, the wire 247 acts as the incising portion, and constitutes the high-frequency incising instrument which can incise the tissue.

The rear end of the wire 247 is connected to the high-frequency cable 233 for supplying the high-frequency current. The high-frequency cable 233 is coated with an electrically insulating resin. Moreover, the high-frequency cable 233 is passed in the inner cylinder 202 in the axial direction from the incising instrument holding portion 243, goes outwards from the cap 234 for the cable of the rear-end cap 206, is guided to the high-frequency power supply (not shown), and connected to the high-frequency power supply apparatus.

Figure 75:
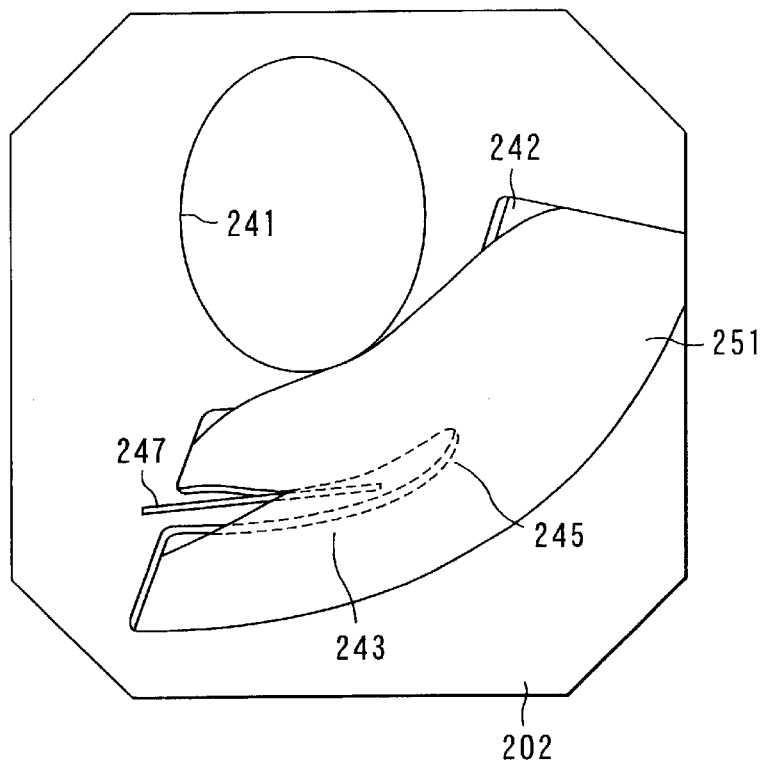
FIG. 75 is an explanatory view of a treatment state by the treatment apparatus of FIG. 73 indicated by the endoscope image.

A method of using the treatment apparatus for the endoscope according to the twentieth embodiment will next be described with reference to FIGS. 75 and 76.

The inserting portion 11 of the endoscope 10 is inserted into the body cavity such as esophagus. Thereafter, the inserting portion 11 is used as a guide to insert the guide tube 203 with which the inserting portion 11 is covered into the body cavity, or to insert the guide tube 203 and inserting portion 11 covered with the guide tube 203 together into the body cavity. In any case, the inner cylinder 202 of the guide tube 203 is drawn inside the outer cylinder 201.

Subsequently, the long syringe needle introduced through the treatment instrument insertion passage of the endoscope 10 is stuck in a mucosa 251 of the affected area such as barrett esophagus to be resected. The physiological saline mixed with a hemostatic agent and dyeing agent is injected over the whole periphery in the mucosa lower layer between the mucosa 251 and muscle layer 252. Then, a boundary tissue 253 of the mucosa 251 and muscle layer 252 absorbs the injected solution and is swollen in a jelly form, and the mucosa 251 is sufficiently detached from the muscle layer 252.

Therefore, a hole is made in a part of the mucosa 251 with an electric scalpel inserted in the treatment instrument insertion passage of the endoscope 10. Furthermore, by the sucking operation of the endoscope 10, the mucosa 251 is sucked into the side aperture 242, inner cylinder 202 is moved forwards/backwards and rotated, and the introducing portion 245 of the incising instrument holding portion 243 is aligned with the hole made in the mucosa 251. The inner cylinder 202 is rotated in a counterclockwise direction, and the incising instrument introducing portion 245 is allowed to enter the boundary tissue 253 of the mucosa 251 and muscle layer 252.

When the incising instrument introducing portion 245 comes under the mucosa 251 in this manner, the inner cylinder 202 is further rotated. When the wire 247 comes under the mucosa 251 by a half length, the sucking is stopped. Air is supplied, and the wire 247 is brought in close contact with the backside of the mucosa 251.

Subsequently, a foot switch of the high-frequency power supply is stepped on and power is supplied. The mucosa 251 is cut by the heat generated in the wire 247 (see FIG. 75). During the power supply, steam and smoke are generated. Therefore, the air supply and sucking operation by the endoscope 10 is repeated, and steam and smoke are removed. Alternatively, the backflow apparatus coupled with the high-frequency power supply apparatus is started, the air supply and suction are repeated between the inserting portion 11 of the endoscope 10 and the inner cylinder 202 through the tube 238, smoke is removed, and the view field of the endoscope is secured.

A series of operations are repeated, and the whole periphery of the mucosa 251 is incised in the annular shape.

Subsequently, similarly, another part in a position apart in a back to forth direction is incised in the annular shape. To align cutting start and end positions in each incised part, the incised and exposed muscle layer part is observed over the transparent inner cylinder 202, and positioned by the forward/backward moving operation of the inner cylinder 202.

Figure 76:
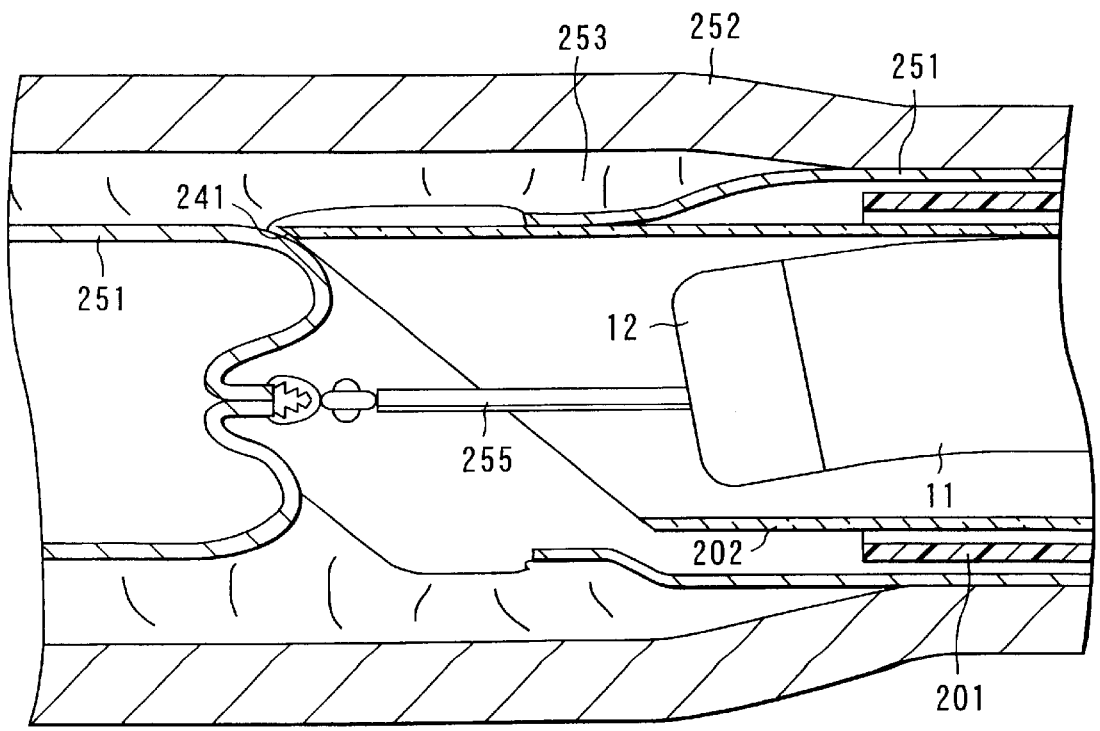
FIG. 76 is an explanatory view of the treatment state of the treatment apparatus shown in FIG. 73.

Subsequently, as shown in FIG. 76, the incised end of the whole periphery is sucked into the tip end of the inner cylinder 202 and reduced. Thereafter, the incised end is closed with high-frequency grip forceps 255 to which a high-frequency current can be supplied, and pushed forwards.

Continuously, the sharp edge 241 of the inner cylinder 202 is slowly inserted between the mucosa 251 and boundary tissue 253, and the inner cylinder 202 is slowly rotated and advanced. Thereby, the boundary tissue 253 is cut, and the mucosa 251 is stripped from the muscle layer 252. In case of bleeding halfway, the tip end of the high-frequency grip forceps 255 is allowed to abut on the bleeding part, a coagulation current is supplied, and the bleeding is stopped.

Moreover, when a fiber tissue cannot be completely cut by the edge 241 of the inner cylinder 202, and remains, the tissue is grasped and torn by the high-frequency grip forceps 255. In this case, since the cut end grasped by the high-frequency grip forceps 255 is released, the cut end is again sucked, grasped by the high-frequency grip forceps 255, and pushed forwards.

These operations are repeated, and the cylinder of the mucosa 251 including the affected area is progressively stripped as if turned over. When the other annular incised portion is reached, the whole periphery of the mucosa is naturally turned over in a cylinder shape and resected.

Additionally, the outer cylinder 201 of the guide tube 203 is formed, for example, of tetrafluoroethylene and is superior in slippage, and the inner cylinder 202 is easily moved forwards/backwards and rotated. Moreover, the inner cylinder 202, for example, of a fluorine-based elastomer resin is superior in heat resistance and is not melted or deformed by high-frequency heat.

Since the inner cylinder 202 is transparent, the incised part is reflected in the endoscope image over the inner cylinder, and the treatment for aligning the cut start and end of the annular incision can easily be performed. The incising instrument holding portion 243 is an insulator integral with the inner cylinder 202, the high-frequency wire 247 is not positioned in the incising instrument introducing portion 245, and the backside of the mucosa 251 is not burnt. The incising instrument introducing portion 245 does not include any wire 247, has a tapered, thin and round shape, is easily inserted under the mucosa and guide the wire 247 under the mucosa. Even after the incision, the portion is not detached and remains under the mucosa. Therefore, the incising instrument introducing portion is useful for continuous incision.

Since the wire 247 is disposed inside and apart from the incising instrument holding portion 243 contacting the muscle layer 252, heat generated by the power supply is not easily conducted, and the muscle layer 252 is not heated.

Moreover, various airtight seals disposed on the rear end of the guide tube 203 prevent air supplied into the body cavity from leaking, and outside air is not sucked during the sucking operation. Additionally, for example, jelly is applied to the rubber seal portion for lubrication, air tightness is thereby kept, and it is possible to rotate/move forwards/backwards the inserting portion 11 of the endoscope 10 and the inner cylinder 202.

During the incision in the annular shape, when the incising instrument is brought under the mucosa, the mucosa 251 ridden onto the wire 247 is reflected in the endoscope image. Thereby, it can be confirmed that the wire 247 is not disposed on the muscle layer side, and the operator can continuously cutting the mucosa at ease.

After the incision, the incising instrument introducing portion 245 in the tip end of the incising instrument holding portion 243 remains under the mucosa, the incising instrument is not disengaged, and the continuous incision is facilitated.

Moreover, during the stripping, two annular incisions are added, and the corresponding parts are stripped at one stroke by the sharp edge 241 of the inner cylinder 202, so that the operator can strip the mucosa in a short time and does not get tire.

In this case, since the sharp edge 241 is formed of a relatively flexible material, only the relatively soft boundary tissue having absorbed the physiological saline, and become jellied is incised.

Additionally, since the mucosa 251 is turned over, the part to be stripped can securely be observed as the endoscope image around the tip end of the hood shape, and the part can continuously be stripped at ease.

Moreover, the high-energy apparatus is not used in the stripping, and the conventional problems do not occur that smoke or steam is generated, the view field cannot be secured, and that the stripping operation is discontinued.

Furthermore, even with the bleeding from the part to be stripped, the part to be stripped can quickly be defined, and the bleeding can quickly be stopped using a coagulation bleeding stop treatment instrument through the treatment instrument insertion port.

The portion of the sharp edge 241 is introduced into the body cavity via the outer cylinder 201, the mucosa is not damaged by the acute-angled edge during the inserting.

MODIFICATION EXAMPLE

Since the organ as an object to which the present invention is applied is not limited to esophagus, the inner/outer diameter and length of the guide tube 203 are not limited to numeric values of the twentieth embodiment. Moreover, the inner cylinder 202 of the guide tube 203 may be formed of two members, the tip end thereof may be formed of the material superior in heat resistance and electrical insulation, and the rear portion thereof may be formed of another flexible material. The size and shape of the side aperture 242 are not limited to those of the twentieth embodiment. The curvature of the incising instrument holding portion 243 is the same as that of the inner cylinder 202 in the twentieth embodiment, but the curvature may be small in a range in which the inserting portion 11 of the endoscope 10 is inserted without any trouble. The lengths of the incising instrument holding portion 243 and incising instrument introducing portion 245 are not limited to those of the twentieth embodiment. The shape of the wire 247 may be changed to a circular arc shape in a range in which the inserting portion 11 of the endoscope 10 is inserted without any trouble.

Moreover, the shape of the sharp edge 241 formed on the inner cylinder 202 of the guide tube 203 for stripping the tissue is not limited to that of the first embodiment. Then, various examples of the sharp edge 241 are shown in FIGS. 77A to 77E.

In the example shown in FIG. 77A, the tip end of the inner cylinder 202 is cut at right angles, and the tip edge thereof is sharply cut in the whole circumference to form the sharp edge 241. According to the sharp edge 241, when the whole periphery of the mucosa is collectively resected, the mucosa can be stripped at once over the whole periphery.

In the example shown in FIG. 77B, the lower half circumference of the tip end of the inner cylinder 202 is obliquely cut, and the upper half circumference is cut at right angles. Moreover, the sharp edge 241 is formed in the lower half circumference. In this example, since the sharp edge 241 is formed in the lower half circumference, the tissue is easily stripped. Furthermore, since the upper half circumference is formed at right angles, the lower half circumferential portion is not easily deformed.

In the example shown in FIG. 77C, the tip end of the inner cylinder 202 is cut in the circular arc shape, and the sharp edge 241 is formed in the circular shape. Since the sharp edge 241 is formed more sharply than before, the tissue is easily stripped, sharpness is satisfactory, and therefore even the fiber tissue can easily be cut.

In the example shown in FIG. 77D, the tip end of the inner cylinder 202 is formed in a closed hood shape, and the rear edge of the side aperture 242 is formed as the sharp edge 241. Accordingly, since the tip end of the inner cylinder 202 is closed, the mucosa 251 can be sucked only into the side aperture 242. Therefore, when the periphery of the affected area is incised beforehand, the tissue can be stripped even from organs other than the lumen organ, such as stomach.

In the example shown in FIG. 77E, the tip edge of the inner cylinder 202 has right angles, and the saw-tooth shaped sharp edge 241 is directed in a longitudinal direction and formed in the right-angled tip edge. For the effect, even the remaining fiber tissue which is not completely incised by the rotating and stripping operation can be cut.

(Twenty-First Embodiment)

Figure 78:
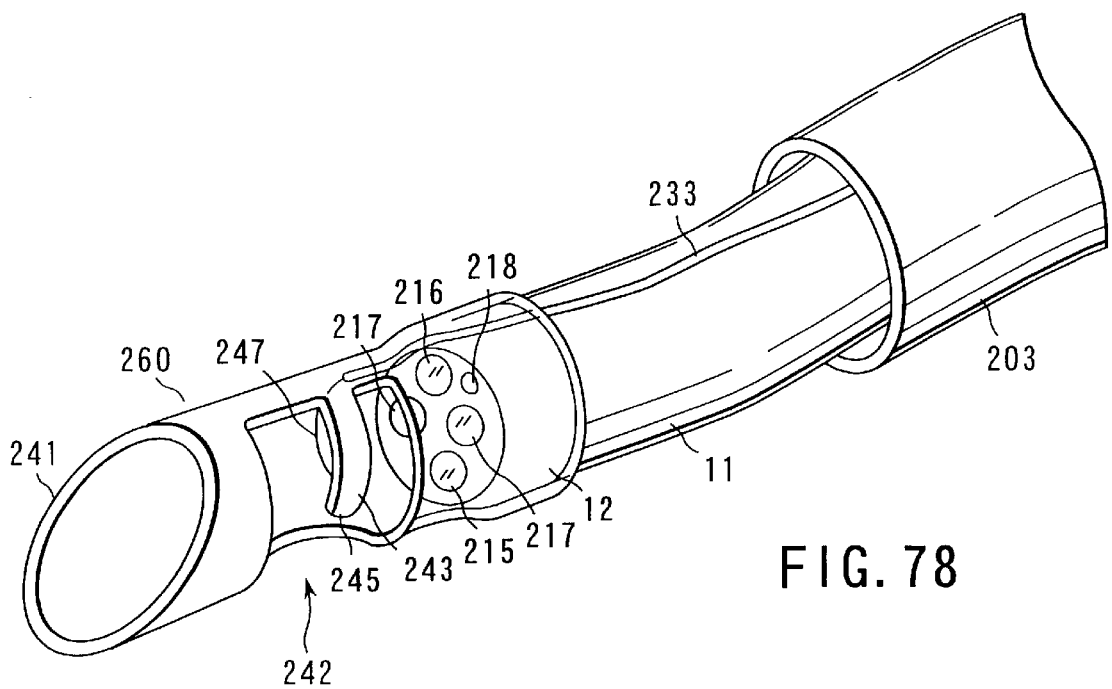
FIG. 78 is a perspective view of the vicinity of the tip end of the treatment apparatus for the endoscope according to a twenty-first embodiment.

FIG. 78 shows the treatment apparatus for the endoscope according to a twenty-first embodiment.

In the twenty-first embodiment, the inner cylinder 202 of the twentieth embodiment is omitted, and instead, a cylindrical hood 260 having an attachable/detachable inner diameter and formed of a flexible and transparent resin superior in heat resistance is disposed as a tubular member in the tip-end portion 12 of the endoscope 10. The hood 260 includes the sharp edge 241, side aperture 242, incising instrument holding portion 243 and wire 247 similarly as the twentieth embodiment.

Here, the guide tube 203 does not have an inner/outer double cylinder structure, and has a single structure. The middle hole diameter of the rubber seal of the cap disposed on the rear end is slightly smaller than the outer diameter of the inserting portion 11 of the endoscope 10. Moreover, the high-frequency cable 233 is taped and fixed at several positions on the inserting portion 11 of the endoscope and passed inside the guide tube 203.

Moreover, the inserting portion 11 of the endoscope 10 can be moved forwards/backwards and rotated with respect to the guide tube 203.

The use method of the twenty-first embodiment is the same as the twentieth embodiment, but the hood 260 acts instead of and similarly as the inner cylinder 202 of the twentieth embodiment. Moreover, since the hood 260 is moved forwards/backwards and rotated, an external force is added. However, the hood 260 is tightly attached to the tip-end portion 12 of the endoscope 10 and does not fall. Since the high-frequency cable 233 of the wire 247 is electrically insulated, the current does not flow to the patient. When the high-frequency cable 233 is taped/fixed onto the inserting portion 11 of the endoscope 10, the cable is not wound around even by the rotating operation including the incising.

Since the hood 260 is used in the twenty-first embodiment, it is unnecessary to insert the inserting portion 11 of the endoscope 10 through the hood as in the using of the inner cylinder 202. Therefore, it is possible to extend the wire 247 in a largely projecting circular arc shape long inside the hood 260, one length to be incised can be increased, and therefore a time for incising the tissue in the annular shape can be shortened.

Moreover, the portion corresponding to the inner cylinder 202 is omitted. Therefore, when the endoscope 10 having the inserting portion 11 with the same outer diameter as that of the twentieth embodiment is used, the outer diameter of the guide tube 203 can be smaller than that of the first embodiment, and therefore the patient can be relieved from pain.

Furthermore, when the guide tube 203 having the same thickness as that of the outer cylinder 201 of the twentieth embodiment is used, and the endoscope 10 having the thick inserting portion 11 and thick treatment instrument insertion passage is combined, the forceps having a large tip end can be used, and the fiber tissue is easily cut.

Additionally, smoke generated during the high-frequency incision is easily sucked. Moreover, it is also possible to use the endoscope which includes two forceps insertion passages, and includes a forceps elevator mechanism in one outlet (see the endoscope shown in FIG. 80). In this combination, the forceps elevator mechanism facilitates the positioning operation of the forceps tip end. Additionally, since two pairs of forceps can simultaneously be used, the operations such as the cutting of the fiber tissue, the stopping of the bleeding stop, and the positioning of the mucosa are facilitated.

During the repeating of the incising, soot-like dirt adheres to the wire 247, and the wire does not cut, and needs to be replaced. However, since the hood 260 is inexpensive as compared with the guide tube 203, economical burden of the replacement is reduced.

(Twenty-Second Embodiment)

Figure 79A:
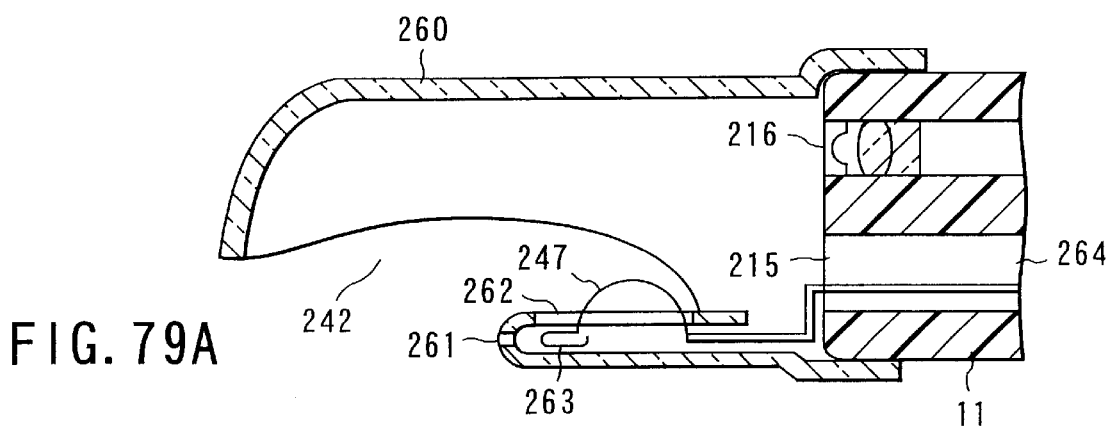
FIGS. 79A and 79B are a longitudinal sectional view and perspective view of the vicinity of the tip end of the treatment apparatus for the endoscope according to a twenty-second embodiment, respectively.
Figure 79B:
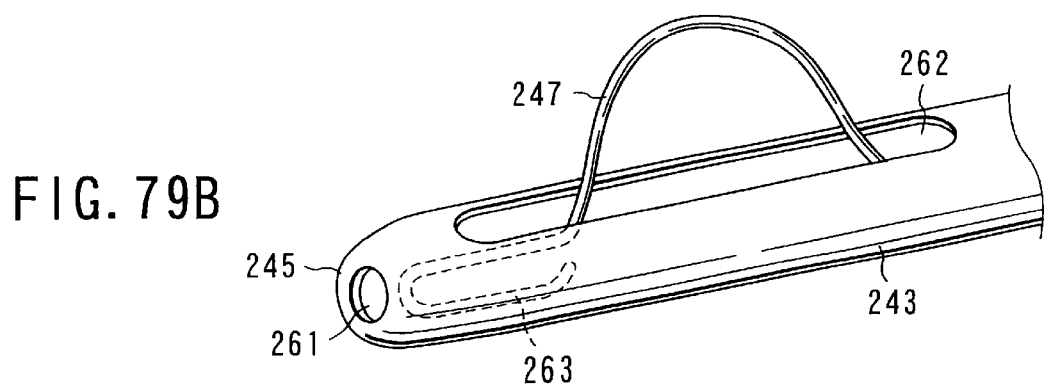
Figure 80:
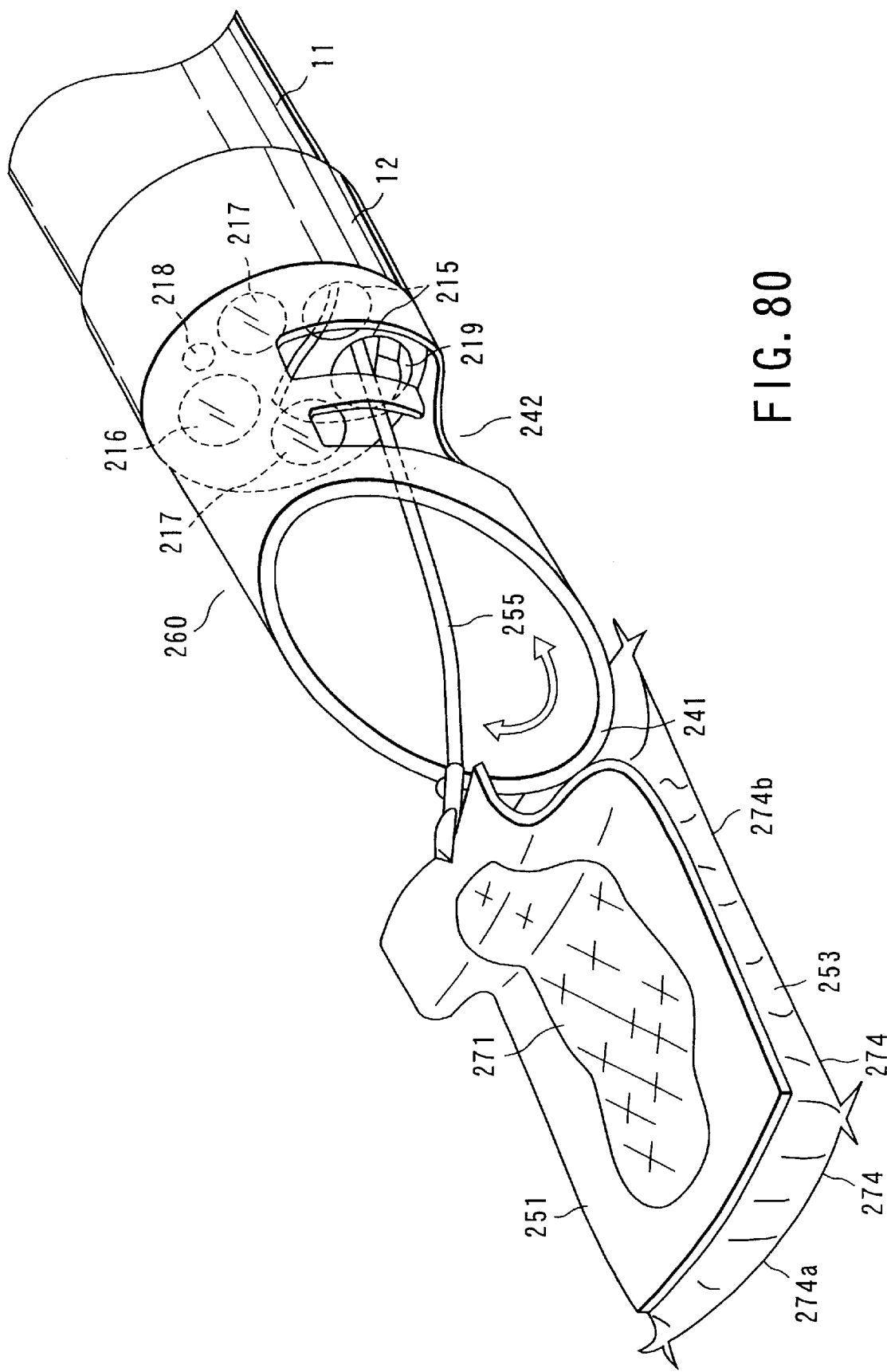
FIG. 80 is an explanatory view of the use state of the treatment apparatus for the endoscope according to the twenty-second embodiment.

FIGS. 79A, 79B and 80 show the treatment apparatus for the endoscope according to a twenty-second embodiment.

In the twenty-second embodiment, similarly as the twenty-first embodiment, the hood 260 is used, but the side aperture 242 is formed in the hood 260 to extend in a broad range to the oblique front lower half of the hood 260. Moreover, the incising instrument holding portion 243 is disposed to project to the vicinity of the middle portion from the rear end of the side aperture 242 along the axial direction of the hood 260.

Here, the incising instrument holding portion 243 is formed in the shape of a hollow pipe, and the incising instrument introducing portion 245 formed by the tip-end portion of the incising instrument holding portion 243 is formed in a bullet shape.

Moreover, a hole 261 is made in the middle of the incising instrument introducing portion 245 of the incising instrument holding portion 243, and an elongate circular slit 262 is opened along the axial center direction in the upper side surface portion of the incising instrument holding portion 243 which is directed inwards.

The wire 247 projects to the inside of the hood 260 in a semicircular shape from the slit 262 of the incising instrument holding portion 243. The tip-end portion of the wire 247 is bent like a hairpin inside the incising instrument holding portion 243. A hairpin portion 263 is slidably contained in the incising instrument holding portion 243. The maximum diameter of the semicircular portion of the wire 247 projecting from the slit 262 is smaller than the length of the slit 262. When the semicircular portion is positioned forwards, the tip-end hairpin portion 263 projects from the hole 261 by the same length as the thickness of the mucosa 251, and functions as a high-frequency knife for incising only the mucosa 251 of the tissue sucked and taken into the hood 260 from the side aperture 242.

On the other hand, the rear end of the wire 247 is connected to the high-frequency cable 233, and the connection tip-end portion of the high-frequency cable 233 is bent in a crank or S shape and guided into a treatment instrument insertion passage 264 of the endoscope 10. The high-frequency cable 233 is coated with a thick and hard resin PFA, and has rigidity to such an extent that an operating force by a pushing/pulling operation in the vicinity of the treatment instrument insertion passage inlet of the endoscope 10 is transmitted to the wire 247. That is, the high-frequency cable 233 also serves an operating wire for moving the wire 247 forwards/backwards.

Moreover, when the high-frequency cable 233 is moved forwards/backwards, the semicircular portion of the wire 247 projecting from the slit 262 of the incising instrument holding portion 243 moves forwards/backwards along the slit 262. Furthermore, the moving range of the wire 247 is regulated by a range length of the forward/backward direction of the slit 262. Additionally, the wire 247 function as the high-frequency knife for moving and incising the mucosa 251 of the tissue taken into the hood 260 from the side aperture 242.

An object in using the hood 260 of the twenty-second embodiment is to incise the mucosa 251 along the axial direction of the inserting portion 11 in the endoscope 10. After the physiological saline is locally injected under the mucosa of an affected area 271 to be resected and the mucosa is swollen in the bump shape, the mucosa 251 is sucked into the side aperture 242. Then, the operator picks the high-frequency cable 233 in the vicinity of the inlet 213 of the treatment instrument insertion passage of the endoscope 10, pushes the cable forwards/outwards, allows the hairpin portion 263 to project from the hole 261 of the incising instrument holding portion 243, supplies power, and adds the small incision only to the mucosa 251.

Subsequently, the high-frequency cable 233 is pulled in the vicinity of the inlet 213 of the treatment instrument insertion passage, the semicircular wire 247 is moved backwards, the hairpin portion 263 is contained in the incising instrument holding portion 243, and the incising instrument introducing portion 245 is inserted under the mucosa in this state.

Here, when the size of incision is insufficient, and the incising instrument introducing portion 245 is not inserted under the mucosa, the hairpin portion 263 is projected again, and inserted into the small incision formed beforehand. The endoscope 10 is bent and rotated/operated, power is supplied, and the incised part is expanded.

Subsequently, the inserting operation of the endoscope 10 and the sucking and air supply operation are performed, the semicircular portion of the wire 247 is brought in contact with the mucosa 251, high-frequency power is supplied to the wire 247 and an incision 244b is added to the mucosa 251 in the longitudinal direction. Another incision 244b of the longitudinal direction is similarly added, and the incisions are formed in the shape of two lines extending parallel to each other via the affected area 271.

The next step will be described with reference to FIG. 80. The endoscope 10 for use herein has two outlets 215 of the treatment instrument insertion passages, and a forceps elevator mechanism 219 by a forceps elevator base is disposed in one insertion passage outlet 215a.

Moreover, the hood 260 on the tip end is the same as that of the twenty-first embodiment, and is used to form two incisions 274a in the circumferential direction. A quadrangular incision line 274 is formed at a little distance in the periphery of the affected area 271.

Subsequently, the operator grasps the stump with the high-frequency grip forceps 255, raises the forceps elevator base of the forceps elevator mechanism 219, pushes inwards the high-frequency grip forceps 255, turns over the mucosa 251, brings the sharp edge 241 of the tip end of the hood 260 in contact with the boundary tissue 253, observes the incised part while rotating the endoscope 10, swings the edge in the circular arc shape, moves forwards the edge, and partially strips the mucosa 251 of the affected area 271 in a quadrangular shape.

Here, the high-frequency cable 233 is hard. By the pushing/pulling operation in the vicinity of the inlet 213 of the treatment instrument insertion passage, the semicircular portion of the wire 247 can easily be moved forwards/backwards. The projecting length of the hairpin portion 263 is regulated, when the front end of the slit 262 abuts on the front side of the wire 247. Therefore, the hairpin portion is prevented from projecting by more than the length equal to the thickness of the mucosa 251.

Moreover, since the mucosa 251 swollen in the bump shape is stretched to be thin, the mucosa can sufficiently be cut with the projecting amount corresponding to the thickness of the mucosa 251. The hairpin portion 263 is contained in the incising instrument holding portion 243 under the mucosa. Therefore, even when power is supplied during the incising of the mucosa, the portion does not contact the backside of the mucosa 251, or does not contact the muscle layer 252. That is, the portion is electrically insulated. Since the semicircular wire 247 is constantly directed toward the axial center via the slit 262, the wire does not contact the muscle layer 252. Moreover, when the wire 247 is brought under the mucosa, the mucosa 251 is lifted up along the wire 247, and a moment of incision of the mucosa 251 is reflected as the endoscope image.

When the affected area 271 is not present in the whole circumference and is partially present, the periphery of the affected area 271 is incised beforehand, and thereby the partial incising can easily be performed. Therefore, as compared with the conventional partial resecting method of sucking the mucosa 251 into the hood or the tip end of the guide tube, and squeezing and resecting the mucosa with the snare, it is possible to resect the mucosa in a broader range, such as a ½ circumferential of esophagus. The mucosa can easily be resected in the short time and in the broad range as compared with the method of raising or turning over the mucosa 251 and incising the mucosa lower layer little by little with the tip end of the incising instrument.

Moreover, even with the circumferential affection of the mucosa of the lumen organ, when the whole circumference is resected, this is a large invasion, burdens such as pain are given to the patient, and there is not a little danger of stenosis. Therefore, after a little period of time, the mucosa is partially resected according to the plan. In this case, the present example is effective because the partial resection can be easily performed.

Furthermore, in the conventional partial resection of sucking the mucosa into the cap or the tip end of the guide tube and squeezing and resecting the mucosa with the snare, it is impossible to directly observe the part to be incised with the endoscope image, but the part can be observed in the twenty-second embodiment. Additionally, in the method of partially resecting the mucosa in the elliptical shape, during the planned partial resection, if adjacent and overlapped parts are enlarged, the mucosa is resected deeply. Conversely, when the overlapped resection fails, the affected area cannot be removed, and an operation of carefully overlapping the resection over a time is necessary. However, since the mucosa can be incised in the quadrangular shape in the present example, the planned partial resection is secure and easy. Since the resected mucosa can easily be reconstructed, an effect of increasing accuracy of a pathological check result can be expected.

(Twenty-Third Embodiment)

Figure 81:
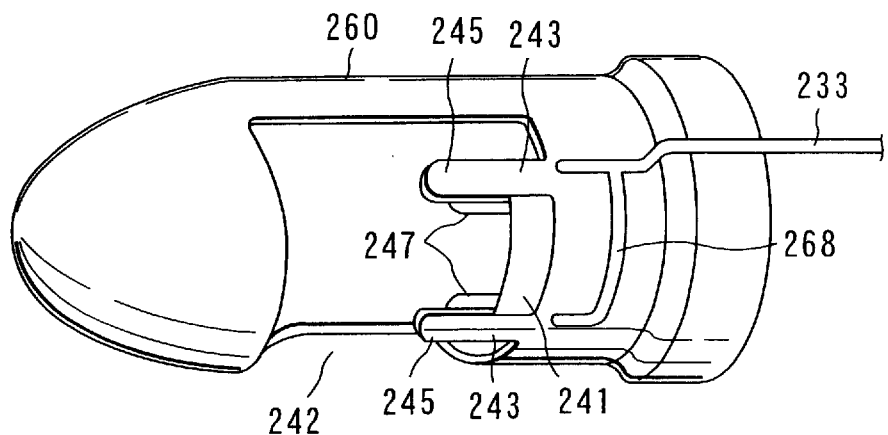
FIG. 81 is a perspective view of the vicinity of the tip end of the treatment apparatus for the endoscope according to a twenty-third embodiment.

FIG. 81 shows the treatment apparatus for the endoscope according to a twenty-third embodiment.

In the endoscope treatment apparatus of the twenty-third embodiment, as shown in FIG. 81, the attachable/detachable hood 260 is detachably attached to the tip-end portion 12 of the endoscope 10. The hood 260 is formed of a transparent and flexible polyurethane resin, and the tip-end portion thereof has a bullet shape. The side aperture 242 of the hood 260 is largely opened substantially over a ⅔ circumference of the hood 260. In the aperture, two incising instrument holding portions 243 are formed integrally with the hood 260, project in the axial direction and are disposed in parallel to each other. An interval of about 90 degrees for the circumferential angle is made between two incising instrument holding portions 243. On a side portion of the side aperture 242 positioned between two incising instrument holding portions 243, the sharp edge 241 is obliquely formed like a web and guillotine blade. The sharp edge 241 is formed of the same material integrally with the hood 260. Additionally, the positions of the incising instrument introducing portions 245 in two incising instrument holding portions 243 deviate a little in the axial direction.

On the backside of each incising instrument holding portion 243, the wire 247 extending along the inner edge of the incising instrument holding portion 243 from the rear portion of the incising instrument introducing portion 245 in the tip end of the holding portion is attached so as to project toward the center of the hood 260 in the circular arc shape. Moreover, the sharp edge 241 is positioned midway in the wire 247.

The rear portion of the wire 247 is connected to the high-frequency cable 233. The tip end of the high-frequency cable 233 is two-forked, and each tip end is connected to the wire 247. The wire 247 is fit in a groove 268 formed in the outer wall of the hood 260, and bonded so as not to jut out from the outer surface of the hood 260.

When the endoscope treatment apparatus of the twenty-third embodiment is used, first the physiological saline is injected under the mucosa in the method of using the syringe needle, and the mucosa 251 of the affected area 271 is raised with respect to the muscle layer 252. Thereafter, the hood 260 attached beforehand to the tip-end portion 12 of the endoscope 10 similarly as the second embodiment is rotated in the circumferential direction, and two incisions of the peripheral direction are added to forward and inward parts of the muscle layer 252 at a circumferential angle of about 90 degrees with the wire (incising instrument) 247 of the hood 260.

Thereafter, the hood 260 is replaced with the hood of the twenty-third embodiment, the part of the circumferential incision line 272a formed beforehand is sucked into the side aperture 242, the opposite ends are positioned, the air supply and sucking operation is adjusted, and the tip-end portion 12 of the endoscope 10 is moved forwards. The two incising instrument holding portions 243 are inserted from the tip-end incising instrument introducing portions 245, and further moved forwards so that the mucosa 251 uniformly rides onto two wires 247, high-frequency power is supplied to the wires 247 and the part of the mucosa 251 is incised.

In this case, since smoke and steam are generated, the air supply and sucking operation of the endoscope 10 is quickly repeated and the smoke and steam are removed.

The wires 247 are further pushed forwards into the parts to be incised together with the incising instrument holding portions 243. At the same time, the sharp edge 241 is brought into the boundary tissue 253 and pushed forwards, so that the boundary is incised and the mucosa 251 is stripped from the muscle layer 252. In order to easily observe the stripped part, the stump is grasped with the high-frequency grip forceps 255, and the mucosa 251 is turned over similarly as shown in FIG. 80. In this manner, the incising of the longitudinal direction and the stripping are simultaneously performed up to the part of the inward circumferential incision line 274 incised beforehand. Thereby, the mucosa 251 can be stripped in the quadrangular shape.

In the twenty-third embodiment, two wires 247 are disposed at an equal interval and moved in parallel in the axial direction. However, the two wires 247 are disposed along the edges of the incising instrument holding portions 243, not in the middle of the holding portion. Therefore, nothing remains uncut between the stripped part by the sharp edge 241 and the incision line of the axial direction.

Moreover, since the positions of the incising instrument introducing portions 245 in two incising instrument holding portions 243 deviate a little, insertion resistance is reduced. Since the sharp edge 241 is obliquely formed, stripping resistance is further reduced.

Since two incisions of the longitudinal direction are formed substantially simultaneously with the stripping of the mucosa 251, a stripping treatment can be performed in the short time. If the lines are incised one by one, it is difficult to incise the lines in parallel. It is more difficult to incise longer lines. However, when the hood 260 is used, the long parallel incisions can easily be formed simultaneously with the stripping.

Furthermore, the incising instrument introducing portion 245 does not have a sharp shape, and is formed of the flexible material. Therefore, if the portion inserted in the boundary tissue abuts on the muscle layer 252, the layer is not damaged.

MODIFICATION EXAMPLE

In the twenty-third embodiment, two wires 247 are disposed as the incising instrument, but the interval is not limited to 90 degrees, and any angle may be used if necessary. Moreover, the wire may be disposed on the guide tube 203, instead of the hood 260, similarly as the twentieth embodiment. Furthermore, the sharp edge 241 may be formed in the circular arc shape, and the middle thereof may be sharpened in a V shape. Additionally, the wire 247 may be formed in a slope shape. The projecting direction is not limited to the axial direction. If the wire partially projects in the circumferential form from the hood 260 or the guide tube 203, two circumferential incisions can be formed in the mucosa.

(Twenty-Fourth Embodiment)

Figure 82:
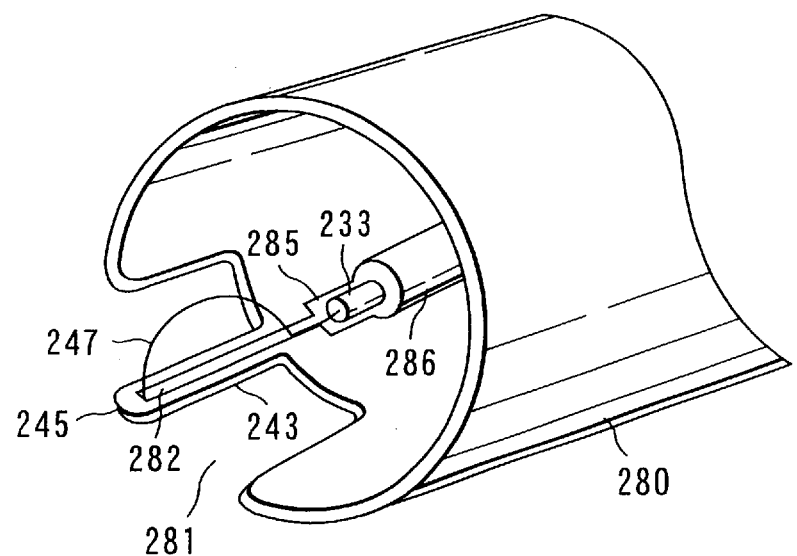
FIG. 82 is a perspective view of the vicinity of the tip end of the treatment apparatus for the endoscope according to a twenty-fourth embodiment.

FIG. 82 shows the endoscope treatment apparatus according to a twenty-fourth embodiment.

In the twenty-fourth embodiment, an example of the high-frequency incising apparatus with the wire 247 disposed in the axial direction therein is shown. That is, a cutout 281 opened forwards is disposed in the tip-end portion of a transparent and flexible resin tubular member (e.g., inner tube or hood) 280, and one strip-shaped incising instrument holding portion 243 extending forwards is left uncut in the rear wall (side) of the cutout 281. That is, the incising instrument holding portion 243 is positioned in the middle of the cutout 281 and disposed to project forwards.

A slit groove 282 is formed in the middle of the incising instrument holding portion 243, and extends to the rear portion of the incising instrument introducing portion 245. The tip end of the wire 247 is fixed to the tip end of the slit groove 282, and the wire 247 is contained in the slit groove 282. The wire 247 is curled in the circular arc shape beforehand.

The rear end of the wire 247 is connected to the hard high-frequency cable 233 covered with a thermally contractible tube of Teflon on the electrical insulation coat. The high-frequency cable 233 is slidably contained in a cable insertion passage 286 disposed in a cable groove 285 formed integrally with the tubular member 280.

Additionally, the width of the slit groove 282 is slightly larger than the outer diameter of the wire 247, and the containing and the exposing are smoothly repeated. A curve applied to the wire 247 is directed in the center axial direction of the tubular member 280, and is exposed in the corresponding direction.

Only the respect different from the above-described respect will be described. The operation comprises: picking up the mucosa 251 with the grip forceps inserted through the treatment instrument insertion passage of the endoscope; aligning the incising instrument introducing portion 245 of the incising instrument holding portion 243 with the small incision formed beforehand; and pulling the high-frequency cable 233 and inserting the wire 247 under the mucosa in the vicinity of the root of the incising instrument holding portion 243 contained in the slit groove 282. Subsequently, the operation comprises: pushing inwards the high-frequency cable 233; exposing the wire 247 in the circular arc shape; supplying power while incising the mucosa 251 from the backside of the mucosa 251; and moving forwards the wire to a desired position.

Since the wire 247 is contained in the incising instrument holding portion 243, the wire 247 is not an obstruction during the inserting of the incising instrument holding portion 243 under the mucosa, and the wire can be inserted long to the vicinity of the root. Therefore, the wire 247 can be positioned under the mucosa long, the mucosa can be incised long, and as a result, the time for incising the mucosa in the axial direction can be shortened.

Moreover, since the tip end of the tubular member 280 is opened, the smoke or steam generated during the incision does not easily stay in the tubular member 280, and it is easy to secure the view field.

Furthermore, since the high-frequency cable 233 is contained in the predetermined position, the treatment operation and view field are not obstructed. Additionally, instead of the side aperture, the cutout 281 opened forwards is disposed, and the view field visible with the endoscope 10 is broadened.

MODIFICATION EXAMPLE

The angle of the tip-end incision is not limited to the right angles, and the tip end may obliquely be cut so as to facilitate the inserting or the sucking.

(Twenty-Fifth Embodiment)

Figure 83:
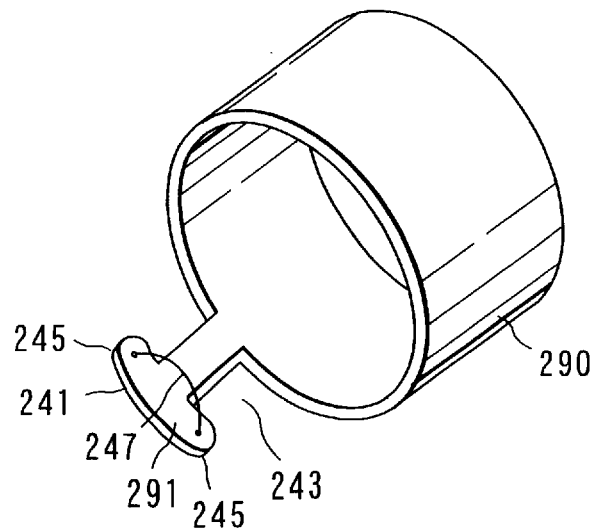
FIG. 83 is a perspective view of the vicinity of the tip end of the treatment apparatus for the endoscope according to a twenty-fifth embodiment.

FIG. 83 shows the endoscope treatment apparatus according to a twenty-fifth embodiment.

In the example of the twenty-fifth embodiment, another example of the high-frequency incising instrument for use in the peripheral incision is shown. That is, the T-shaped incising instrument holding portion 243 is formed to project forwards in the forward opening end of a transparent and flexible resin tubular member, that is, a hood 290. A piece 291 extending in opposite directions of the periphery is formed in the tip end of the incising instrument holding portion 243. The front edge of the T-shaped piece 291 is formed as the sharp edge 241 for incising the tissue.

The transverse-line piece 291 of the incising instrument holding portion 243 is curved and formed parallel to the peripheral surface of the hood 290. The wire 247 directed inwards is extended in the chord shape on the inner surface of the T-shaped piece 291 having a circular arc shape.

The opposite ends of the wire 247 are disposed apart forwards from the end of the piece 291, and the opposite tip-end portions of the piece 291 form the respective incising instrument introducing portions 245.

The respect different from the above-described respect will be described. To incise the whole circumference, the possible incision comprises: rotating the wire by 180 degrees in the clockwise or counterclockwise direction and forming the incision; rotating the wire in the opposite direction; bringing the tip-end introducing portion on the opposite side of the T shape into the incised end; rotating the wire by 180 degrees in the direction opposite to the initial direction and adding the incision; and connecting the incisions at 360 degrees.

By the sucking operation of the endoscope, the incising instrument can be brought under the mucosa in any rotation direction with respect to the raised mucosa. Moreover, it is unnecessary to rotate the hood 290 by 360 degrees, and the rotating operation is facilitated.

When the mucosa is incised, blood and tissue are burnt to stick to the wire 247, and the wire does not easily cut sometimes. However, the half periphery is incised by the half of the circular arc shaped wire. The wire does not easily wear as compared with the incising of the whole periphery by the same portion of the wire. Since the rotating operation of the incising instrument is performed in the lumen organ such as esophagus, the organ is twisted not a little. However, as compared with the rotation by 360 degrees in the same direction, the instrument is half rotated, and the burdens onto the patient can be reduced. A contact area between the mucosa and the outer surface of the hood is small, rotation resistance is little, the rotation is facilitated, and therefore the operator does not get tired. The hood can be shortened as compared with the side aperture, so that the rotation resistance can be reduced and the rotating operation is similarly facilitated. Moreover, the portion of the hood in the endoscope image is reduced, and the body cavity can easily be observed. The hood does not easily form an obstruction, and the treatment operation by the treatment instrument is also facilitated.

MODIFICATION EXAMPLE

The T-shaped incising instrument holding portion 243 may be disposed in the above-described side aperture or the cutout. Moreover, the shape of the wire is not limited to the circular arc. The T shape may be rotated by 90 degrees, and the wire 247 may be disposed in the axial direction as in the embodiment shown in FIG. 81. Furthermore, the incising instrument holding portion may be formed in an L-shape, and may be formed as an incising instrument rotatable by 360 degrees.

MODIFICATION EXAMPLE

Figure 84A:
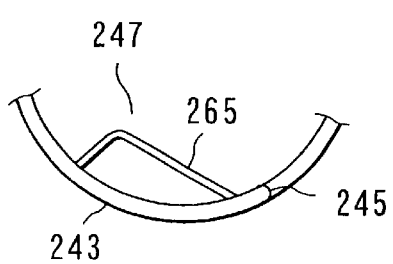
FIGS. 84A to 84C are explanatory views showing different modification examples of an incising instrument.
Figure 84B:
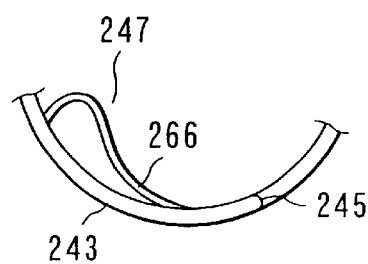
Figure 84C:
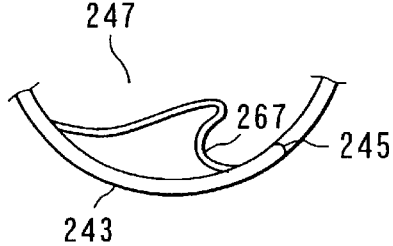
Figure 85:
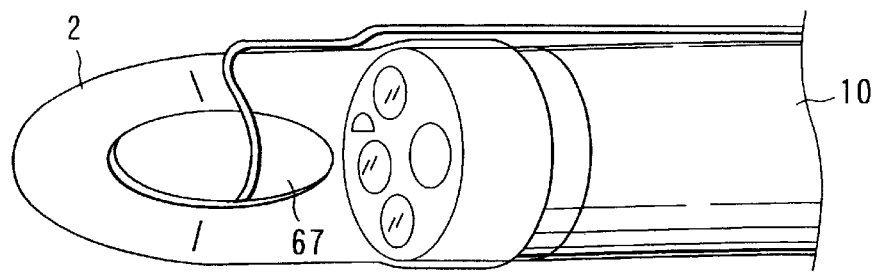
FIG. 85 is a perspective view of a conventional treatment apparatus for the endoscope.
Figure 86:
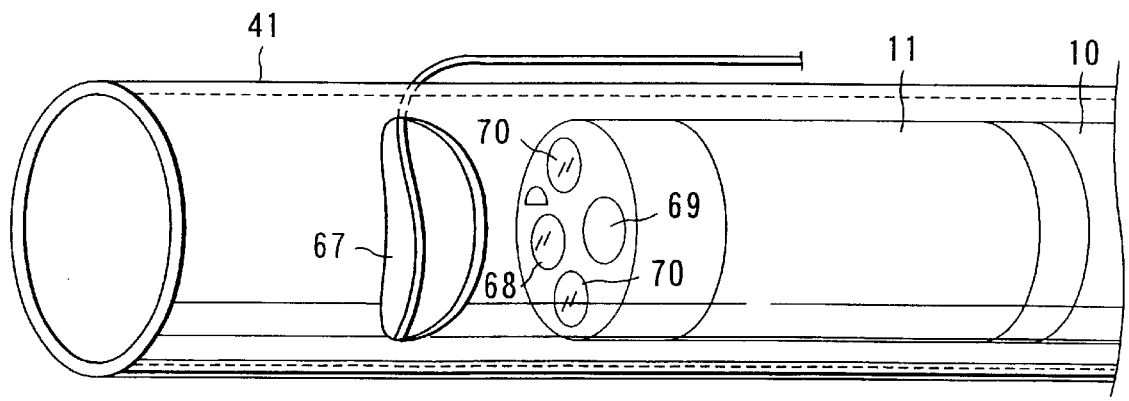
FIG. 86 is a perspective view of another conventional treatment apparatus for the endoscope.

The shape of the portion of the wire 247 projecting from the incising instrument holding portion 243 may be a parabolic line, a portion of ellipse, a half of ellipse, or a slope. FIGS. 84A to 84C show the examples.

In FIG. 84A, the projecting portion of the wire 247 is formed in a shape such that a linear slope 265 suddenly rises. When the linear slope 265 suddenly rises, the portion of the wire 247 easily contacts the back of the mucosa, and the mucosa is easily incised.

In FIG. 84B, the projecting portion of the wire 247 forms a gently curved slope 266. Since the slope 266 has a gently curved shape, the wire 247 does not easily form the obstruction during the inserting of the incising instrument under the mucosa. The incising instrument can smoothly be inserted under the mucosa, a long range of the wire 247 is covered with the mucosa, and the mucosa can be cut long.

In FIG. 84C, the projecting portion of the wire 247 forms a wire portion 267 having a dorsal fin shape, and is disposed in the incising instrument holding portion 243. Since the mucosa contacts the circular arc portion having a small curvature on the side of the introducing portion 245 of the dorsal fin shaped wire portion 267, the end of the mucosa is cut, not the back of the mucosa. It is unnecessary to bring the wire 247 under the mucosa. Therefore, the resistance is little, the rotating operation is facilitated, and the incised part can easily be observed.

MODIFICATION EXAMPLE

The position where the wire of each example is disposed is not limited to the circumferential incising instrument, and the wire may be disposed in the axial direction.

The present invention is not limited to the above-described embodiments. According to the above description, the following terms and the optional combination of the respective terms are obtained.

Additionally, the present invention has been described with relation to the preferable embodiments shown in the various drawings, but it is obvious that another similar embodiment is used or the above-described embodiments may be changed or added to obtain the same function as that of the present invention without departing from the present invention. Therefore, the present invention is not limited to any single embodiment, and should be interpreted according to the scope described in claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment apparatus for an endoscope, which is inserted into a body cavity together with a tip-end portion of the endoscope, and which treats a tissue in the body cavity, the apparatus comprising:
    a base disposed in the vicinity of the tip-end portion of said endoscope;
    an in-tissue inserting portion including a base end supported by the base, and a tip end which can be inserted into the tissue in the body cavity in a direction parallel to the surface of the tissue, extending to the tip end from the base end in a tapered shape, and having an inner side disposed in the vicinity of the surface of the tissue when inserted into said tissue;
    a high-frequency electrode for treating the tissue, which is supported by said base and disposed in the vicinity of the inner side of the in-tissue inserting portion; and
    a cable which supplies power to the high-frequency electrode from a high-frequency power supply apparatus disposed outside the body.

2. A treatment apparatus for an endoscope, which is used in combination of the endoscope having a tip-end portion to be inserted in a body cavity, and used in treating a tissue in the body cavity, the apparatus comprising:
    a tubular member which is disposed in the vicinity of a tip end of the endoscope, and includes a cylindrical side wall;
    an aperture formed in said side wall;
    an in-tissue inserting portion which is supported by the side wall of said tubular member, has a tip end projecting into the aperture, has a tapered shape, and has an inner surface disposed in the vicinity of a surface side of the tissue when inserted into said tissue;
    a high-frequency electrode for treating the tissue, which is disposed on an inner surface side of said in-tissue inserting portion; and
    a cable which supplies power to the high-frequency electrode from a high-frequency power supply apparatus disposed outside the body.

3. A treatment apparatus for the endoscope according to claim 2, wherein said high-frequency electrode is extended in a chord shape in a plane vertical with respect to an axial direction of the tubular member.

4. A treatment apparatus for the endoscope according to claim 2, wherein said high-frequency electrode extends in the axial direction of the tubular member.

5. A treatment apparatus for an endoscope, which is used in combination with the endoscope having a tip-end portion to be inserted into a body cavity, and used in treating a tissue in the body cavity, the apparatus comprising:
    a tubular member which is disposed in the vicinity of the tip-end portion of the endoscope, and formed of an electrical insulator transparent and superior in heat resistance;
    an in-tissue inserting portion which projects from said tubular member, is formed of a material superior in heat resistance and electrical insulation, and has an inner surface disposed in the vicinity of a surface side of the tissue when inserted into said tissue;
    a high-frequency incising instrument having an incising portion disposed at a predetermined distance from an inner surface of the in-tissue inserting portion; and
    a cable which supplies power to the incising portion of the high-frequency incising instrument from a high-frequency power supply apparatus disposed outside the body.

6. A treatment apparatus for the endoscope according to claim 5, wherein said tubular member is formed of a transparent and flexible material, and further includes an outer cylinder to contain the tubular member in an airtight manner so that the tubular member can be rotated and moved forwards/backwards, and the outer cylinder is shorter than said tubular member.

7. A treatment apparatus for the endoscope according to claim 5, wherein said in-tissue inserting portion projects from the tubular member in the axial direction.

8. A treatment apparatus for an endoscope, which is used in combination of the endoscope having a tip-end portion to be inserted into a body cavity, and used in treating a tissue in the body cavity, the apparatus comprising:
    a tubular member which is disposed in the vicinity of a tip end of the endoscope, and includes a cylindrical side wall including an aperture;

an in-tissue inserting portion having a tapered shape which projects toward said aperture;

a deformable high-frequency electrode for treating the tissue, which is disposed at a predetermined distance from said in-tissue inserting portion inside said tubular member, and can abut on said in-tissue inserting portion by an operation outside a body; and a cable which supplies a high-frequency current to the high-frequency electrode from a high-frequency power supply apparatus.

9. A treatment apparatus for the endoscope according to claim 8, wherein said high-frequency electrode is coated in order to be prevented from being burnt.

10. A treatment apparatus for the endoscope according to claim 8, wherein said in-tissue inserting portion is formed integrally with or separately from the tubular member, and projects in an axial direction.

11. A treatment apparatus for the endoscope according to claim 8, wherein said in-tissue inserting portion is formed integrally with or separately from the tubular member, and projects in a peripheral direction.

12. A treatment apparatus for the endoscope according to claim 8, wherein said in-tissue inserting portion can be rotated with respect to the tubular member.

13. A treatment apparatus for an endoscope, which is used in combination with the endoscope having a tip-end portion to be inserted in a body cavity, and used in treating a tissue in the body cavity, the apparatus comprising:

a tubular member which is disposed in the vicinity of the tip-end portion of the endoscope, and includes a cylindrical side wall;

first and second apertures disposed in the side wall of said tubular member;

first and second in-tissue inserting portions which are disposed in said tubular member, and have tapered shapes projecting toward the respective apertures;

a first high-frequency electrode for treating the tissue, which is disposed on an inner surface side of said first in-tissue inserting portion, and extends into a plane vertical to an axial direction of said tubular member;

a second high-frequency electrode for treating the tissue, which is disposed on the inner surface side of said second in-tissue inserting portion, and extends in the axial direction of said tubular member; and a plurality of cables which supply a high-frequency current to the respective high-frequency electrodes.

14. A treatment apparatus for the endoscope according to claim 13, further comprising a power-supply apparatus located outside the body, and a switch apparatus for connecting at least one of the cables to the power-supply apparatus.

15. A treatment apparatus for the endoscope according to claim 13, further comprising: identification means different in at least one portion of each of said first and second high-frequency electrodes entering an endoscope view field; and first and second connectors disposed on a base ends of said cable, wherein the same identification means as the identification means for the first and second high-frequency electrodes are disposed in at least one portion of each of these connectors.

16. A treatment apparatus for the endoscope according to claim 13, wherein an angle of said high-frequency electrode to a tangent line of the tubular member in a connection point with the in-tissue inserting portion is in the range of 0° to 90°.

17. A treatment apparatus for the endoscope according to claim 13, wherein the angle of said high-frequency electrode to a tangent line of the tubular member in a connection point with the in-tissue inserting portion is in the range of 90° to 180°.

18. The treatment apparatus for the endoscope according to claim 13, wherein said first high-frequency electrode and second high-frequency electrode are disposed in positions in which the respective electrodes do not interfere with each other, and further a treatment instrument for the endoscope projected from the endoscope tip end is not interfered with.

19. A treatment apparatus for an endoscope, which is used in combination with an endoscope having a tip-end portion to be inserted into a body cavity, and used in treating a tissue in the body cavity, the apparatus comprising:

a base disposed in the vicinity of a tip-end portion of the endoscope;

a first high-frequency electrode for treating the tissue, which is supported by the base, and extends in a first direction;

a second high-frequency electrode for treating the tissue, which is supported by the base, and extends in a second direction different from the first direction;

a high-frequency power supply apparatus disposed outside the body;

first and second cables which are connected to said first and second high-frequency electrodes, and supply high-frequency currents to the first and second high-frequency electrodes from said high-frequency power supply apparatus; and a switch apparatus which is disposed between said high-frequency power supply apparatus and the first and second cables, and selectively and electrically connects the high-frequency power supply apparatus to the first and second cables.

* * * * *